US009777044B2

(12) United States Patent
Battini et al.

(10) Patent No.: US 9,777,044 B2
(45) **Date of Patent: *Oct. 3, 2017**

(54) GLUT-1 AS A RECEPTOR FOR HTLV ENVELOPES AND ITS USES

(71) Applicants: CENTRE NATIONAL DE LA RECHERCHE SCIENTIFIQUE (CNRS), Paris (FR); UNIVERSITE DE MONTPELLIER 2, Montpellier (FR)

(72) Inventors: Jean-Luc Battini, Montpellier (FR); Nicolas Manel, Paris (FR); Felix Kim, New York City, NY (US); Sandrina Kinet, Claret (FR); Naomi Taylor, Montpellier (FR); Marc Sitbon, Montpellier (FR)

(73) Assignees: CENTRE NATIONAL DE LA RECHERCHE SCIENTIFIQUE (CNRS), Paris (FR); UNIVERSITE DE MONTPELLIER 2, Montpellier (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/575,132

(22) Filed: Dec. 18, 2014

(65) Prior Publication Data

US 2015/0133363 A1 May 14, 2015

Related U.S. Application Data

(60) Continuation-in-part of application No. 12/547,924, filed on Aug. 26, 2009, now Pat. No. 8,945,583, which is a division of application No. 10/555,289, filed as application No. PCT/EP2004/004624 on Apr. 30, 2004, now Pat. No. 7,642,061.

(30) Foreign Application Priority Data

May 2, 2003 (EP) .................................... 03291067

(51) Int. Cl.

| | |
|---|---|
| ***C07K 14/005*** | (2006.01) |
| ***C12N 7/00*** | (2006.01) |
| ***C07K 14/62*** | (2006.01) |
| ***C07K 14/705*** | (2006.01) |
| ***G01N 33/566*** | (2006.01) |
| ***G01N 33/574*** | (2006.01) |
| *A61K 38/00* | (2006.01) |

(52) U.S. Cl.

CPC ............ *C07K 14/005* (2013.01); *C07K 14/62* (2013.01); *C07K 14/705* (2013.01); *G01N 33/566* (2013.01); *G01N 33/57484* (2013.01); *A61K 38/00* (2013.01); *C12N 2740/14022* (2013.01); *C12N 2740/14033* (2013.01); *C12N 2740/15022* (2013.01); *C12N 2740/15045* (2013.01); *C12N 2810/6054* (2013.01); *G01N 2333/62* (2013.01)

(58) Field of Classification Search

None

See application file for complete search history.

(56) References Cited

U.S. PATENT DOCUMENTS

| | | | | |
|---|---|---|---|---|
| 5,897,991 | A | 4/1999 | Burstein et al. | |
| 7,507,526 | B2 | 3/2009 | Miller et al. | |
| 7,642,061 | B2 * | 1/2010 | Battini ................ | A61K 38/162 435/5 |
| 2004/0176314 | A1 | 9/2004 | Beseme et al. | |
| 2010/0056448 | A1 | 3/2010 | Battini et al. | |
| 2015/0133363 | A1 * | 5/2015 | Battini .................. | C07K 14/62 514/1.2 |

FOREIGN PATENT DOCUMENTS

| | | | |
|---|---|---|---|
| EP | 0384566 | A2 | 8/1990 |
| WO | 88/05783 | | 8/1988 |
| WO | 8805783 | A1 | 8/1988 |
| WO | 92/13946 | | 8/1992 |
| WO | WO 95/01457 | * | 11/1995 |
| WO | 96/21727 | | 7/1996 |
| WO | 9621727 | A1 | 7/1996 |
| WO | 96/41193 | | 12/1996 |
| WO | 97/15668 | | 5/1997 |
| WO | 9715668 | A2 | 5/1997 |
| WO | 98/03197 | | 1/1998 |
| WO | 99/45920 | | 9/1999 |
| WO | 9945920 | A2 | 9/1999 |
| WO | 99/59559 | | 11/1999 |
| WO | 9959559 | A1 | 11/1999 |
| WO | 0046403 | A2 | 8/2000 |
| WO | 0131021 | A1 | 5/2001 |
| WO | 02095400 | A2 | 11/2002 |
| WO | 03092582 | A2 | 11/2003 |

(Continued)

OTHER PUBLICATIONS

Park (PLoSOne. Apr. 2015; DOI: 10.1371/journal.pone.01025361: 1-18).*

Sequence alignment of Seq ID No. 4 with Geneseq database access No. AAR64975 of Lee et al in WO 9501457 (1995).*

Sequence alignment of Seq ID No. 5 with Geneseq database access No. AAR64975 by Lee et al. in WO 9501457 (1995).*

Sequence alignment of Seq ID No. 7 with Geneseq database access No. AAR64975 of Lee et al in WO 9501457 (1995).*

Sequence alignment of Seq ID No. 43 with Geneseq database access No. AAR64975 of Lee et al in WO 9501457 (1995).*

ISR of the PCT application WO20041096841 (Aug. 10, 2004).

Jones et al The receptor complex associated with human T-cell lymphotropic virus type 3 (HTLV-3) Env-mediated binding and entry is distinct from, but overlaps with, the receptor complexes of HTLV-1 and HTLV-2, J Virol. May 2009; 83(10):5244-55.

Kim et al "HTLV-1 and -2 envelope SU subdomains and critical determinants in receptor binding." Retrovirology. Dec. 2, 2004;1:41.

(Continued)

*Primary Examiner* — Shanon A Foley

(74) *Attorney, Agent, or Firm* — Young & Thompson

(57) ABSTRACT

The present application relates to polypeptides derived from the soluble part of the glycoprotein of the enveloped virus of Primate T-cell leukemia virus (PTLV), or fragments or variants thereof named receptor binding domain ligands (RBD) selected for their ability to bind specifically to the nutrient transporter GLUT1.

17 Claims, 14 Drawing Sheets

(56) References Cited

FOREIGN PATENT DOCUMENTS

| | | | |
|---|---|---|---|
| WO | 2005095442 | A1 | 10/2005 |
| WO | 2010079208 | A1 | 7/2010 |

OTHER PUBLICATIONS

Manel N et al "GLUT-1 is the receptor of retrovirus HTLV" 2004 Medecine Sciences 20(3):277-279.

Manel, N. et al. "The HTLV receptor is an early T-cell activation marker whose expression requires de novo protein synthesis" Blood Mar. 1, 2003; vol. 101 No. 5 pp. 1913-1918.

Mueckler M and Makepeace C, Identification of an amino acid residue that lies between the exofacial vestibule and exofacial substrate-binding site of the Glut1 sugar permeation pathway, (1997) J Biol Chem 272(48): 30141-6.

Harris D S et al: "Polarized Distribution of Glucose Transporter Isoforms in CACO-2 Cells", Proceedings of the National Academy of Sciences of the United States, vol. 89, No. 16, 1992, pp. 7556-7560, XP002254293, 1992 ISSN: 0027-8424, p. 7557, col. 1, line 4-line 11 p. 7557, col. 2, paragraph 2; figures 1, 3A, p. 7559, col. 2, last paragraph.

Mendez Luis E et al: "Expression of glucose transporter-1 in cervical cancer and its precursors." Gynecologic Oncology, vol. 86, No. 2, Aug. 2002 (Aug. 2002), pp. 138-143, XP002254294 Aug. 2002, ISSN: 0090-8258 cited in application, p. 140, col. 2, line 7—p. 141, col. 1, line 2; table 3, p. 142, col. 1, paragraph 1.

Lairmore M D et al: "Characterization of a B-Cell Immunodominant Epitope of Human T-Lymphotropic Virus Type 1 (HTLV-I) Envelope GP46" Cancer Letters, New York, NY, US, vol. 66, Sep. 14, 1992 (Sep. 14, 1992), pp. 11-20, XP000940582, ISSN: 0304-3835 abstract.

Tallet B et al: "Sequence variations in the amino- and carboxy-terminal parts of the surface envelope glycoprotein of HTLV type 1 induce specific neutralizing antibodies." AIDS Research and Human Retroviruses. United States Mar. 1, 2001, vol. 17, No. 4, Mar. 1, 2001 (Mar. 1, 2001), pp. 337-348, XP002254296 ISSN: 0889-2229, p. 346, col. 2, last paragraph, abstract.

Manel Nicolas et al: "GLUT-1 is the receptor of retrovirus HTLV!" Medecine Sciences: M/S. Mar. 2004, vol. 20, No. 3, Mar. 2004 (Mar. 2004), pp. 277-279, XP002293056, ISSN: 0767-0974, the whole document.

Manel Nicolas et al: "The ubiquitous glucose transporter GLUT-1 is a receptor for HTLV." Cell, vol. 115, No. 4, Nov. 14, 2003 (Nov. 14, 2003), pp. 449-459, XP002293058, ISSN: 0092-8674, the whole document.

Mueckler Mike et al: "Identification of an amino acid residue that lies between the exofacial vestibule and exofacial substrate-binding site of the Glut1 sugar permeation pathway." Journal of Biological Chemistry, vol. 272, No. 48, Nov. 28, 1997 (Nov. 28, 1997), pp. 30141-30146, XP002254295, ISSN: 0021-9258 cited in the application, figure 1.

Buck, et al. (European Journal of Nuclear Medicine and Molecular Imaging, 2004; (321, Supplement 1): S80-S87).

Wood, et al. (British Journal of Nutrition 89:3-9, 2003).

Vannucci, et al. (Glia 21:2-21, 1997).

Brown (Journal of Inherited Metabolic Diseases 23:237-246, 2000).

Young, et al. (American Journal of Cardiology 83:25H-30H, 1999).

Ojeda, et al. (American Journal of Physiology, Cell Physiology 2012; 303: C530-0539).

Koralnik, et al. (Journal of Virology, 1994; 68 (4): 2693-2707).

Mahieux, et al. (Viruses. 2011; 3: 1074-1090).

Jones, et al. (Journal of Virology. 2009; 83 (10): 5244-5255).

Sakashita, et al. (European Journal of Cancer 37:204-209, 2001).

Palker, et al. (Journal of Virological Methods 18:243-255, 1987).

Cavazzana-Calvo, Marina, "Gene therapy of human severe combined immunodeficiency (SCID)-X1 disease", 2000, Science, vol. 288, No. 5466, pp. 669-672.

Gaspar et al., "Gene therapy of X-linked severe combined immunodeficiency by use of a pseudotyped gammaretroviral vector", 2004, Lancet, vol. 364, No. 9452, pp. 2181-2187.

Manel et al., "HTLV envelopes and their receptor GLUT1, the ubiquitous glucose transporter: a new vision on HTLV infection?", 2004, Frontiers in Biosciences, vol. 9, pp. 3218-3241.

Jones et al., "Human T-cell leukemia virus type 1 (HTLV-1) and HTLV-2 use different receptor complexes to enter T cells", Journal of Virology, 2006, vol. 80, No. 17, pp. 8291-8302.

Uchiyama et al., "Functional regulation of Na+-dependent neutral amino acid transporter ASCT2 by S-nitrosothiols and nitric oxide in Caco-2 cells", 2005, FEBS Lett., vol. 579, No. 11, pp. 2499-2506.

Goubau et al., "A primate T-lymphotropic virus, PTLV-L, different from human T-lymphotropic viruses types I and II, in a wild-caught baboon (*Papio hamadryas*)", Proc Natl Acad Sci U S A, 1994, vol. 91, No. 7, pp. 2848-2852.

Perzova et al., "Lack of BLV and PTLV DNA sequences in the majority of patients with large granular lymphocyte leukaemia", Br J Haematol., Apr. 2000, vol. 109, No. 1, pp. 64-70.

Ramirez et al., "Genetic characterization and phylogeny of human T-cell lymphotropic virus type I from Chile", Virus Research, Mar. 20, 2002, vol. 84, No. 1-2, pp. 135-149.

Dube, S., "Degenerate and specific PCR assays for the detection of bovine leukaemia virus and primate T cell leukaemia/lymphoma virus pol DNA and RNA: phylogenetic comparisons of amplified sequences from cattle and primates from around the world", J Gen Virol., Jun. 1997, vol. 78, pp. 1389-1398.

Gray et al., "Envelope gene sequence of HTLV-1 isolate MT-2 and its comparison with other HTLV-1 isolates", Virology, Jul. 1990, vol. 177, No. 1, pp. 391-395.

Suarez et al., "Identification of hypervariable and conserved regions in the surface envelope gene in the bovine lentivirus", Virology, Oct. 1, 1995, vol. 212, No. 2, pp. 728-733.

Ting et al., "Simian sarcoma-associated virus fails to infect Chinese hamster cells despite the presence of functional gibbon ape leukemia virus receptors", J Virol., Dec. 1998, vol. 72, No. 12, pp. 9453-9458.

Harris et al., "Polarized distribution of glucose transporter isoforms in Caco-2 cells", Proc Natl Acad Sci U S A, 1992, vol. 89, No. 16, pp. 7556-7560.

Mendez et al., "Expression of glucose transporter-1 in cervical cancer and its precursors", 2002, Gynecol Oncol, vol. 86, No. 2, pp. 138-143.

Lairmore et al., "Characterization of a B-cell immunodominant epitope of human T-lymphotropic virus type 1 (HTLV-I) envelope gp46", Cancer Lett., Sep. 14, 1992, vol. 66, No. 1, pp. 11-20.

Tallet et al., "Sequence variations in the amino- and carboxy-terminal parts of the surface envelope glycoprotein of HTLV type 1 induce specific neutralizing antibodies", AIDS Res and Hum Retrovirus, 2001, vol. 17, No. 4, pp. 337-348.

Wood et al., "Glucose transporters (GLUT and SGLT): expanded families of sugar transport proteins", 2003, Br J Nutrition, vol. 89, pp. 3-9.

Adhikani et al., "Increase in GLUT1 in smooth muscle alters vascular contractility and increases inflammation in response to vascular injury", Arterioscler Thromb Vasc Biol., 2011, vol. 31, No. 1, pp. 86-94.

Afzal et al., "Interactions of ATP, oestradiol, genistein and the anti-oestrogens, faslodex (ICI 182780) and tamoxifen, with the human erythrocyte glucose transporter, GLUT1", 2002, Biochem J, vol. 365, pp. 707-719.

Akaoka et al., "Functional changes in astrocytes by human T-lymphotropic virus type-1 T-lymphocytes", Virus Res., 2001, vol. 78, No. 1-2, pp. 57-66.

Amann et al., "GLUT1 expression is increased in hepatocellular carcinoma and promotes tumorigenesis", 2009, Am J Pathol, vol. 174, No. 4, pp. 1544-1552.

Battellino et al., "Tissue glucose transport and glucose transporters in suckling rats with endotoxic shock", Shock, 1996, vol. 6, No. 4, pp. 259-262.

Battini et al., "A human cell-surface receptor for xenotropic and polytropic murine leukemia viruses: possible role in G protein-coupled signal transduction", Proc Natl Acad Sci USA, 1999, vol. 96, No. 4, pp. 1385-1390.

(56) References Cited

OTHER PUBLICATIONS

Berger et al., "Chemokine receptors as HIV-1 coreceptors: roles in viral entry, tropism, and disease", Annu Rev Immunol., Apr. 1999, vol. 17, pp. 657-700.
Boden et. al., "Glucose transporter proteins in human insulinoma", Ann Intern Med, Jul. 1994, vol. 121, No. 2, pp. 109-112.
Bos et al., "Biologic correlates of (18)fluorodeoxyglucose uptake in human breast cancer measured by positron emission tomography", 2002, J Clin Oncol, vol. 20, No. 2, pp. 379-387.
Brown, G. K., "Glucose transporters: structure, function and consequences of deficiency", 2000, J Inherited Metabol, vol. 23, pp. 237-246.
Brown et al., "Overexpression of Glut-1 glucose transporter in human breast cancer", An immunohistochemical study, Cancer, 1993, vol. 72, pp. 2979-2985.
Buck et al., "Biological characterisation of breast cancer by means of PET", 2004, Eur J Nucl Med Mol Imag, vol. 31, Suppl1, pp. S80-S87.
Bunn et al., "Protein interactions with the glucose transporter binding protein GLUT1CBP that provide a link between GLUT1 and the cytoskeleton", Mol Biol Cell, Apr. 1999, vol. 10, No. 4, pp. 819-832.
Cantuaria et al., "GLUT-1 expression in ovarian carcinoma: association with survival and response to chemotherapy", Cancer Sep. 2001, vol. 92, No. 5, pp. 1144-1150.
Cavrois et al., "Proliferation of HTLV-1 infected circulating cells in vivo in all asymptomatic carriers and patients with TSP/HAM", Oncogene, Jun. 1996, vol. 12, No. 11, pp. 2419-2423.
Chakrabarti et al., "Changes in glucose transport and transporter isoforms during the activation of human peripheral blood lymphocytes by phytohemagglutinin", J Immunol., Mar. 15, 1994, vol. 152, No. 6, pp. 2660-2668.
Clapham et al., "HIV-1 receptors and cell tropism", Br Med Bull, 2001, vol. 58, pp. 43-59.
Daenke et al., "HTLV-1-induced cell fusion is limited at two distinct steps in the fusion pathway after receptor binding", J Cell Sci, Jan. 2000, vol. 113, pp. 37-44.
Daenke et al., "Human T-cell leukaemia/lymphoma virus type 1 syncytium formation is regulated in a cell-specific manner by ICAM-1, ICAM-3 and VCAM-1 and can be inhibited by antibodies to integrin beta2 or beta7", J Gen Virol, Jun. 1999, vol. 80, pp. 1429-1436.
Russo et al., "Peroxisome proliferator-activated receptor gamma thiazolidinedione agonists increase glucose metabolism in astrocytes", 2003, J Biol Chem, vol. 278, No. 8, pp. 5828-5836.
Denesvre et al., "Influence of transmembrane domains on the fusogenic abilities of human and murine leukemia retrovirus envelopes", J Virol, Jul. 1995, vol. 69, No. 7, pp. 4149-4157.
Denesvre et al., "TM domain swapping of murine leukemia virus and human T-cell leukemia virus envelopes confers different infectious abilities despite similar incorporation into virions", J Virol, Jul. 1996, vol. 70, No. 7, pp. 4380-4386.
El-Barbary et al., "Barbiturate inhibition of GLUT-1 mediated hexose transport in human erythrocytes exhibits substrate dependence for equilibrium exchange but not unidirectional sugar flux", Biochemistry, 1996, vol. 35, No. 48, pp. 15222-15227.
Escher et al., "The *Drosophila* glucose transporter gene: cDNA sequence, phylogenetic comparisons, analysis of functional sites and secondary structures", Hereditas, 1999, vol. 130, No. 2, pp. 95-103.
Fan et al., "Glucose transporter protein 1-targeted RNA interference inhibits growth and invasion of the osteosarcoma cell line MG63 in vitro", 2010, Cancer Biother Radiopharm, vol. 25, No. 5, pp. 521-527.
Frauwirth et al., "The CD28 signaling pathway regulates glucose metabolism", Immunity, 2002, vol. 16, pp. 769-777.
Fukuzumi et al., "Endotoxin-induced enhancement of glucose influx into murine peritoneal macrophages via GLUT1", Infect Immun., Jan. 1996, vol. 64, No. 1, pp. 108-112.
Gamelli et al., "Augmentations of glucose uptake and glucose transporter-1 in macrophages following thermal injury and sepsis in mice", J Leukoc Biol., 1996, vol. 59, No. 5, pp. 639-647.
Garcia et al., "Molecular characterization of a membrane transporter for lactate, pyruvate, and other monocarboxylates: implications for the Cori cycle", Cell, Mar. 1994, vol. 76, No. 5, pp. 865-873.
Gessain et al., "Antibodies to human T-lymphotropic virus type-I in patients with tropical spastic paraparesis", The Lancet, Aug. 24, 1985, vol. 2, No. 8452, pp. 407-410.
Halestrap et al., "The proton-linked monocarboxylate transporter (MCT) family: structure, function and regulation", Biochem J, Oct. 1999, vol. 343, pp. 281-299.
Hall et al., "Deleted HTLV-I provirus in blood and cutaneous lesions of patients with mycosis fungoides", 1991, Science, vol. 253, pp. 317-320.
Hanon et al., "Fratricide among CD8(+) T lymphocytes naturally infected with human T cell lymphotropic virus type I", Immunity, Nov. 2000, vol. 13, No. 5, pp. 657-664.
Hellwig et al., "Differentiation of erythrocyte-(GLUT1), liver-(GLUT2), and adipocyte-type (GLUT4) glucose transporters by binding of the inhibitory ligands cytochalasin B, forskolin, dipyridamole, and isobutylmethylxanthine", 1991, Mol Pharmacol, vol. 40, No. 3, pp. 383-389.
Hildreth et al., "Human T-cell lymphotropic virus type 1 (HTLV-1)-induced syncytium formation mediated by vascular cell adhesion molecule-1: evidence for involvement of cell adhesion molecules in HTLV-1 biology", J Virol, Feb. 1997, vol. 71, No. 2, pp. 1173-1180.
Hoshino et al., "Detection of lymphocytes producing a human retrovirus associated with adult T-cell leukemia by syncytia induction assay", PNAS, Dec. 1983, vol. 80, No. 23, pp. 7337-7341.
Igakura et al., "Spread of HTLV-I between lymphocytes by virus-induced polarization of the cytoskeleton", Science, Mar. 14, 2003, vol. 299, No. 5613, pp. 1713-1716.
Ito et al., "Expression of facilitative glucose transporter isoforms in lung carcinomas: its relation to histologic type, differentiation grade, and tumor stage", Mod Pathol, May 1998, vol. 11, No. 5, pp. 437-443.
Jassal et al., "Human T-cell leukemia virus type 1 receptor expression among syncytium-resistant cell lines revealed by a novel surface glycoprotein-immunoadhesin", J Virol, Sep. 2001, vol. 75, No. 17, pp. 8317-8328.
Kasahara et al., "Reconstitution and purification of the D-glucose transporter from human erythrocytes", JBC, Oct. 25, 1977, vol. 252, No. 20, pp. 7384-7390.
Kasinrerk et al., "Human leukocyte activation antigen M6, a member of the Ig superfamily, is the species homologue of rat OX-47, mouse basigin, and chicken HT7 molecule", J Immunol, Aug. 1992, vol. 149, No. 3, pp. 847-854.
Kawamura et al., "Expression of glucose transporter-1 in human gastric carcinoma: association with tumor aggressiveness, metastasis, and patient survival", Cancer, 2001, vol. 92, No. 3, pp. 634-641.
Kim et al., "Definition of an amino-terminal domain of the human T-cell leukemia virus type 1 envelope surface unit that extends the fusogenic range of an ecotropic murine leukemia virus", J Biol Chem, Aug. 2000, vol. 275, No. 31, pp. 23417-23420.
Kim et al., "Human T-cell leukemia virus type 1 envelope-mediated syncytium formation can be activated in resistant Mammalian cell lines by a carboxy-terminal truncation of the envelope cytoplasmic domain", J Virol., Jan. 2003, vol. 77, No. 2, pp. 963-969.
Kirk et al., "CD147 is tightly associated with lactate transporters MCT1 and MCT4 and facilitates their cell surface expression", Embo J, Aug. 2000, vol. 19, No. 15, pp. 3896-3904.
Klepper et al., "Facilitated glucose transporter protein type 1 (GLUT1) deficiency syndrome: impaired glucose transport into brain—a review", Eur J Pediatr., Jun. 2002, vol. 161, No. 6, pp. 295-304.
Koralnik et al., "Phylogenetic associations of human and simian T-cell leukemia/lymphotropic virus type I strains: evidence for interspecies transmission", 1994, J Virol., vol. 68, No. 4, pp. 2693-2707.
Korgun et al., "Sustained hypoglycemia affects glucose transporter expression of human blood leukocytes", Blood Cells Mol Dis., Mar.-Apr. 2002, vol. 28, No. 2, pp. 152-159.

(56) References Cited

OTHER PUBLICATIONS

Krauss et al., "Selective inhibition by ethanol of the type 1 facilitative glucose transporter (GLUT1)", 1994, Mol Pharmacol, vol. 45, No. 6, pp. 1281-1286.
Kunkel et al., "Overexpression of Glut-1 and increased glucose metabolism in tumors are associated with a poor prognosis in patients with oral squamous cell carcinoma", Cancer February, 2003, vol. 97, No. 4, pp. 1015-1024.
La Grenade et al., "Childhood dermatitis in the tropics: with special emphasis on infective dermatitis, a marker for infection with human T-cell leukemia virus-I" 1996, Cutis, vol. 58, No. 2, pp. 115-118.
Lachaal et al., "Cadmium increases GLUT1 substrate binding affinity in vitro while reducing its cytochalasin B binding affinity", 1996, Biochemistry, vol. 35, No. 47, pp. 14958-14962.
Loughran et al., "Epitope mapping of HTLV envelope seroreactivity in LGL leukaemia", 1998, Br J Haematol, vol. 101, No. 2, pp. 318-324.
Mahieux et al., "HTLV-3/STLV-3 and HTLV-4 viruses: discovery, epidemiology, serology and molecular aspects", 2011, Viruses, vol. 3, pp. 1074-1090.
Manel et al., The Ubiquitous Glucose Transporter GLUT-1 Is a Receptor for HTLV, Cell, 2003, vol. 115, pp. 449-459.
Martineau et al., "Enhancement of hexose entry into chick fibroblasts by starvation: differential effect on galactose and glucose", Proc Natl Acad Sci USA, Nov. 1972, vol. 69, No. 11, pp. 3407-3411.
May et al., "Photolabeling of the human erythrocyte glucose carrier with androgenic steroids", 1988, Biochim Biophys Acta, vol. 943, No. 2, pp. 199-210.
Miller et al., "Cloning of the cellular receptor for amphotropic murine retroviruses reveals homology to that for gibbon ape leukemia virus", Proc Natl Acad Sci USA, Jan. 1994, vol. 91, No. 1, pp. 78-82.
Mineta et al., "Prognostic value of glucose transporter 1 expression in patients with hypopharyngeal carcinoma", Anticancer Res, Nov.-Dec. 2002, vol. 22, No. 6B, pp. 3489-3494.
Moadel et al., "Positherapy: targeted nuclear therapy of breast cancer with 18F-2-deoxy-2-fluoro-D-glucose", 2005 Cancer Res, vol. 65, No. 3, pp. 698-702.
Mochizuki et al., "FDG uptake and glucose transporter subtype expressions in experimental tumor and inflammation models", J Nucl Med., Oct. 2001, vol. 42, No. 10, pp. 1551-1555.
Mochizuki et al., "HTLV-I uveitis", 1996, J Acquir Immune Defic Syndr Hum Retrovirol, vol. 13, suppl 1, pp. S50-556.
Moriguchi et al., "Decreased mitogen response of splenic lymphocytes in obese Zucker rats is associated with the decreased expression of glucose transporter 1 (GLUT-1)", Am J Clin Nutr., Jun. 1998, vol. 67, No. 6, pp. 1124-1129.
Mueckler, Mike, "Facilitative glucose transporters", Eur J Biochem, Feb. 1994, vol. 219, No. 3, pp. 713-725.
Mueckler et al., "Sequence and structure of a human glucose transporter", Science, Sep. 1985, vol. 229, No. 4717, pp. 941-945.
Nagy et al., "Human T-cell leukemia virus type I: induction of syncytia and inhibition by patients' sera", Int J Cancer, Sep. 15, 1983, vol. 32, No. 3, 321-328.
Nishioka et al., "Human T lymphotropic virus type I in arthropathy and autoimmune disorders", 1996, Arthritis Rheum, vol. 39, No. 8, pp. 1410-1418.
Niyogi et al., "Characterization of new syncytium-inhibiting monoclonal antibodies implicates lipid rafts in human T-cell leukemia virus type 1 syncytium formation", J Virol., Aug. 2001, vol. 75, No. 16, pp. 7351-7361.
Ojeda et al., "Noncompetitive blocking of human GLUT1 hexose transporter by methylxanthines reveals an exofacial regulatory binding site", 2012, Am J Physiol, Cell Physiol, vol. 303, pp. C530-C539.
Osame et al., "HTLV-I associated myelopathy, a new clinical entity", Lancet, May 3, 1986, vol. 1, No. 8488, pp. 1031-1032.
Overbaugh et al., "Receptors and entry cofactors for retroviruses include single and multiple transmembrane-spanning proteins as well as newly described glycophosphatidylinositol-anchored and secreted proteins", Microbiol Mol Biol Rev, Sep. 2001, vol. 65, No. 3, pp. 371-389.
Palayoor et al., "Ibuprofen-mediated reduction of hypoxia-inducible factors HIF-1alpha and HIF-2alpha in prostate cancer cells", Clin Cancer Res., Aug. 1, 2003, vol. 9, No. 8, pp. 3150-3157.
Palker et al., "Purification of envelope glycoproteins of human T cell lymphotropic virus type I (HTLV-I) by affinity chromatography", 1987, J Virol Met, vol. 18, pp. 243-255.
Pankratz et al., "Insulin receptor substrate-2 regulates aerobic glycolysis in mouse mammary tumor cells via glucose transporter 1", 2009, JBC, vol. 284, No. 4, pp. 2031-2037.
Peters, "The energy request of inflammation", Endocrinology, Oct. 2006, vol. 147, No. 10, pp. 4550-4552.
Pinkofsky et al,, "The inhibition of GLUT1 glucose transport and cytochalasin B binding activity by tricyclic antidepressants", 2000, Life Sci, vol. 66, No. 3, pp. 271-278.
Poiesz et al., "Detection and isolation of type C retrovirus particles from fresh and cultured lymphocytes of a patient with cutaneous T-cell lymphoma", Proc Natl Acad Sci U S A, Dec. 1980, vol. 77, No. 12, pp. 7415-7419.
Rathmell et al., "In the absence of extrinsic signals, nutrient utilization by lymphocytes is insufficient to maintain either cell size or viability", Mol Cell, Sep. 2000, vol. 6, No. 3, pp. 683-692.
Reske et al., "Overexpression of glucose transporter 1 and increased FDG uptake in pancreatic carcinoma", 1997, J Nucl Med, vol. 38, No. 9, pp. 1344-1348.
Rodrigues et al., "Modulation of phosphate uptake and amphotropic murine leukemia virus entry by posttranslational modifications of PIT-2", J Virol., May 1999, vol. 73, No. 5, pp. 3789-3799.
Rosenberg et al., "Analysis of functional conservation in the surface and transmembrane glycoprotein subunits of human T-cell leukemia virus type 1 (HTLV-1) and HTLV-2", J Virol, Sep. 1998, vol. 72, No. 9, pp. 7609-7614.
Rumsey et al., "Glucose transporter isoforms GLUT1 and GLUT3 transport dehydroascorbic acid", 1997, J Biol Chem, vol. 272, No. 30, pp. 18982-18999.
Sakashita et al., "Glut1 expression in T1 and T2 stage colorectal carcinomas: its relationship to clinicopathological features", 2001, Eur J Cancer, vol. 37, pp. 204-209.
Slattery et al., "Genomic evolution, patterns of global dissemination, and interspecies transmission of human and simian T-cell leukemia/lymphotropic viruses", Genome Res., Jun. 1999, vol. 9, No. 6, pp. 525-540.
Sutton et al. "Broad host range of human T-cell leukemia virus type 1 demonstrated with an improved pseudotyping system", L Virol., Oct. 1996, vol. 70, No. 10, pp. 7322-7326.
Tokita et al, "Serial changes in 14C-deoxyglucose and 201Tl uptake in autoimmune myocarditis in rats", J Nucl Med., Feb. 2001, vol. 42, No. 2, pp. 285-291.
Zucker-Franklin et al., "Reexamination of human T cell lymphotropic virus (HTLV-I/II) prevalence", 1997, PNAS, vol. 94, No. 12, pp. 6403-6407.
Trejo et al., "The HTlV receptor is a widely expressed protein", Mar. 2000, vol. 268, No. 1, pp. 41-48.
Vannucci et al., "Glucose transporter proteins in brain: delivery of glucose to neurons and glia", 1997, Glia, vol. 21, pp. 2-21.
Vera et al., "Genistein is a natural inhibitor of hexose and dehydroascorbic acid transport through the glucose transporter, GLUT1", 1996, J Biol Chem, vol. 271, No. 15, pp. 8719-8724.
Warburg et al., "On the origin of cancer cells", Science, Feb. 1956, vol. 123, No. 3191, pp. 309-314.
Weiss, Robin A., "HIV receptors and cellular tropism", IUBMB Life, Apr.-May 2002, vol. 53, No. 4-5, pp. 201-205.
Yoshida et al., "Isolation and characterization of retrovirus from cell lines of human adult T-cell leukemia and its implicationin the disease", Proc Natl Acad Sci U S A, Mar. 1982, vol. 79, No. 6, pp. 2031-2035.
Younes et al., "Overexpression of Glut1 and Glut3 in stage I nonsmall cell lung carcinoma is associated with poor survival", Cancer, Sep. 1997, vol. 80, No. 6, pp. 1046-1051.

(56) References Cited

OTHER PUBLICATIONS

Young et al., "Regulation of myocardial glucose uptake and transport during ischemia and energetic stress", 1999, Am J Cardiol., vol. 83, pp. 25H-30H.

Yu et al., "In vitro evidence that cytokine receptor signals are required for differentiation of double positive thymocytes into funtionally mature CD8+ T cells", J Exp Med., Feb. 17, 2003, vol. 197, No. 4, pp. 475-487.

Zeller et al., "Altered glucose transporter mRNA abundance in a rat model of endotoxic shock", Biochem Biophys Res Commun., Apr. 15, 1991, vol. 176, No. 1, pp. 535-540.

Kinet et al. "Isolated receptor binding domains of HTLV-1 and HTLV-2 envelopes bind Glut-1 on activated CD4+ and CD8+ T cells", 2007, Retrovirology, vol. 4, No. 1, pp. 31.

Lavanya et al. "Cell surface expression of the bovine leukemia virus-binding receptor on B and T lymphocytes is induced by receptor engagement", 2008, J. Immunol., vol. 181, No. 2, pp. 891-898.

* cited by examiner

Jurkat T-cell line

GLUT-1 AS A RECEPTOR FOR HTLV ENVELOPES AND ITS USES

FIELD OF INVENTION

The invention relates to the use of the ubiquitous vertebrate glucose transporter GLUT1, or of fragments or sequences derived thereof, for the in vitro diagnosis of cancers, when used as a tumor marker, or for the screening of compounds useful for the preparation of drugs for the prevention or the treatment of pathologies linked to an infection of an individual with a primate T-lymphotropic virus (PTLV), or pathologies linked to an overexpression of GLUT1 on cell surfaces, or the in vitro detection of GLUT1 on cell surfaces. The invention also relates to pharmaceutical compositions containing GLUT1, or fragments or sequences derived thereof, and to their uses such as in the frame of the prevention or the treatment of pathologies linked to an infection of an individual with a PTLV.

The present application also relates to polypeptides derived from the soluble part of the glycoprotein of a Primate T-cell leukemia virus (PTLV), or fragments or variants thereof named receptor binding domain ligands (RBD) selected for their ability to bind specifically to the Glucose Transporter 1 (GLUT1).

BACKGROUND OF INVENTION

The human T-cell leukemia virus (HTLV) is associated with leukemia and neurological syndromes. The role of viral envelopes in HTLV physiopathology is unclear and the envelope receptor, found in all vertebrate cell lines, remains unidentified.

HTLV envelope glycoproteins induce syncytium formation in vitro but their physiopathological effects are unclear. All vertebrate cell lines express functional HTLV envelope receptors, including cells resistant to HTLV envelope-mediated syncytium formation.

The Applicant found that expression of the HTLV receptor-binding domain decreased lactate production due to diminished glucose consumption whereas binding-defective envelope mutants did not alter glucose metabolism. Glucose starvation increased HTLV receptor expression, reminiscent of nutrient sensing responses. Accordingly, overexpression of Glucose Transporter 1 (GLUT1), the ubiquitous vertebrate glucose transporter, specifically increased HTLV envelope binding and GLUT1 colocalized with HTLV envelopes. Moreover, HTLV envelope binding was highest in human erythrocytes, where GLUT1 is abundantly expressed and is the sole glucose transporter isoform.

In the present invention, the Applicant identified specific fragments of PTLV envelope protein that bind to GLUT1.

SUMMARY

The present application relates to an isolated polypeptide wherein said polypeptide is a soluble receptor binding domain (RBD) ligand derived from the soluble part of the glycoprotein of a primate T-lymphotropic virus binding to the Glucose Transporter 1 (GLUT1).

The present application also relates to an isolated polypeptide comprising human T-cell leukemia virus (HTLV) 2.RBD and comprising the amino acid sequence SEQ ID NO: 4 or SEQ ID NO: 5 or SEQ ID NO: 7 or SEQ ID NO: 43 or fragments or variants thereof.

The present application also relates to an isolated polypeptide comprising HTLV1.RBD and comprising the amino acid sequence SEQ ID NO: 9 or SEQ ID NO: 10 or SEQ ID NO: 11 or SEQ ID NO: 13 or SEQ ID NO: 15 or SEQ ID NO: 17 or SEQ ID NO: 19 or SEQ ID NO: 21 or fragments or variants thereof.

The present application also relates to an isolated polypeptide comprising HTLV4.RBD and comprising the amino acid sequence SEQ ID NO: 22 or SEQ ID NO: 23 or SEQ ID NO: 51 or fragments or variants thereof.

The present application also relates to an isolated polypeptide comprising HTLV3.RBD and comprising the amino acid sequence SEQ ID NO: 53 or fragments or variants thereof.

The present application also relates to an isolated polypeptide comprising simian T-cell leukemia virus (STLV) 1.RBD and comprising the amino acid sequence SEQ ID NO: 25 or fragments or variants thereof.

The present application also relates to an isolated polypeptide comprising STLV2.RBD and comprising the amino acid sequence SEQ ID NO: 27 or fragments or variants thereof.

The present application also relates to an isolated polypeptide comprising STLV3.RBD and comprising the amino acid sequence SEQ ID NO: 29 or SEQ ID NO: 55 or fragments or variants thereof.

In one embodiment, the isolated polypeptide further comprises a Tag or being fused to an antibody constant fragment or to a fluorescent protein.

The present application also relates to a composition comprising at least one isolated polypeptide wherein said polypeptide is a soluble receptor binding domain (RBD) ligand derived from the soluble part of the glycoprotein of a primate T-lymphotropic virus binding to the Glucose Transporter 1 (GLUT1).

In one embodiment, the composition is a pharmaceutical composition and further comprises a pharmaceutically acceptable excipient.

In another embodiment, the composition is a medicament.

The present application also relates to a method for diagnosing a GLUT1 related disease comprising:

a) collecting sample from a subject,
b) determining the level of GLUT1 expression at a cell surface using an isolated polypeptide wherein said polypeptide is a soluble receptor binding domain (RBD) ligand derived from the soluble part of the glycoprotein of a primate T-lymphotropic virus binding to the Glucose Transporter 1 (GLUT1), and
c) comparing said level to a reference value.

In one embodiment, the GLUT1 related disease is GLUT1 deficiency syndrome. In another embodiment, the GLUT1 related disease is a cancer disease.

The present application also relates to a kit of parts comprising at least one isolated polypeptide wherein said polypeptide is a soluble receptor binding domain (RBD) ligand derived from the soluble part of the glycoprotein of a primate T-lymphotropic virus binding to the Glucose Transporter 1 (GLUT1).

DEFINITIONS

In the present invention, the following terms have the following meanings:

As used herein; the term "identity", when used in a relationship between the sequences of two or more polypeptides or of two or more DNA sequences, refers to the degree of sequence relatedness between polypeptides or DNA sequences (respectively), as determined by the number of matches between strings of two or more amino acid residues or of two or more nucleotides respectively. "Identity" measures the percent of identical matches between the smaller of two or more sequences with gap alignments (if any) addressed by a particular mathematical model or computer program (i.e., "algorithms"). Identity of related polypeptides or DNA sequences can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988). Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. \2, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

"GLUT1": refers to a nutrient transporter which is a glucose importer expressed by metazoans, in particular by humans, used as receptor by Human T Leukemia viruses (HTLV) in particular. In one embodiment, GLUT1 is human GLUT1 (accession number NP_006507.2, SEQ ID NO: 2) encoded by SEQ ID NO: 1 (accession number NM_006516.2). In one embodiment GLUT1 comprises or consists of an amino acid sequence presenting a sequence identity of at least 70% with SEQ ID NO: 2, preferably a sequence identity of at least 75, 80, 85, 90, 91, 92, 93, 94, 95, 96, 97, 98, 99% or more with SEQ ID NO: 2. In one embodiment GLUT1 is encoded by a nucleotide sequence presenting a sequence identity of at least 70% with SEQ ID NO: 1, preferably a sequence identity of at least 75, 80, 85, 90, 91, 92, 93, 94, 95, 96, 97, 98, 99% or more with SEQ ID NO: 1. In one embodiment, GLUT1 comprises or consists of a fragment of SEQ ID NO: 2, preferably a fragment of at least about 100 amino acids, more preferably of at least about 150, 200, 250, 300, 350, 400 or 450 amino acids.

"Ligand" refers to any substance that forms a complex with a cell surface nutrient transporter. Typical ligands include, but are not limited to, polypeptides and proteins. As used herein, a polypeptide refers to a linear polymer of amino acids (preferably at least 50 amino acids) linked together by peptide bonds. A protein specifically refers to a functional entity formed of one or more polypeptides, and optionally of non-polypeptides cofactors.

"About" preceding a figure means plus or less 10% of the value of said figure.

DETAILED DESCRIPTION

The present application relates to peptides or polypeptides derived from the soluble part of the glycoprotein of a Primate T-cell leukemia virus (PTLV), or fragments or variants thereof, said polypeptides binding specifically to the ubiquitous vertebrate glucose transporter GLUT1 as set forth SEQ ID NO: 2. In one embodiment, said polypeptides are selected for their ability to bind specifically to the ubiquitous vertebrate glucose transporter GLUT1 as set forth SEQ ID NO: 2.

The present application thus relates to isolated polypeptides that are receptor binding domain ligands, wherein said receptor binding domain (RBD) ligands comprise or consist of a part or the totality of a receptor binding domain derived from the soluble part of a glycoprotein of an enveloped virus that binds to the glucose transporter GLUT1.

The term "derived from the soluble part of the glycoprotein of an enveloped virus" means that the ligand is a fragment or a part of a glycoprotein contained in the envelope of a virus and can be obtained, for example, by cloning.

The retroviruses of the invention encode an envelope (Env) glycoprotein present in mature retroviral virions. The Env protein is synthesized in the form of a propeptide, which is cleaved in Golgi apparatus by furine peptidase, resulting in two polypeptides: the transmembrane (TM) and the cell surface (SU) components. The SU domain contains two major subdomains: a domain of interaction with the TM domain and the RBD, the second being liable to interact with host cell membrane receptors.

An example of such envelope is represented in FIG. 6.

In one embodiment, the isolated peptide of the invention comprises the SU domain of the glycoprotein envelope of a virus or a fragment of the SU domain, such as, for example, the RBD.

In another embodiment, the isolated peptide of the invention does not comprise the TM domain of the glycoprotein envelope of a virus. Therefore, in one embodiment of the invention, the isolated peptide of the invention is a soluble peptide, such as, for example, a soluble RBD. As used herein, the term "soluble peptide" refers to a peptide which is not anchored within a membrane, such as, for example, by a transmembrane domain.

The term "glycoprotein" is to be understood as meaning an envelope glycoprotein, a coat glycoprotein or a fusion glycoprotein , wherein the term "glycoprotein" refers to a protein containing oligosaccharide chains covalently attached to polypeptide side-chains.

The term "binds to", "binding to" means that the glycoprotein is liable to recognize the glucose transporter GLUT1 present on the surface of the cell. In one embodiment, a ligand that binds to GLUT1 will thus form a complex with glucose transporter GLUT1, which complex may be detected by a method described herein. This complex can be detected if the ligand has been for example, but not limited to, covalently coupled with a detectable molecule such as an antibody constant fragment (Fc) or a fluorescent compound (e.g. Cyanine dye, Alexa dye, Quantum dye, etc). The complex can also be detected if the ligand has been tagged with different means well known to the person skilled in the art. For example, but without limitation, a tag used with the invention can be a tag selected from the group comprising or consisting of Hemaglutinin Tag, Poly Arginine Tag, Poly Histidine Tage, Myc Tag, Strep Tag, S-Tag, HAT Tag, 3× Flag Tag, Calmodulin-binding peptide Tag, SBP Tag, Chitin binding domain Tag, GST Tag, Maltose-Binding protein Tag, Fluorescent Protein Tag, T7 Tag, V5 Tag and Xpress Tag. The use of the ligand therefore allows on the one hand the identification and detection of the cell surface nutrient transporter depending on the ligand used, and on the other hand the quantification of the complex formed.

Methods for determining and/or quantifying binding of a RBD ligand on GLUT1 on the surface of a cell are well known by the skilled artisan. They include but are not limited to: immunoprecipitation assay, enzyme-linked immunosorbent assay (ELISA), Western blotting, flow cytometry, immunofluorescence or image analysis, for example high content analysis, fluorescence polarization (FP), fluorescence resonance energy transfer (FRET), and surface plasmon resonance (SPR).

In one embodiment, the receptor binding domain ligand containing part or the totality of the RBD can be fused to a fluorescent protein such as GFP, to an antibody constant fragment (such as, for example, Fc fragment from rabbit or from mouse), and/or chemically modified to add a fluorochrome, or a fluorescent compound (e.g. Cyanine dye, Alexa dye, Quantum dye, etc), and/or other tagged protein (e.g. Hemaglutinin Tag, Poly Arginine Tag, Poly Histidine Tage, Myc Tag, Strep Tag, S-Tag, HAT Tag, 3× Flag Tag, Calmodulin-binding peptide Tag, SBP Tag, Chitin binding domain Tag, GST Tag, Maltose-Binding protein Tag, T7 Tag, V5 Tag and Xpress Tag).

RBDs are found, in particular, in glycoproteins of the envelope of viruses, therefore, the receptor binding domain ligand contains the total RBD or a fragment or part of the RBD.

In one embodiment, said virus is selected from the group comprising retroviruses primate T cell leukemia virus (PTLV) selected from human T cell leukemia virus (HTLV) and simian T cell leukemia virus (STLV) which comprise or consist of HTLV-1, HTLV-2, HTLV-3, HTLV-4, STLV-1, STLV-2, STLV-3.

In one embodiment, the soluble receptor binding domain ligand is isolated from the glycoprotein of Human T Leukemia Virus-2, and is herein referred as HTLV2.RBD.

In one embodiment, said HTLV2.RBD comprises or consists of the amino acid sequence SEQ ID NO: 4 or fragments thereof.

In one embodiment, said fragments comprise or consist of amino acids 19 to 224 of SEQ ID NO: 4, or comprise or consist of amino acids 20 to 224 of SEQ ID NO: 4 or comprises or consists of amino acids 21 to 224 of SEQ ID NO: 4.

In one embodiment, said fragments comprise or consist of amino acids 1 to 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222 or 223 of SEQ ID NO: 4.

In another embodiment, said fragments comprise or consist of amino acids 19, 20 or 21 to 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222 or 223 of SEQ ID NO: 4.

In another embodiment, said fragments comprise or consist of SEQ ID NO: 4, encoded by the DNA sequence SEQ ID NO: 3.

In another embodiment, said fragments comprise or consist of amino acids 19, 20 or 21 to 178 of SEQ ID NO: 4.

In one embodiment, said HTLV2.RBD comprises or consists of the amino acid sequence SEQ ID NO: 5 or fragments thereof, encoded by the DNA sequence SEQ ID NO: 6.

In one embodiment, said HTLV2.RBD comprises or consists of the amino acid sequence SEQ ID NO: 7 or fragments thereof.

In one embodiment, said HTLV2.RBD comprises or consists of the amino acid sequence SEQ ID NO: 43 or fragments thereof.

In one embodiment, the soluble receptor binding domain ligand is isolated from the glycoprotein of Human T Leukemia Virus-1, and is herein referred as HTLV1.RBD. In one embodiment, said HTLV1.RBD comprises or consists of the amino acid sequence SEQ ID NO: 9 (encoded by SEQ ID NO: 8) or fragments thereof.

In one embodiment, said HTLV1.RBD comprises or consists of the amino acid sequence SEQ ID NO: 10 or fragments thereof.

In one embodiment, said fragments comprise or consist of amino acids 1 to 183, 184, 185, 186, 187, 188, 189, 190, 191, 192, 193, 194, 195, 196, 197, 198, 199, 200, 201, 202, 203, 204, 205, 206, 207 or 208 of SEQ ID NO: 10.

In one embodiment, said fragments comprise or consist of amino acids 21 to 183, 184, 185, 186, 187, 188, 189, 190, 191, 192, 193, 194, 195, 196, 197, 198, 199, 200, 201, 202, 203, 204, 205, 206, 207 or 208 of SEQ ID NO: 10.

In another embodiment, said fragments comprise or consist in SEQ ID NO: 11 (corresponding to amino acids 1 to 182 of SEQ ID NO: 10).

In one embodiment, said fragments comprise or consist of amino acids 21 to 182 of SEQ ID NO: 10.

In one embodiment, said HTLV1.RBD comprises or consists of the amino acid sequence SEQ ID NO: 11 or fragments thereof.

In one embodiment, said HTLV1.RBD comprises or consists of the amino acid sequence SEQ ID NO: 13 (encoded by SEQ ID NO: 12) or fragments thereof.

In one embodiment, said HTLV1.RBD comprises or consists of the amino acid sequence SEQ ID NO: 15 (encoded by the DNA sequence SEQ ID NO: 14) or fragments thereof.

In one embodiment, said HTLV1.RBD comprises or consists of the amino acid sequence SEQ ID NO: 17 (encoded by the DNA sequence SEQ ID NO: 16) or fragments thereof.

In one embodiment, said HTLV1.RBD comprises or consists of the amino acid sequence SEQ ID NO: 19 (encoded by the DNA sequence SEQ ID NO: 18) or fragments thereof.

In one embodiment, said HTLV1.RBD comprises or consists of the amino acid sequence SEQ ID NO: 21 (encoded by the DNA sequence SEQ ID NO: 20) or fragments thereof.

In one embodiment, the soluble receptor binding domain ligand is isolated from the glycoprotein of Human T Leukemia Virus-4, and is herein referred as HTLV4.RBD. In one embodiment, said HTLV4.RBD comprises or consists of the amino acid sequence SEQ ID NO: 51 or fragments thereof.

In one embodiment, said fragments comprise or consist of amino acids 1 to 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 710, 711, 712, 713, 714, 715, 716, 717, 718, 719, 720, 721, 722, 723, 724, 725, 726, 727, 728, 729, 730, 731, 732, 733, or 734 of SEQ ID NO: 51.

In one embodiment, said fragments comprise or consist of amino acids 24 to 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 710, 711, 712, 713, 714, 715, 716, 717, 718, 719, 720, 721, 722, 723, 724, 725, 726, 727, 728, 729, 730, 731, 732, 733, or 734 of SEQ ID NO: 51.

In another embodiment, said fragments comprise or consist of amino acids 22 to 237 of SEQ ID NO: 51, or comprise or consist of amino acids 23 to 237 of SEQ ID NO: 51, or comprise or consist of amino acids 24 to 237 of SEQ ID NO: 51.

In another embodiment, said fragments comprise or consist of amino acids 1 to 236 of SEQ ID NO: 51. In another embodiment, said fragments comprise or consist of amino acids 24 to 236 of SEQ ID NO: 51.

In another embodiment, said fragments comprise or consist of SEQ ID NO: 51, encoded by the DNA sequence SEQ ID NO: 50.

In one embodiment, said HTLV4.RBD comprises or consists of the amino acid sequence SEQ ID NO: 22 or fragments thereof.

In one embodiment, said fragments comprises or consists of amino acids 1 to 179, 180, 181, 182, 183, 184, 185, 186, 187, 188, 189, 190, 191, 192, 193, 194, 195, 196, 197, 198, 199, 200, 201, 202, 203 or 204 of SEQ ID NO: 22.

In one embodiment, said fragments comprise or consist of amino acids 21 to 179, 180, 181, 182, 183, 184, 185, 186, 187, 188, 189, 190, 191, 192, 193, 194, 195, 196, 197, 198, 199, 200, 201, 202, 203 or 204 of SEQ ID NO: 22.

In another embodiment, said fragments comprise or consist in SEQ ID NO: 23 (corresponding to amino acids 1 to 178 of SEQ ID NO: 22).

In another embodiment, said fragments comprise or consist in amino acids 21 to 178 of SEQ ID NO: 22.

In one embodiment, the soluble receptor binding domain ligand is isolated from the glycoprotein of Human T Leukemia Virus-3, and is herein referred as HTLV3.RBD. In one embodiment, said HTLV3.RBD comprises or consists of the amino acid sequence SEQ ID NO: 53 or fragments thereof.

In one embodiment, said fragments comprises or consists of amino acids 1 to 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, or 492 of SEQ ID NO: 53 or fragments thereof.

In one embodiment, said fragments comprise or consist of amino acids 23 to 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, or 492 of SEQ ID NO: 53 or fragments thereof.

In another embodiment, said fragments comprise or consist of amino acids 1 to 180 of SEQ ID NO: 53. In another embodiment, said fragments comprise or consist of amino acids 23 to 180 of SEQ ID NO: 53.

In another embodiment, said fragments comprise or consist of SEQ ID NO: 53, encoded by the DNA sequence SEQ ID NO: 52.

In one embodiment, the soluble receptor binding domain ligand is isolated from the glycoprotein of Simian T Leukemia Virus-1, and is herein referred as STLV1.RBD. In one embodiment, said STLV1.RBD comprises or consists of the amino acid sequence SEQ ID NO: 25 or fragments thereof.

In one embodiment, said fragments comprises or consists of amino acids 1 to 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, or 487 of SEQ ID NO: 25 or fragments thereof.

In one embodiment, said fragments comprises or consists of amino acids 21 to 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, or 487 of SEQ ID NO: 25 or fragments thereof.

In another embodiment, said fragments comprise or consist of amino acids 1 to 180 of SEQ ID NO: 25. In another embodiment, said fragments comprise or consist of amino acids 21 to 180 of SEQ ID NO: 25.

In another embodiment, said fragments comprise or consist of SEQ ID NO: 25, encoded by the DNA sequence SEQ ID NO: 24.

In one embodiment, the soluble receptor binding domain ligand is isolated from the glycoprotein of Simian T Leukemia Virus-2, and is herein referred as STLV2.RBD. In one embodiment, said STLV2.RBD comprises or consists of the amino acid sequence SEQ ID NO: 27 or fragments thereof.

In one embodiment, said fragments comprises or consists of amino acids 1 to 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, or 486 of SEQ ID NO: 27 or fragments thereof.

In one embodiment, said fragments comprises or consists of amino acids 21 to 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, or 486 of SEQ ID NO: 27 or fragments thereof.

In another embodiment, said fragments comprise or consist of amino acids 1 to 175 of SEQ ID NO: 27. In another embodiment, said fragments comprise or consist of amino acids 21 to 175 of SEQ ID NO: 27.

In another embodiment, said fragments comprise or consist of SEQ ID NO: 27, encoded by the DNA sequence SEQ ID NO: 26.

In one embodiment, the soluble receptor binding domain ligand is isolated from the glycoprotein of Simian T Leukemia Virus-2, and is herein referred as STLV3.RBD. In one embodiment, said STLV3.RBD comprises or consists of the amino acid sequence SEQ ID NO: 55 or fragments thereof.

In one embodiment, said fragments comprises or consists of amino acids 1 to 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 489, 490, or 491 of SEQ ID NO: 55 or fragments thereof.

In one embodiment, said fragments comprises or consists of amino acids 22 to 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 489, 490, or 491 of SEQ ID NO: 55 or fragments thereof.

In another embodiment, said fragments comprise or consist of amino acids 1 to 181 of SEQ ID NO: 55. In another embodiment, said fragments comprise or consist of amino acids 22 to 181 of SEQ ID NO: 55.

In another embodiment, said fragments comprise or consist of SEQ ID NO: 55, encoded by the DNA sequence SEQ ID NO: 54.

In one embodiment, the soluble receptor binding domain ligand is isolated from the glycoprotein of Simian T Leukemia Virus-3, and is herein referred as STLV3.RBD. In one embodiment, said STLV3.RBD comprises or consists of the amino acid sequence SEQ ID NO: 29 or fragments thereof.

In another embodiment, said fragments comprise or consist of SEQ ID NO: 29, encoded by the DNA sequence SEQ ID NO: 28.

In one embodiment, the isolated polypeptides of the invention are selected from the group comprising the sequences SEQ ID NO: 4, 5, 7, 9, 10, 11, 13, 15, 17, 19, 21, 22, 23, 25, 27, 29, 43, 51, 53, and 55 fragments and variants thereof. According to another embodiment, the isolated polypeptides of the invention are encoded by a DNA sequence selected from the group comprising the sequences SEQ ID NO: 3, 6, 8, 12, 14, 16, 18, 20, 24, 26, 28, 50, 52, and 54.

In one embodiment, the isolated polypeptide of the invention comprises or consists of a sequence presenting a sequence identity of at least 70% with one of the sequences SEQ ID NO: 4, 5, 7, 9, 10, 11, 13, 15, 17, 19, 21, 22, 23, 25, 27, 29, 43, 51, 53, and 55, preferably a sequence identity of at least about 75, 80, 85, 90, 91, 92, 93, 94, 95, 96, 97, 98, 99% or more with one of the sequences SEQ ID NO: 4, 5, 7, 9, 10, 11, 13, 15, 17, 19, 21, 22, 23, 25, 27, 29, 43, 51, 53, and 55.

In another embodiment, the isolated polypeptide of the invention is encoded by a DNA sequence presenting a sequence identity of at least 70% with one of the sequences 3, 6, 8, 12, 14, 16, 18, 20, 24, 26, 28, 50, 52 and 54 preferably a sequence identity of at least about 75, 80, 85, 90, 91, 92, 93, 94, 95, 96, 97, 98, 99% or more with one of the sequences SEQ ID NO: 3, 6, 8, 12, 14, 16, 18, 20, 24, 26 28, 50, 52 and 54.

In one embodiment, the isolated polypeptide of the invention is a variant of one of the polypeptide having the sequences SEQ ID NO: 4, 5, 7, 9, 10, 11, 13, 15, 17, 19, 21, 22, 23, 25, 27, 29, 43, 51, 53, and 55.

A polypeptide "variant" as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences and evaluating one or more biological activities of the polypeptide as described herein and/or using any of a number of techniques well known in the art. Modifications may be made in the structure of polypeptides and still obtain a functional molecule that encodes a variant or derivative polypeptide with desirable characteristics.

When it is desired to alter the amino acid sequence of a polypeptide to create an equivalent, or even an improved, variant or portion of a ligand of the invention, one skilled in the art will typically change one or more of the codons of the encoding DNA sequence. For example, certain amino acids may be substituted by other amino acids in a protein structure without appreciable loss of its ability to bind cell surface nutrient transporters. Since it is the binding capacity and nature of a protein that defines that protein's biological functional activity, certain amino acid sequence substitutions can be made in a protein sequence, and, of course, its underlying DNA coding sequence, and nevertheless obtain a protein with similar properties. It is thus contemplated that various changes may be made in the peptide sequences, or corresponding DNA sequences that encode said peptides without appreciable loss of their biological utility or activity. In many instances, a polypeptide variant will contain one or more conservative substitutions. A "conservative substitution" is one in which an amino acid is substituted by another amino acid that has similar properties, such that one skilled in the art of peptide chemistry would expect the secondary structure and hydropathic nature of the polypeptide to be substantially unchanged. As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine. Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of 1, 2, 3, 4, 5, 6, 7, 8, 9 or 10 amino acids. Variants may also (or alternatively) be modified by, for example, the deletion or addition of amino acids that have minimal influence on the immunogenicity, secondary structure and hydropathic nature of the polypeptide.

In one embodiment, the isolated polypeptide of the invention is a fusion protein comprising a part or the totality of a receptor binding domain fused to a detection tag, such as, for example, a Fc fragment or a fluorescent protein such as GFP. Examples of Fc fragments include, but are not limited to, rabbit Fc fragment (amino acid sequence SEQ ID NO: 30, encoded by SEQ ID NO: 31), and mouse Fc fragment (amino acid sequence SEQ ID NO: 32, encoded by SEQ ID NO: 33).

In one embodiment, the isolated polypeptide of the invention is HTLV2.RBD fused to a mouse Fc fragment (encoded by the DNA sequence SEQ ID NO: 34).

In one embodiment, the isolated polypeptide of the invention is obtained by a cloning method, such as, for example, using any production system known in the art, such as, for example, *E. coli*, yeast, baculovirus-insect cell, or mammalian cells such as HEK or CHO, expression system. In one embodiment, the sequence of the receptor binding domain ligand is fused in N-terminal to a peptide signal sequence allowing the secretion of said receptor binding domain ligand. Examples of peptide signal sequences include, but are not limited to, human IL-2 peptide signal (SEQ ID NO: 44), human albumin peptide signal (SEQ ID NO: 45), human chymotrypsinogen peptide signal (SEQ ID NO: 46), human trypsinogen-2 peptide signal (SEQ ID NO: 47), gaussia luciferase peptide signal (SEQ ID NO: 48), and mouse IgM peptide signal (SEQ ID NO: 49).

The present invention also relates to a composition comprising at least one of the isolated polypeptide of the present invention.

The present invention also relates to a pharmaceutical composition comprising at least one of the isolated polypeptide of the invention and at least one pharmaceutically acceptable excipient.

The term "pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The present invention also relates to a medicament, comprising at least one of the isolated polypeptide of the invention, Preferably, the composition, the pharmaceutical composition or the medicament of the invention comprises a therapeutically effective amount of at least one of the isolated polypeptide of the invention.

It will be understood that the total daily usage of at least one of the isolated polypeptide of the invention, composition, pharmaceutical composition and medicament of the present invention will be decided by the attending physician within the scope of sound medical judgment. The specific therapeutically effective dose level for any particular patient will depend upon a variety of factors including the disorder being treated and the severity of the disorder; activity of the specific RBD employed; the specific composition employed, the age, body weight, general health, sex and diet of the patient; the time of administration, route of administration, and rate of excretion of the specific RBD employed; the duration of the treatment; drugs used in combination or coincidental with the specific polypeptide employed; and like factors well known in the medical arts. For example, it is well within the skill of the art to start doses of the RBD at levels lower than those required to achieve the desired therapeutic effect and to gradually increase the dosage until the desired effect is achieved. However, the daily dosage of the products may be varied over a wide range from about 10 to about 10,000 mg per adult per day, preferably 100 to about 5,000, more preferably from about 200 to about 2,000 mg per adult per day. Preferably, the compositions contain 10, 50, 100, 250, 500, 1000 and 2,000 mg of the active ingredient for the symptomatic adjustment of the dosage to the patient to be treated. A medicament typically contains from about 10 to about 10,000 mg of the active ingredient, preferably 100 to about 5,000, more preferably from about 200 to about 2,000 mg of the active ingredient. An effective amount of the drug is ordinarily supplied at a dosage level from 0.1 mg/kg to about 100 mg/kg of body weight per day, preferably from about 1 mg/kg to 40 mg/kg of body weight per day, more preferably from about 2 mg/kg to 20 mg/kg of body weight per day.

In one embodiment, the composition, pharmaceutical composition or medicament comprises sustained-release matrices, such as biodegradable polymers.

In the pharmaceutical compositions of the present invention, the polypeptide of the invention, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the composition, pharmaceutical composition or medicament contains vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising at least one of the isolated polypeptide of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The polypeptide of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the polypeptides in the required amount in the appropriate solvent with one or several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the isolated polypeptide plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion. Some variation in dosage will necessarily occur depending on the condition of the subject being treated.

The person responsible for administration will, in any event, determine the appropriate dose for the individual subject. The at least one isolated polypeptide of the invention may be formulated within a therapeutic mixture to comprise about 10 to 10,000 milligrams, preferably from about 100 to 4,000 milligrams, more preferably from about 200 to 2,000 per dose or so. Multiple doses can also be administered.

In addition, the at least one isolated polypeptide of the invention formulated for parenteral administration, such as intravenous or intramuscular injection, other pharmaceutically acceptable forms include, e.g. tablets or other solids for oral administration; liposomal formulations; time release capsules; and any other form currently used.

In one embodiment, the at least one isolated polypeptide of the invention is topically administered. Examples of formulations adapted to topical administration include, but are not limited to, drops, solutions or topical gels.

In a preferred embodiment, the at least one isolated polypeptide of the invention is systemically administered, such as, for example, orally administered, intranasally administered or injected (including, for example, intraperitoneal, intravenously or intramuscularly injected).

The invention relates to the use of the ubiquitous vertebrate glucose transporter GLUT1 represented by SEQ ID NO: 2, or of fragments or sequences derived thereof, for the in vitro diagnosis of GLUT1 related diseases, such as, for example, cancers (when used as a tumor marker) or GLUT1 deficiency syndrome, or for the screening of compounds useful for the preparation of drugs for the prevention or the treatment of pathologies linked to an infection of an individual with a primate T-lymphotropic virus (PTLV), or pathologies linked to an overexpression or down-expression of GLUT1 on cell surfaces, or the in vitro detection and/or quantification of GLUT1 on cell surfaces.

The present application relates to a method for diagnosing GLUT1 related diseases comprising:

a) collecting sample from a subject,
b) determining the level of GLUT1 expression at a cell surface using the polypeptide of the invention,
c) comparing said level to a reference value.

Examples of sample include, but are not limited to, blood, plasma, serum, cerebrospinal fluid, saliva, lymph, ascetic fluid, cystic fluid, urine, bile, nipple exudate, synovial fluid, bronchoalveolar lavage fluid, sputum, amniotic fluid, chorionic villi, peritoneal fluid, pleural fluid, pericardial fluid, semen, saliva, sweat and alveolar macrophages.

In one embodiment, the sample collected comprises red blood cells, preferably peripheral red blood cells.

In one embodiment, the sample collected is a drop of blood.

Methods for determining a protein expression in a sample are well-known in the art. Examples of such methods include, but are not limited to, Multiplex methods (Luminex), western blot, enzyme-linked immunosorbent assay (ELISA), flow cytometry, sandwich ELISA, fluorescent-linked immunosorbent assay (FLISA), enzyme immunoassay (EIA), radioimmunoassay (RIA) and the like.

As used herein, the term "reference" broadly encompasses any suitable reference expression level which may be used as a basis for comparison with respect to the measured expression level.

In one embodiment, the reference value is a personalized reference, determined earlier in a sample provided by the same subject.

In one embodiment, a reference value can be relative to an expression value derived from population studies, including without limitation, such subjects having similar age range, subjects in the same or similar ethnic group, condition history and the like.

In one embodiment, the reference value is constructed using algorithms and other methods of statistical and structural classification.

In one embodiment of the invention, the reference value is derived from the measurement of the expression value in a control sample derived from one or more substantially healthy subjects, wherein substantially healthy subjects are not affected and/or diagnosed with the GLUT1 related disease.

In another embodiment of the invention, the reference value is derived from the measurement of the expression value of the GLUT1 expression in a reference sample, preferably a reference sample, derived from a reference population.

In one embodiment, the reference population comprises substantially healthy subjects, preferably at least 100, more preferably at least 250, more preferably at least 500 substantially healthy subjects.

In another embodiment, the reference population comprises subjects having a GLUT1 related disease, preferably at least 10, more preferably at least 20, more preferably at least 50, more preferably at least 100, more preferably at least 250, more preferably at least 500 subjects having a GLUT1 related disease.

Examples of GLUT1 related diseases include but are not limited to: Glucose transporter type 1 (GLUT1) deficiency syndrome (DS), and cancer (such as, for example, breast cancer, Adenocarcinoma, Squamous cell carcinoma, Hepatocellular carcinoma, Glioblastoma, Rhabdomyosarcoma, tumor cells, lung cancer, vulvar squamous cell carcinoma, gastric cancer, and esophageal cancer).

Glucose transporter type 1 (GLUT1) deficiency syndrome (DS) is characterized by an encephalopathy marked by childhood epilepsy that is refractory to treatment, deceleration of cranial growth leading to microcephaly, psychomotor retardation, spasticity, ataxia, dysarthria and other paroxysmal neurological phenomena often occurring before meals. Symptoms appear between the age of 1 and 4 months, following a normal birth and gestation. The prevalence is unknown.

Diagnosis is based on the clinical picture and biochemical analysis of the cerebrospinal fluid (CSF). In the majority of cases the disease is associated with de novo mutations in the SLC2A1 gene. GLUT1 DS is transmitted as an autosomal dominant trait and in these cases the affected parent presents with a mild form of the disease.

The biochemical signature of GLUT1 DS is the presence of low glucose level and low lactate concentration in the cerebrospinal fluid (CSF) absence of hypoglycemia.

Other diseases were originally given other names and are now recognized as variants of GLUT1 DS. These include, but are not limited to, mitochondrial diseases, intracranial infection and subarachnoid hemorrhage neuroblastoma because of the opsoclonus-like eye movement abnormalities in early infancy, infantile-onset metabolic encephalopathies, infantile-onset seizures, developmental delay and deceleration of head growth, including chronic hypoglycemic syndromes and disorders of amino acid and organic acid metabolism, Rett syndrome, Angelman syndrome, cerebral palsy.

In one embodiment of the invention, the subject is a male. In another embodiment of the invention, the subject is a female.

In one embodiment, the subject of the invention is a human embryo. In another embodiment, the subject of the invention is a human fetus. In another embodiment, the subject of the invention is a new born child.

In one embodiment of the invention, the subject is a young child. As used herein, the term “young child” refers to a child from 0; 1; 2; 3; 4; 5; 6; 7; 8; 9; 10; 11 months old; 1 year old; 1 year and 3 months old; 1 year and 6 months old; 1 year and 9 months old; 2 years; 2 years and 3 months old; 2 years and 6 months old; 2 years and 9 months old; 3 years old.

In one embodiment of the invention, the subject is a child. The term “child” may refer to subjects aged from 0 to 12, preferably from 3 to 12. More generally, the term child refers to a subject which is not yet an adolescent.

In another embodiment of the invention, the subject is an adolescent. In one embodiment, the term “adolescent” may refer to subjects aged from about 12 to 17, but the skilled artisan will appreciate that the length of adolescence may vary from one individual to another.

In another embodiment, the subject is an adult. In one embodiment, the term “adult” may refer to subjects of more than 17 years old. More generally, the term adult refers to a subject which is no more an adolescent.

In another embodiment, the subject of the invention has risk of developing a cancer described here above. In another embodiment, the subject of the invention has a predisposition of developing a cancer described here above.

In another embodiment, the subject of the invention has risk of developing a GLUT1 DS. In another embodiment, the subject of the invention has a predisposition of developing a GLUT1 DS. In one embodiment, said subject presents a familial history of GLUT1 DS.

The expression “determining and/or detecting and/or quantifying the binding of a ligand, such as, for example, a receptor binding domain ligand, to GLUT1” means that when GLUT1 is present a complex is formed between GLUT1 and the ligand. This complex can be detected if the ligand has been for example, but not limited to, covalently coupled with a detectable molecule such as an antibody constant fragment (Fc) or a fluorescent ligand (e.g. Cyanine dye, Alexa dye, Quantum dye, etc). The complex can also be detected if the ligand has been tagged with different means well known to the person skilled in the art. For example, but without limitation, a tag used with the invention can be a tag selected from the group comprising or consisting of fluorescent proteins such as GFP, Hemaglutinin Tag, Poly Arginine Tag, Poly Histidine Tage, Myc Tag, Strep Tag, S-Tag, HAT Tag, 3× Flag Tag, Calmodulin-binding peptide Tag, SBP Tag, Chitin binding domain Tag, GST Tag, Maltose-Binding protein Tag, Fluorescent Protein Tag, T7 Tag, V5 Tag and Xpress Tag.

In one embodiment, determining and/or detecting and/or quantifying binding is conducted by flow cytometry, immunofluorescence or image analysis, for example high content analysis.

For illustration purpose, the polypeptide of the invention can be selected for its ability to bind specifically to said GLUT1, or fragments of GLUT1, according to the following method using a EGFP-tagged GLUT1-binding component derived from PTLV RBD (receptor binding domain) as an example of such polypeptide that is able to bind to GLUT1.

A EGFP-tagged Glut1-binding component derived from PTLV RBD is applied onto live or fixed suspension or attached cells. After washes with appropriate buffer, cells are incubated for 30 min at RT, washed and analyzed or quantified as attached on an appropriate support on a fluorescent microscope or as individual cell suspension on a fluorescent analysis cell sorter (FACS). Alternatively, a non-fluorescent GLUT1-binding component derived from PTLV RBD is applied as described above and revealed with a secondary fluorochrome-tagged reagent such as a fluorochrome-tagged secondary antibody directed against the PTLV RBD or against a non fluorochrome tag attached to the said PTLV RBD component.

The invention relates more particularly to the use as defined above, of fragments of GLUT1 chosen among the followings:

```
SEQ ID NO: 35: NAPQKVIEEFY
SEQ ID NO: 36: NQTWVHRYGESILPTTLTTLWS
SEQ ID NO: 37: KSFEMLILGR
SEQ ID NO: 38: DSIMGNKDL
SEQ ID NO: 39: YSTSIFEKAGVQQP
SEQ ID NO: 40: EQLPWMSYLS
SEQ ID NO: 41: QYVEQLC
SEQ ID NO: 42: IVGMCFQYVEQLC
```

These fragments of GLUT1 correspond to the predicted extracellular loops of human GLUT1 as described by Mueckler, M., and C. Makepeace. 1997. Identification of an amino acid residue that lies between the exofacial vestibule and exofacial substrate-binding site of the GLUT1 sugar permeation pathway. J Biol. Chem. 272(48):30141-6.

The invention also relates to the use of an isolated polypeptide of the invention, for the preparation of drugs for the prevention or the treatment of pathologies linked to an overexpression of GLUT1 on cell surfaces, such as:

- cancers, such as:
  - squamous cell carcinoma (Kunkel M, Reichert T E, Benz P, Lehr H A, Jeong J H, Wieand S, Bartenstein P, Wagner W, Whiteside T L. Cancer. 2003 Feb. 15; 97(4):1015-24),
  - hypopharyngeal carcinoma (Mineta H, Miura K, Takebayashi S, Misawa K, Araki K, Misawa Y, Ueda Y. Anticancer Res. 2002 November-December; 22(6B): 3489-94),
  - breast cancer (Brown R S, Wahl R L. Overexpression of Glut-1 glucose transporter in human breast cancer. An immunohistochemical study. Cancer. 1993 Nov. 15; 72(10):2979-85),
  - cervical carinoma (Mendez L E, Manci N, Cantuaria G, Gomez-Marin O, Penalver M, Braunschweiger P, Nadji M. Expression of glucose transporter-1 in cervical cancer and its precursors. Gynecol Oncol. 2002 August; 86(2):138-43),
  - ovarian carcinoma (Cantuaria G, Fagotti A, Fernandina G, Magalhaes A, Nadji M, Angioli R, Penalver M, Mancuso S, Scambia G. GLUT-1 expression in ovarian carcinoma: association with survival and response to chemotherapy. Cancer. 2001 Sep. 1; 92(5):1144-50),
  - lung cancer (Ito T, Noguchi Y, Satoh S, Hayashi H, Inayama Y, Kitamura H. Expression of facilitative glucose transporter isoforms in lung carcinomas: its relation to histologic type, differentiation grade, and tumor stage. Mod Pathol. 1998 May; 11(5):437-43. Younes M, Brown R W, Stephenson M, Gondo M, Cagle P T. Overexpression of Glut1 and Glut3 in stage I nonsmall cell lung carcinoma is associated with poor survival. Cancer. 1997 Sep. 15; 80(6): 1046-51), pancreatic cancer (Reske S N, Grillenberger K G, Glatting G, Port M, Hildebrandt M, Gansauge F, Beger H G. Overexpression of glucose transporter 1 and increased FDG uptake in pancreatic carcinoma. J Nucl Med. 1997 September; 38(9):1344-8), insulinoma (1: Boden G, Murer E, Mozzoli M. Glucose transporter proteins in human insulinoma. Ann Intern Med. 1994 Jul. 15; 121(2):109-12, inflammatory conditions, immune or auto-immune diseases, such as:

autoimmune myocarditis (Tokita N, Hasegawa S, Tsujimura E, Yutani K, Izumi T, Nishimura T. Serial changes in 14C-deoxyglucose and 201T1 uptake in autoimmune myocarditis in rats. J Nucl Med. 2001 February; 42(2):285-91), in the frame of CD28 T-cell activation (Frauwirth K A, Riley J L, Harris M H, Parry R V, Rathmell J C, Plas D R, Elstrom R L, June C H, Thompson C B. The CD28 signaling pathway regulates glucose metabolism. Immunity. 2002 June; 16(6):769-77), in the frame of immunomodulation (Moriguchi S, Kato M, Sakai K, Yamamoto S, Shimizu E. Decreased mitogen response of splenic lymphocytes in obese Zucker rats is associated with the decreased expression of glucose transporter 1 (GLUT-1). Am J Clin Nutr. 1998 June; 67(6):1124-9), Disorders of the central nervous system, such as facilitated glucose transporter protein type 1 (GLUT1) deficiency syndrome (review in Keppler J, Voit T, Eur J. Pediatr. 2002 June; 161(6):295-304.)

The invention relates more particularly to the use for the preparation of drugs for the prevention or the treatment of pathologies linked to an overexpression of GLUT1 on cell surfaces, of compounds chosen among the followings:

polypeptides compounds corresponding to the envelope proteins of PTLV, or fragments or sequences derived thereof, said fragments or derived sequences being able to bind to GLUT1, glucose or derivatives such as galactose, 2-fluorodeoxyglucose, 2-deoxyglucose, 3-O-methylglucose androgenic steroids, cytochalasin B, forskolin, dipyridamole, isobutylmethylxanthine, ethanol, genistein, cadmium, barbiturate, dehydroascorbic acid, tricyclic antidepressants, oestradiol, anti-oestrogens, faslodex (ICI 182780), tamoxifen, gamma agonists of peroxisome proliferator-activated receptors (PPAR) such as thiazolidinedione, troglitazone, pioglitazone, rosiglitazone, as mentioned above.

The invention relates more particularly to the use of polypeptides corresponding to the envelope proteins of PTLV, or fragments or sequences derived thereof, said polypeptides being selected for their ability to bind specifically to the ubiquitous vertebrate glucose transporter GLUT1 represented by SEQ ID NO: 2, or of nucleotide sequences encoding said polypeptides, for the preparation of drugs for the prevention or the treatment of pathologies linked to an overexpression of GLUT1 on cell surfaces, and the in vitro diagnosis of said pathologies.

The invention relates more particularly to the use as defined above, of polypeptides able to bind to at least one of the above mentioned fragments of GLUT1 corresponding to SEQ ID NO: 35, SEQ ID NO: 36, SEQ ID NO: 37, SEQ ID NO: 38, SEQ ID NO: 39, SEQ ID NO: 40, SEQ ID NO: 41, and SEQ ID NO: 42.

The invention relates more particularly to the use as defined above, of polypeptides able to bind to at least the fragment of GLUT1 corresponding to SEQ ID NO: 42.

The invention relates more particularly to the use as defined above, of GLUT1 binding polypeptides mentioned above chosen among the followings:

the envelope protein of HTLV-1 set forth by SEQ ID NO: 9, or of HTLV-2 forth by SEQ ID NO: 43, or of HTLV-3 forth by SEQ ID NO: 53, or of HTLV-4 forth by SEQ ID NO: 22, or of HTLV-4 forth by SEQ ID NO: 51 or of STLV-1 forth by SEQ ID NO: 25, or of STLV-2 forth by SEQ ID NO: 27, or of STLV-3 forth by SEQ ID NO: 29, or of STLV-3 forth by SEQ ID NO: 55, fragments of the envelope proteins of PTLV, said fragments being polypeptides delimited in their N-terminal extremity by the amino acid located in position 1 to 90, or in position 75 to 90, and in their C-terminal extremity by the amino acid located in position 135 to 245, or in position 135 to 150, of said envelope proteins of PTLV, forth by SEQ ID NO: 43, 9, 25, 27, 29, 23, sequences of HTLV-1.RBD set forth by SEQ ID NO: 9, 10, 11, 13, 15, 17, 19 or 21, or of HTLV-2.RBD set forth by SEQ ID NO: 4, 5, 7, 9 or 43, or of HTLV-3.RBD set forth by SEQ ID NO: 53, or of HTLV-4.RBD set forth by SEQ ID NO: 22 or 51, or of STLV-1.RBD set forth by SEQ ID NO: 25, or of STLV-2.RBD set forth by SEQ ID NO: 27, or of STLV-3.RBD forth by SEQ ID NO: 29 or 55, fragments of the envelope proteins of PTLV, said fragments corresponding to the following polypeptides:

the polypeptide delimited in its N-terminal extremity by the amino acid located in position 83 to 89, and in its C-terminal extremity by the amino acid located in position 139 to 145, of the envelope protein of the strain MT-2 of HTLV-1 forth by SEQ ID NO: 9, the polypeptide delimited in its N-terminal extremity by the amino acid located in position 79 to 85, and in its C-terminal extremity by the amino acid located in position 135 to 141, of the envelope protein of the strain NRA of HTLV-2 forth by SEQ ID NO: 43, the polypeptide delimited in its N-terminal extremity by the amino acid located in position 83 to 89, and in its C-terminal extremity by the amino acid located in position 139 to 145, of the envelope protein of STLV-1 forth by SEQ ID NO: 25, the polypeptide delimited in its N-terminal extremity by the amino acid located in position 79 to 85, and in its C-terminal extremity by the amino acid located in position 135 to 141, of the envelope protein of STLV-2 forth by SEQ ID NO: 27, the polypeptide delimited in its N-terminal extremity by the amino acid located in position 82 to 88, and in its C-terminal extremity by the amino acid located in position 138 to 144, of the envelope protein of STLV-3 forth by SEQ ID NO: 29, the polypeptide corresponding to the envelope protein of a variant of HTLV-1, said polypeptide having the following sequence SEQ ID NO: 13, I K K P N P N G G G Y Y L A S Y S D P C S L K C P Y L G C Q S W T C P Y T G A V S S P Y K F Q Q D V the polypeptide corresponding to the envelope protein of a variant of HTLV-1, said polypeptide having the following sequence SEQ ID NO: 15, V K K P N R N G G G Y Y L A S Y S D P C S L K C P Y L G C Q S W T C P Y T G A V S S P Y W K F Q Q D V the polypeptide corresponding to the envelope protein of a variant of HTLV-1, said polypeptide having the following sequence SEQ ID NO: 17, I K K P N R N G G G Y Y L A S Y S D P C S L K C P Y L G C Q S W T C P Y T G A V S S P Y W K F Q Q D V the polypeptide corresponding to the envelope protein of a variant of HTLV-1, said polypeptide having the following sequence SEQ ID NO: 19, I K K P N R N G G G Y Y L A S Y S D P C S L K C P Y L G C Q S W T C P Y T G P V S S P Y W K F Q Q D V the polypeptide corresponding to the envelope protein of a variant of HTLV-1, said polypeptide having the following sequence SEQ ID NO: 21, I K K P N R N G G G Y H S A S Y S D P C S L K C P Y L G C Q S W T C P Y A G A V S S P Y W K F Q Q D V N F T Q E V the polypeptide corresponding to the envelope protein of a variant of HTLV-2, said polypeptide having the following sequence SEQ ID NO: 7, I R K P N R Q G L G Y Y S P S Y N D P C S L Q C P Y L G S Q S W T C P Y T A P V S T P S W N F H S D V.

The invention relates more particularly to the use of mentioned above of GLUT1 binding polypeptides as defined above, characterized in that the treated or detected pathologies are the followings:

solid tumors, such as brain tumors, squamous cell carcinoma, hypopharyngeal carcinoma, breast cancer, cervical carcinoma, ovarian carcinoma, pancreatic cancer, insulinoma, inflammatory conditions, such as multiple sclerosis, rheumatoid arthritis, immune or auto-immune diseases, such as autoimmune myocarditis, or in the frame of CD28 T-cell activation, or in the frame of immunomodulation, or systemic lupus erythematous, disorders of the central nervous system, such as facilitated glucose transporter protein type 1 (GLUT1) deficiency syndrome.

The invention relates more particularly to the use of polypeptides selected for their ability to bind specifically to GLUT1 as mentioned above, and more particularly GLUT1 binding polypeptides as defined above, for the in vitro detection of GLUT1 on cell surfaces in the frame of processes for the in vitro diagnosis of pathologies linked to an overexpression or down-expression of GLUT1 on cell surfaces, such as pathologies defined above, said processes comprising the following steps:

contacting a biological sample (such as biopsies or cells or tissue manifesting or with a suspected aberrant GLUT1 expression profile) from an individual with at least one polypeptide of the invention, said at least one polypeptide being optionally labeled, or susceptible to be recognized by a labeled molecule, determining the level of said at least one polypeptide bound to the cells contained in the biological sample and comparison with the level of binding of said compound to cells contained in the biological sample from an healthy individual.

The invention relates more particularly to the use of polypeptides as defined above for the in vitro diagnosis of cancers or of GLUT1 DS, characterized in that the polypeptides used are chosen among the polypeptides defined above selected for their ability to bind specifically to GLUT1.

The invention relates more particularly to the use as defined above, of GLUT1 binding polypeptides, or of nucleotide sequences encoding said polypeptides, for the preparation of drug vectors containing at their surface said polypeptides, said vectors being useful for targeting GLUT1 overexpressing cells for the prevention or the treatment of pathologies linked to an overexpression of GLUT1 on cell surfaces, said vectors containing molecules active against said pathologies, or containing genes in the frame of gene therapy of these pathologies.

The invention relates more particularly to the use as defined above, of GLUT1 binding polypeptides, or of nucleotide sequences encoding said polypeptides, for the preparation of drug vectors containing at their surface GLUT1 binding polypeptides, said vectors being useful for targeting GLUT1 overexpressing tumor cells, or cells involved in the inflammatory mechanism, or activated cells of the immune system, or cells of the central nervous system, for the prevention or the treatment of related pathologies as defined above.

The invention concerns more particularly the use of GLUT1 binding polypeptides, or of nucleotide sequences encoding said polypeptides, for the preparation of drug vectors as defined above, wherein the molecules active against the pathologies are antitumor molecules, or molecules against inflammatory conditions, immune or autoimmune diseases, or disorders of the central nervous system.

The invention also relates to the use of nucleotide sequences encoding polypeptides compounds selected for their ability to bind specifically to GLUT1 as defined above, such as nucleotide sequences encoding the polypeptides defined above, or fragments thereof, for the preparation, by substitution of one or several nucleotides of said nucleotide sequences, of mutant nucleotide sequences encoding corresponding mutant polypeptides unable to bind to GLUT1.

The invention also relates to the use of mutant polypeptides unable to bind to GLUT1 as defined above:

as a negative control in the frame of the screening of compounds able to bind specifically to the non mutated corresponding polypeptides, and thus liable to be used in the frame of the preparation of drugs for the prevention or the treatment of pathologies linked to an infection of an individual with a PTLV, for the preparation of drugs for the prevention or the treatment of pathologies linked to an infection of an individual with a PTLV.

The invention relates more particularly to the use as defined above, of mutant polypeptides corresponding to the polypeptides defined above, wherein:

D in position 106 and/or Y in position 114 of the envelope protein of HTLV-1 corresponding to SEQ ID NO: 9, D in position 102 and/or Y in position 110 or of HTLV-2 corresponding to SEQ ID NO: 43, D in position 106 and/or Y in position 114 or of STLV-1 corresponding to SEQ ID NO: 25, D in position 102 and/or Y in position 110 or of STLV-2 corresponding to SEQ ID NO: 27, D in position 105 and/or Y in position 113 or of STLV-3 corresponding to SEQ ID NO: 29, D in position 18 and/or Y in position 26 of the polypeptides corresponding to SEQ ID NO: 13, 15, 17, 19, 21, and 7, are substituted by another amino acid, natural or not, such as mutant polypeptides corresponding to the polypeptides mentioned above wherein said D and/or A residues are substituted by A.

The invention also relates to the use of mutant nucleotide sequences encoding corresponding mutant polypeptides unable to bind to GLUT1 as defined above, for the preparation of transgenic mammal cells expressing said mutant polypeptides, said cells having a negative transdominant effect with regard to PTLV, thus preventing infection and dissemination of this latter in the organism.

The invention also relates to pharmaceutical compositions containing GLUT1 represented by SEQ ID NO: 2, or fragments or sequences derived thereof, said fragments or derived sequences being able to bind to the envelope proteins of the primate T-cell leukemia viruses (PTLV), in association with a pharmaceutically acceptable carrier.

The invention relates more particularly to pharmaceutical compositions containing mutant polypeptides corresponding to the polypeptides defined above, wherein:

- D in position 106 and/or Y in position 114 of the envelope protein of HTLV-1 corresponding to SEQ ID NO: 9,
- D in position 102 and/or Y in position 110 or of HTLV-2 corresponding to SEQ ID NO: 7,
- D in position 105 and/or Y in position 113 or of STLV-3 corresponding to SEQ ID NO: 29,
- D in position 18 and/or Y in position 26, of the polypeptides corresponding to SEQ ID NO: 13, 15, 17, 19, 21, and 7, are substituted by another amino acid, natural or not, such as mutant polypeptides corresponding to the polypeptides mentioned above wherein said D and/or A residues are substituted by A, in association with a pharmaceutically acceptable carrier.

The invention also relates to transgenic mammal cells expressing mutant polypeptides unable to bind to GLUT1 as defined above, said cells having a negative transdominant effect with regard to PTLV, thus preventing infection and dissemination of this latter in the organism.

The invention relates more particularly to pharmaceutical compositions containing transgenic mammal cells as defined above, in association with a pharmaceutically acceptable carrier.

The invention also relates to therapeutic vectors useful for targeting GLUT1 overexpressing cells in pathologies linked to an overexpression of GLUT1 on cell surfaces, such as defined above, said vectors containing at their surface GLUT1 binding polypeptides chosen among those defined above, and containing molecules active against said pathologies, as defined above, or containing genes in the frame of gene therapy.

The invention relates more particularly to pharmaceutical compositions containing therapeutic vectors as described above, in association with a pharmaceutically acceptable carrier.

The invention also relates to a method for the screening of compounds useful for:

- the preparation of drugs for the prevention or the treatment of pathologies linked to an infection of an individual with a PTLV,
- the preparation of drugs for the prevention or the treatment of pathologies linked to an overexpression or to a down-expression of GLUT1 on cell surfaces,
- the in vitro detection of GLUT1 on cell surfaces, said method comprising:

- the contacting of GLUT1 represented by SEQ ID NO: 2, or of fragments or sequences derived thereof, said fragments or derived sequences being able to bind to the envelope proteins of the primate T-cell leukemia viruses (PTLV), or of cells expressing GLUT1, with compounds to be tested,
- the selection of compounds able to bind specifically to GLUT1, or fragments or sequences derived thereof, as for example according to the method mentioned above.

The invention relates more particularly to a method for the screening of compounds useful for the prevention or the treatment of pathologies linked to an overexpression of GLUT1 on cell surfaces, and the in vitro diagnosis of said pathologies, comprising the steps described above:

The invention also relates to a method for the in vitro diagnosis pathologies linked to an overexpression of GLUT1 on cell surfaces, characterized in that it comprises:

- contacting a biological sample (such as biopsies or cells or tissue manifesting or with a suspected aberrant GLUT1 expression profile) from an individual with at least one polypeptide of the invention, said at least one polypeptide being optionally labeled, or susceptible to be recognized by a labeled molecule,
- determining the level of said at least one polypeptide bound to the cells contained in the biological sample and comparison with the level of binding of said at least one polypeptide to cells contained in the biological sample from an healthy individual.

The invention also relates to a method for the in vitro diagnosis pathologies linked to a down-expression of GLUT1 on cell surfaces (such as, for example, GLUT1 DS), characterized in that it comprises:

- contacting a biological sample (such as biopsies or cells or tissue manifesting or with a suspected aberrant GLUT1 expression profile) from an individual with at least one polypeptide of the invention, said at least one polypeptide being optionally labeled, or susceptible to be recognized by a labeled molecule,
- determining the level of said at least one polypeptide bound to the cells contained in the biological sample and comparison with the level of binding of said at least one polypeptide to cells contained in the sample from an healthy individual.

The invention relates more particularly to a method as defined above for the in vitro diagnosis of pathologies mentioned above.

The invention also relates to a kit for research use or for in vitro diagnosis, such as for example in vitro diagnosis of pathologies linked to an overexpression of GLUT1 on cell surfaces as described above, comprising at least one polypeptide of the invention as defined above, said at least one polypeptide being optionally labeled, and, if necessary reagents for the detection of the binding of said at least one polypeptide to GLUT1 initially present on cell surfaces in the biological sample.

The invention also relates to a kit for the in vitro diagnosis of pathologies linked to an down-expression of GLUT1 on cell surfaces as described above, comprising at least one polypeptide of the invention as defined above, said at least one polypeptide being optionally labeled, and, if necessary reagents for the detection of the binding of said at least one polypeptide to GLUT1 initially present on cell surfaces in the biological sample.

The present invention also relates to a kit of parts for detecting and/or determining the expression level of GLUT1 nutrient transporter on the cell surface, comprising at least one polypeptide of the invention.

The present invention also relates to a kit of parts for detecting and/or quantifying the binding of the RBD ligand of the present invention to GLUT1 nutrient transporter, comprising at least one polypeptide of the invention.

In one embodiment, the expression level of GLUT1 nutrient transporter is assessed at the protein level, and the kit of the invention may further comprises means for detecting the expression level of at least one normalization protein.

The present invention also relates to a kit of parts for diagnosing a disease related to GLUT1, comprising at least one polypeptide of the invention or a composition comprising at least one polypeptide of the invention.

In one embodiment, the kit comprises other elements, such as, for example, instructions for use; vials, containers or other storage vessels containing each of the unit doses; delivery devices such as needles, catheters, syringes, tubing and the like; and/or packaging suitable for safely and conveniently storing and/or transporting the kit. Preferably the instructions for use are a label or package insert, wherein the label or package insert indicates that the composition of the invention.

A "package insert" refers to instructions included in commercial packages of the compositions, that contains information about the indications, usage, dosage, administration, contraindications and/or warnings concerning the use of such compositions.

For the purposes herein, a "vial" refers to a container which holds the composition of the invention. The vial may be sealed by a stopper pierceable by a syringe. Generally, the vial is formed from a glass material.

The composition in the vial can be in various states including liquid, lyophilized, frozen etc. The fixed dosage composition is preferably stable as a liquid. Stability may be measured by any means known in the art, although turbidity is a preferred measure. Turbidity level of below about 10, 15, 20, or 30 Nephelometric Turbidity Unit (NTU) can generally be considered a stable fixed dosage composition. Turbidity measurements can be taken by incubating the fixed dosage compositions over time periods such as 0 h, 2 h, 4 h, 6 h, 12 h, 18 h, 24 h, 36 h, 72 h, 7 days and 14 days at storage temperatures such as room temperature or 37° C. Preferably the fixed dosage composition is considered to be stable as a liquid when it is stored for 14 days at room temperature and exhibits a turbidity of less than about 15 NTU.

The invention is further illustrated with the detailed description hereafter of the determination of GLUT1 as a specific receptor for PTLV RBD.

The human T-cell leukemia virus (HTLV) type 1 and 2 are present in all areas of the world as endemic or sporadic infectious agents [Slattery, 1999]. The etiological role of HTLV-1 in adult T cell leukemia (ATL) and tropical spastic paraparesis/HTLV-associated myelopathy (TSP/HAM) has been well established [Poiesz, 1980; Yoshida, 1982; Gessain, 1985; Osame, 1986]. The apparently restricted tropism of HTLV to T lymphocytes in infected patients [Cavrois, 1996; Hanon, 2000] contrasts with the ability of the viral-encoded envelope glycoprotein (Env) to bind to and direct entry into all vertebrate cell types tested in vitro [Sutton, 1996; Trejo, 2000; Kim, 2003]. Retroviral infections depend on early interactions between Env and cellular receptors. Identification of cellular receptors and coreceptors for other retroviral envelopes have helped to elucidate certain aspects of retrovirus physiopathology as well as their transmission and spreading within organisms and populations [Berger, 1999; Clapham, 2001; Weiss, 2002]. However, no clear association between HTLV Env and HTLV-associated diseases has been established and the identity of the receptor(s) for HTLV-1 and HTLV-2 Env has remained elusive.

Numerous cell surface components have been shown to play a role in HTLV Env-mediated syncytia formation [Niyogi, 2001; Daenke, 1999; Hildreth, 1997]. Nevertheless, HTLV Env-dependent cell membrane fusion and syncytia formation appear to be distinct from receptor binding per se [Denesvre, 1996; Daenke, 2000; Kim, 2000; Kim, 2003]. The search for HTLV Env receptor has been hindered in part by its ubiquitous presence [Sutton, 1996; Trejo, 2000; Jassal, 2001; Kim, 2003]. Additionally, the induction of rampant syncytium formation in cell culture upon expression of HTLV Env [Hoshino, 1983; Nagy, 1983] has prevented efficient and persistent Env expression. Based on our observation that the HTLV Env amino terminal domain shares striking structural and functional homology with that of murine leukemia viruses (MLV), we defined HTLV Env receptor-binding domain (RBD) and derived HTLV Env-based tools that overcome the problem of syncytia formation [Kim, 2000; Kim, 2003].

We were thus able to follow specific interactions between the Env RBD and a primary HTLV receptor. Using these tools, we have previously shown that the HTLV receptor is expressed on the surface on T lymphocytes, the major HTLV reservoir in vivo, only following T cell receptor activation [Manel, 2003].

Here we describe striking metabolic alterations in cell cultures following expression of HTLV envelopes as well as HTLV receptor binding domains. These alterations are characterized by a defect in the acidification of the cell culture medium associated with a decreased lactate production and a decline in glucose consumption and uptake. These observations as well as the knowledge that Env receptors for the related MLV and most of the gammaretrovirus belong to the family of multiple-membrane spanning transporters [Overbaugh, 2001] prompted us to test ubiquitous lactate and glucose transport-associated molecules as receptors for HTLV Env. We show that the ubiquitous GLUT-1 glucose transporter, present in all vertebrates, is an essential and specific component of the receptor for HTLV. Moreover, interaction of GLUT-1 with the entire HTLV-1 and HTLV-2 envelopes as well as the truncated HTLV-1 and HTLV-2 RBDs alters glucose metabolism.

BRIEF DESCRIPTION OF THE DRAWINGS

FIG. 1*a*, Medium acidification and syncytia formation in 293T cells one day post-transfection with control DNA or Env expression vectors, including syncytial wild-type HTLV-1 Env and HTLV-2 Env, a non-syncytial chimeric $H_{183}$FEnv, and syncytial A-MLV AR Env. FIG. 1*b*, Extracellular lactate and glucose in the culture medium of 293T cells were measured two days following transfection with an irrelevant DNA (control), F-MLV Env, $H_{183}$FEnv, HTLV-1 RBD ($H1_{RBD}$) or amphotropic MLV RBD ($A_{RBD}$) expression vectors. Lactate and glucose concentrations were normalized to cellular protein content. FIG. 1*c*, 2-deoxyglucose and fructose uptake following transfection of 293T with an irrelevant DNA (control), $H1_{RBD}$, $H2_{RBD}$ or $A_{RBD}$ expression vectors. Control cells were also incubated with glucose transporter inhibitors cytochalasin and phloretin. Data are the means of triplicate measures and are representative of two to three independent experiments. FIG. 1*d*, Expression of the HTLV and amphotropic-MLV receptors on 293T (1) and Jurkat T (2) cells cultured overnight in the presence or absence of glucose was monitored by binding of $H1_{RBD}$ and $A_{RBD}$, respectively.

FIGS. 2*a* and 2*b* HTLV receptor properties correlate with GLUT1 properties. FIG. 2*a*, Expression of the HTLV and amphotropic-MLV receptors at the surface of human and murine erythrocytes, as well as human primary hepatocytes. FIG. 2*b*, $H1_{RBD}$ and $A_{RBD}$ binding to Jurkat cells in the absence or presence of the Glut-1 inhibitor cytochalasin B.

FIG. 3*a*, Expression of $H1_{RBD}$ and the derived mutants D106A and Y114A was monitored by Western blot analysis of the supernatants of 293T cells following transfection with the various expression plasmids. FIG. 3*b*, Binding of $H1_{RBD}$ and the D106A and Y114A mutants to the HTLV receptor on HeLa cells. FIG. 3*c*, Extracellular lactate in the medium of 293T cells one day post transfection with an irrelevant DNA (control), $H1_{RBD}$ or the $H1_{RBD}$ D106A and Y114A mutants. Data are representative of three independent experiments.

FIG. 4*a, Binding of* $H1_{RBD}$, $H2_{RBD}$, $H2_{RBD}$ D102A mutant, and $A_{RBD}$ to control 293T cells or 293T cells overexpressing either GLUT-1 or PiT2. FIG. 4*b*, Binding of $H2_{RBD}$-EGFP to cells overexpressing GLUT-1-HA or GLUT-3-HA, and corresponding immunoblots using an anti-HA antibody. FIG. 4*c*, Immunoprecipitation of GLUT-1-HA from 293T cells transfected with either an irrelevant construct, GLUT-1 alone, H1RBD alone, H1RBD Y114A alone, GLUT-1 with $H1_{RBD}$ or GLUT-1 with $H1_{RBD}$ Y114A expression vectors Immunoprecipitation was performed using anti-rabbit-Fc beads and probed with an anti-HA antibody. Total cell extracts were blotted using an anti-rabbit Fc or an anti-HA antibody.

EXAMPLES

The present invention is further illustrated by the following examples.

Example 1

HTLV Envelopes Alter Lactate Metabolism

Figure 1:
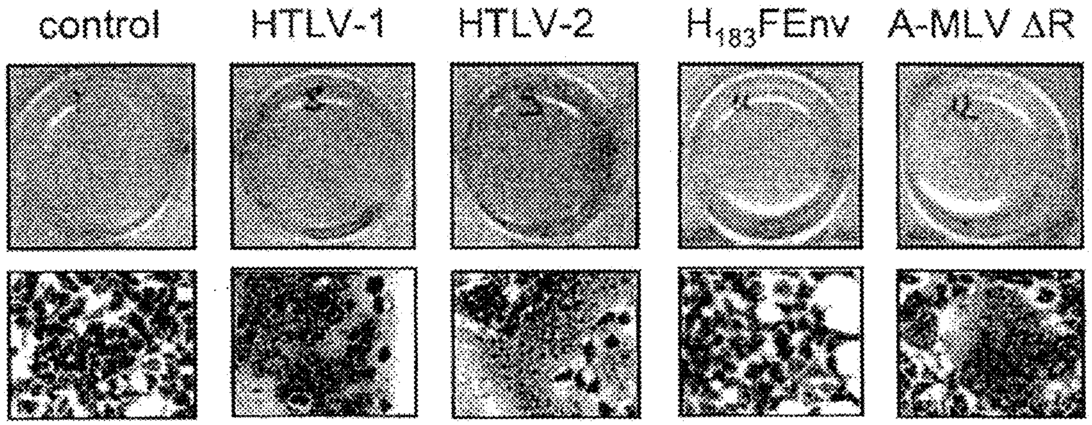
FIGS. 1*a*-1*d* Expression of the HTLV receptor-binding domain alters cellular metabolism.
Figure 1:
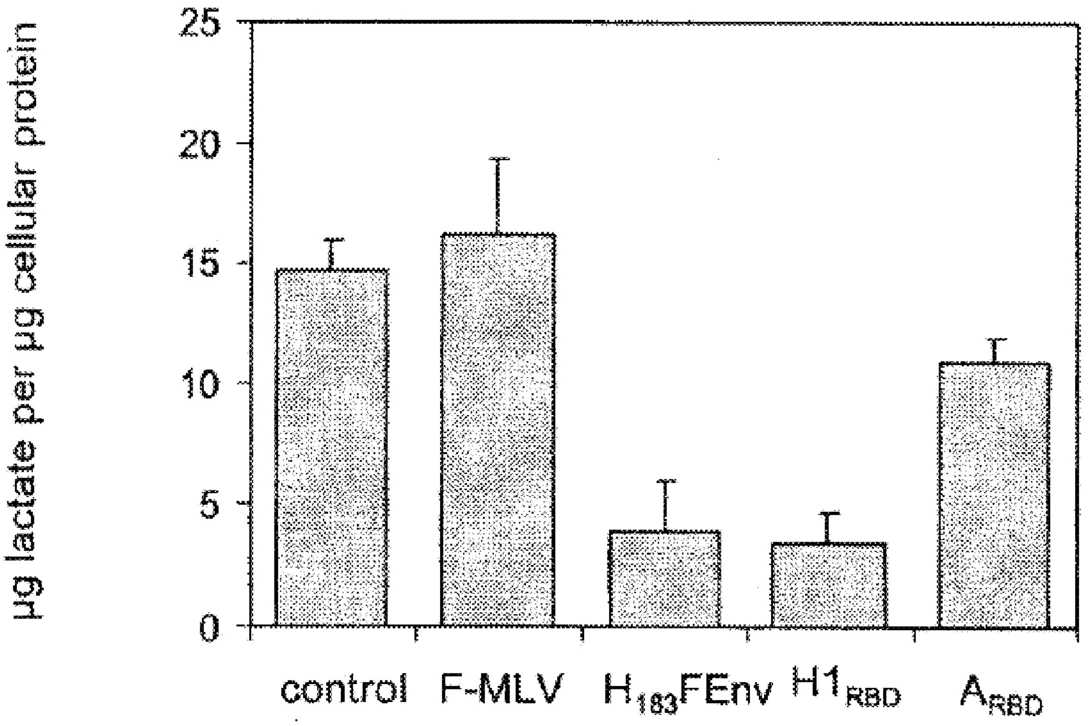
Figure 1:
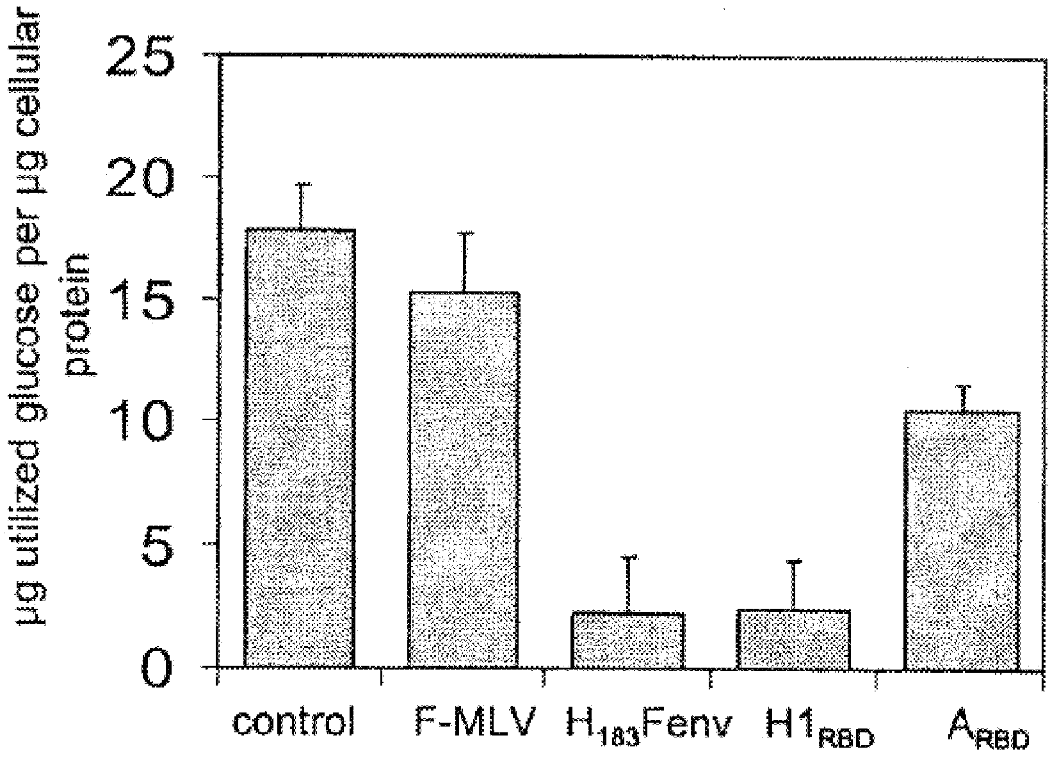
Figure 1:
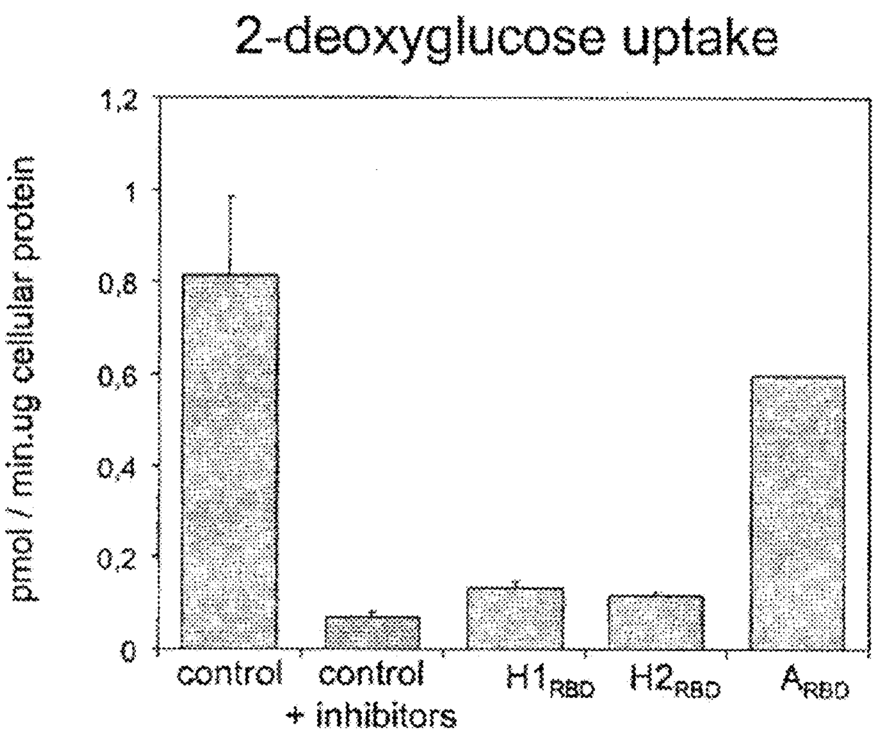
Figure 1:
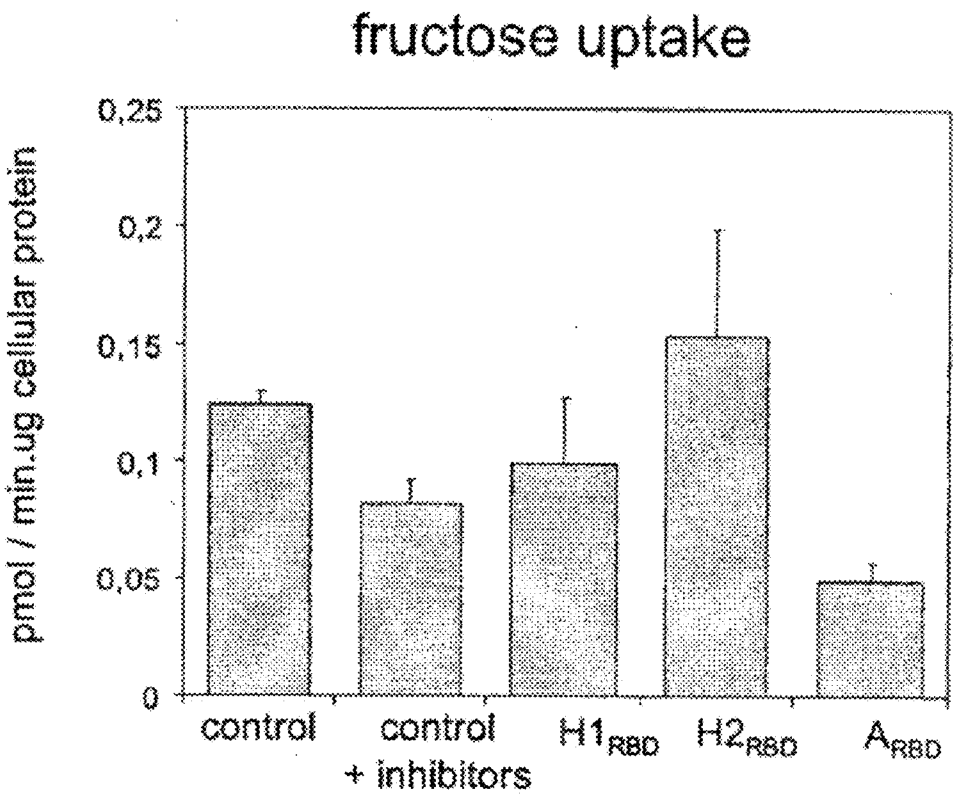
Figure 1:
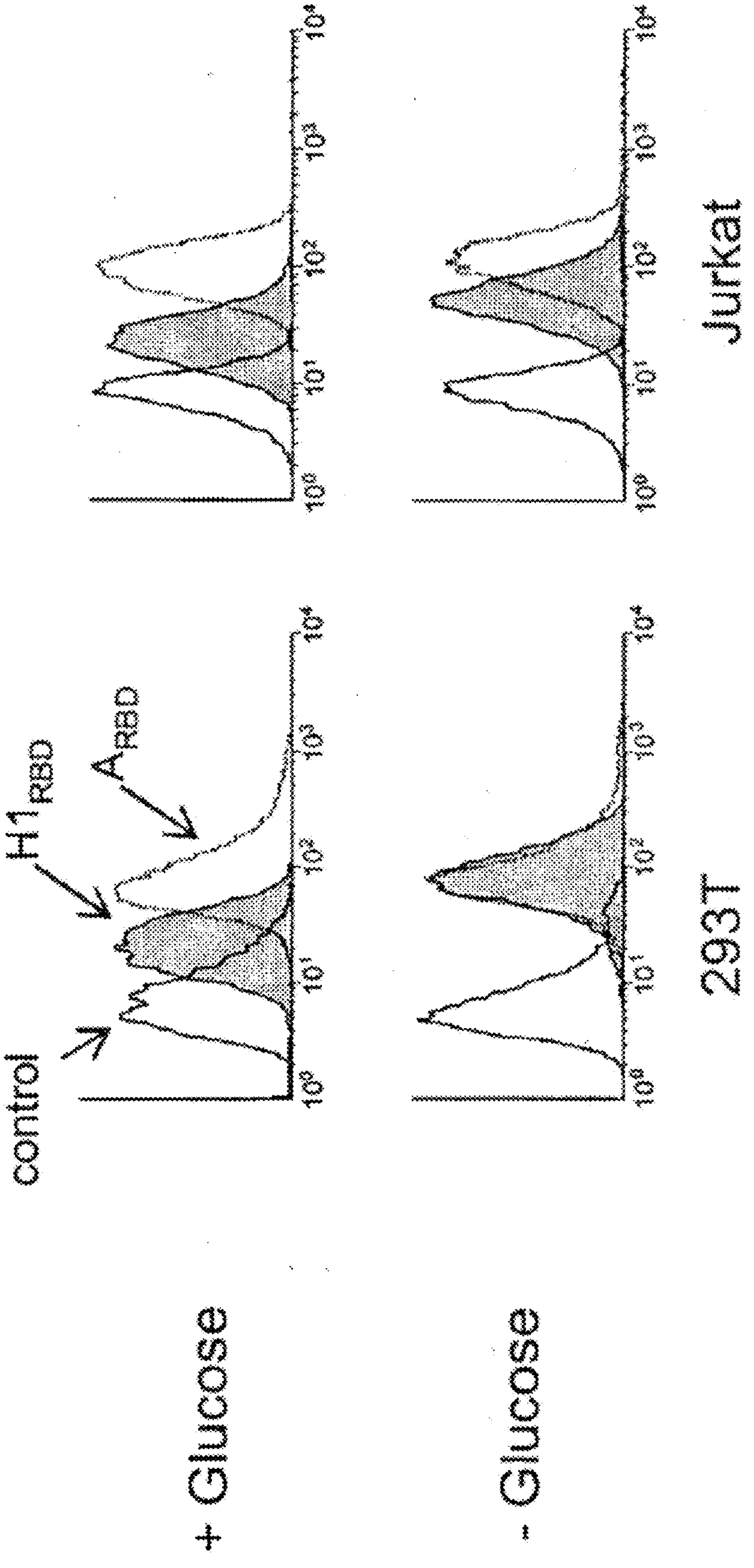

Cell proliferation in standard culture media is accompanied by acidification of the milieu that translates into a color change from red to yellow tones in the presence of the phenol-red pH indicator. Upon transfection of either highly syncytial HTLV-1 and HTLV-2 envelopes, or a non-syncytial chimeric envelope that harbors the HTLV-1 RBD in a MLV Env backbone ($H_{183}$FEnv), culture medium did not readily acidify, and harbored red tones for several days post-transfection (FIG. 1*a*). Moreover, expression of truncated soluble HTLV RBD proteins fused with either GFP, -HA, or -rFc tags also inhibited medium acidification. In contrast, no envelope construct that lacked HTLV RBD, including different MLV group envelopes, feline, porcine, lentiviral and Jaagsiekte retroviral Envs, as well as VSV-G and Ebola glycoproteins, had this effect. The lack of acidification associated with HTLV-1 or HTLV-2 Env expression was not an indirect consequence of their syncytial activity, since (i) medium acidification was observed in cells expressing a syncytial amphotropic-MLV Env (A-MLV devoid of the R peptide) (FIG. 1*a*) and (ii) medium acidification was blocked when HTLV Env was expressed in cells that are resistant to HTLV-Env mediated syncytia formation (NIH3T3 $TK^-$ cells) [Kim, 2003].

Decrease of pH in cell culture is primarily due to extracellular accumulation of lactate [Warburg, 1956]. Lactate is the major byproduct of anaerobic glycolysis in vitro and its excretion is mediated by an H+/lactate symporter [Halestrap, 1999]. We monitored lactate content in culture supernatants following transfection of various retroviral envelopes and RBD. Lactate accumulation was consistently 3-fold lower in $H_{183}$FEnv- and HTLV RBD-transfected cells than in control- or MLV Env-transfected cells (FIG. 1*b*). This decrease in extracellular glucose and fructose accumulation after HTLV RBD transfection was DNA dose-dependent. Moreover, we found that the decrease in glucose and fructose accumulation following transfection of HTLV RBD was apparent as early as 4 hours after the addition of fresh media (FIG. 1*c*).

Example 2

Receptor Binding and Lactate Metabolism

Figure 3:
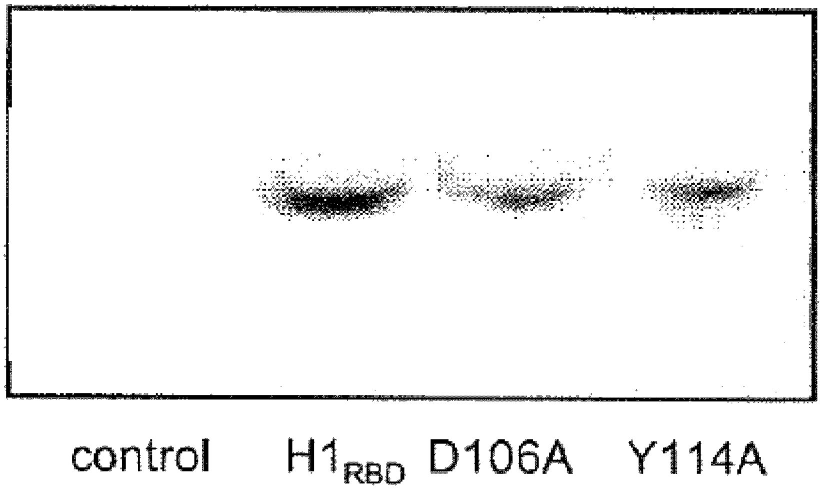
FIGS. 3*a*-3*c* HTLV receptor-binding correlates with altered lactate metabolism.
Figure 3:
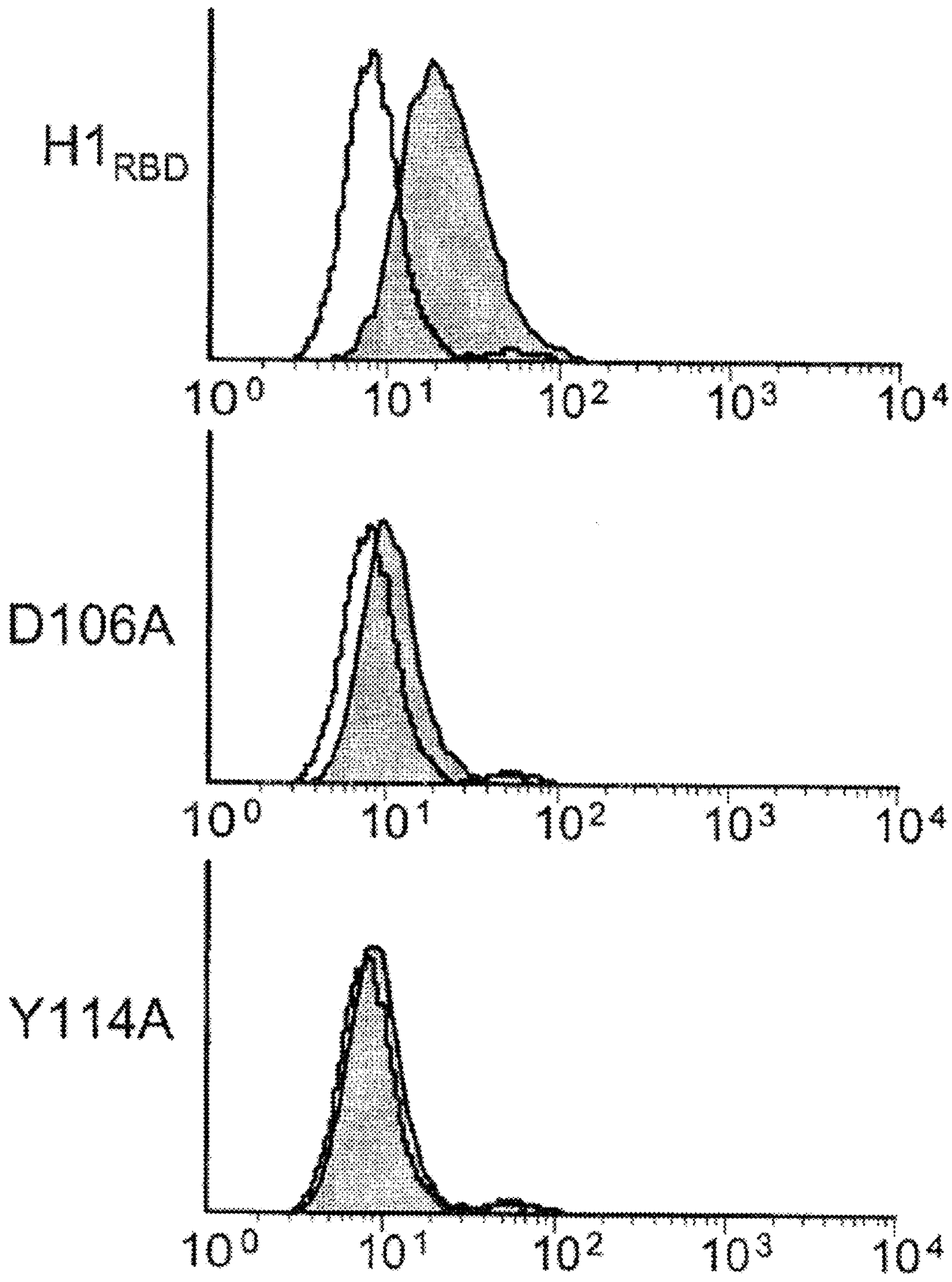
Figure 3:
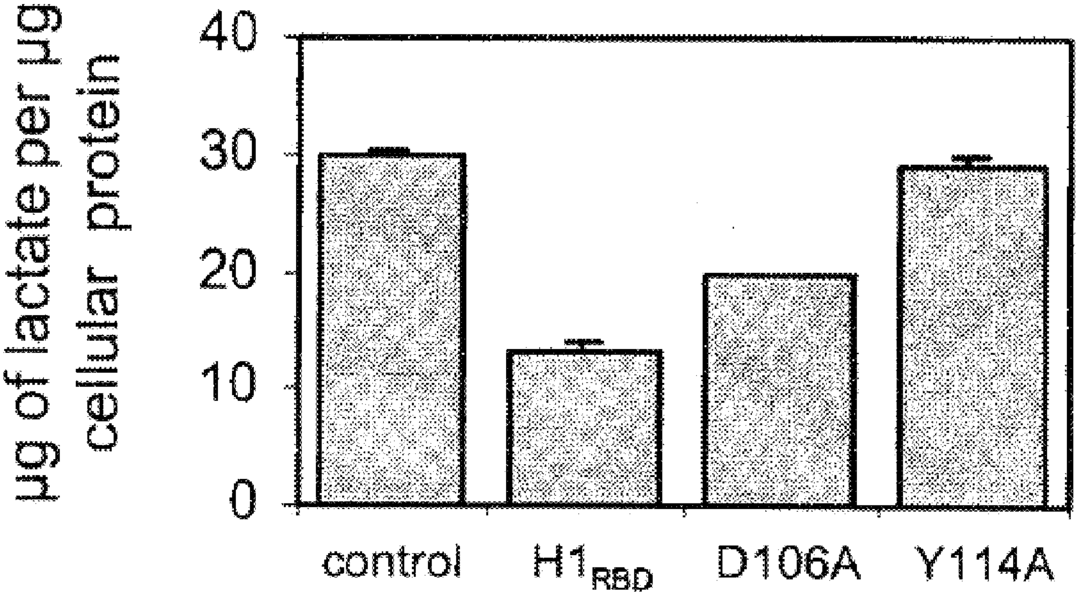

To examine whether a direct relationship exists between binding of the HTLV envelope receptor and diminished extracellular acidification and lactate accumulation, we attempted to generate HTLV-1 RBD ($H1_{RBD}$) mutants with impaired receptor binding capacities. To this end, mutations resulting in single alanine substitutions were introduced at two different positions in $H1_{RBD}$, D106 and Y114 which are highly conserved among primate T-lymphotropic viruses. Although both D106A and Y114A RBD mutants were expressed and secreted as efficiently as the wild-type $H1_{RBD}$ (FIG. 3*a*), they exhibited significantly reduced (D106A) or non-detectable (Y114A) binding to the HTLV receptor as detected by FACS analysis (FIG. 3*b*). Moreover, perturbations in lactate metabolism correlated with binding to the HTLV receptor: lactate accumulation was not reduced in cells expressing the non-binding Y114A RBD mutant and was minimally reduced in cells harboring the D106 RBD (FIG. 3*c*). Similar results were obtained with $H2_{RBD}$ harboring the same allelic mutations. These data favor a direct association between lactate-related metabolic alterations and HTLV Env receptor binding.

Extracellular lactate accumulates in cell cultures following its transport across cellular membranes by the MCT1 monocarboxylate transporter [Garcia, 1994]. Because HTLV and MLV share a common organization of the extracellular envelope [Kim, 2000] and the receptors for MLV Env are multispanning metabolite transporters [Overbaugh, 2001], we assessed whether the HTLV RBD bound to MCT1. Moreover, similar to our previous data concerning expression of the HTLV receptor on T cells [Manel, 2003], expression of MCT1 chaperone CD147 [Kirk, 2000] increases during T cell activation [Kasinrerk, 1992]. However, separate and combined overexpression of MCT1 and CD147 did not result in increased $H1_{RBD}$ binding, arguing against a role for these molecules as receptors for HTLV Env.

Example 3

HTLV Receptor and Glucose Metabolism

In addition to a decrease in extracellular lactate accumulation, expression of the HTLV RBD also led to decreased intracellular lactate content, indicative of metabolic alterations upstream of lactate transport. In cell cultures, lactate accumulation results from the degradation of glucose during anaerobic glycolysis. Therefore, we assessed whether the decreased accumulation of lactate observed upon expression of HTLV RBD was linked to glucose metabolism. We measured glucose consumption as normalized to cellular protein content. Glucose consumption of cells expressing an HTLV RBD within the context of the $H_{183}$FEnv entire envelope or the $H1_{RBD}$ was significantly decreased as compared to control cells (FIG. 1*b*) and this defect was detectable as early as 8 hours post transfection. To determine if this decrease in glucose consumption corresponded to a decrease in glucose transport across cellular membrane, we measured 2-deoxyglucose and fructose uptake in control cells and cells expressing HTLV RBD (FIG. 1*c*). We observed that expression of either HTLV-1 or HTLV-2 RBD induced an approximately 4-fold decrease in 2-deoxyglucose uptake, while A-MLV RBD had only a minor effect Inhibitors of glucose uptake, cytochalasin B and phloterin, also inhibited glucose uptake. These results were also true for 3-O-methylglucose transport. Fructose uptake in the same cells was not altered by the presence of HTLV-1 nor HTLV-2 RBD however A-MLV RBD induced a slight decreased. We next evaluated the effect of glucose deprivation on the availability of the HTLV receptor in both adherent human 293T cells and suspension Jurkat T cells. After overnight culture of cells in the absence of glucose, binding of $H1_{RBD}$ was consistently increased by 2-fold in both cell types (FIG. 1*d*). This effect of glucose deprivation was specific to HTLV as amphotropic MLV RBD ($A_{RBD}$) binding was only marginally affected (FIG. 1*d*). This phenomenon is reminiscent of a general metabolite transport feedback loop, whereby transporter availability at the cell surface increases upon substrate starvation [Martineau, 1972].

Example 4

HTLV Envelopes Bind Glucose Transporter-1

Figure 2:
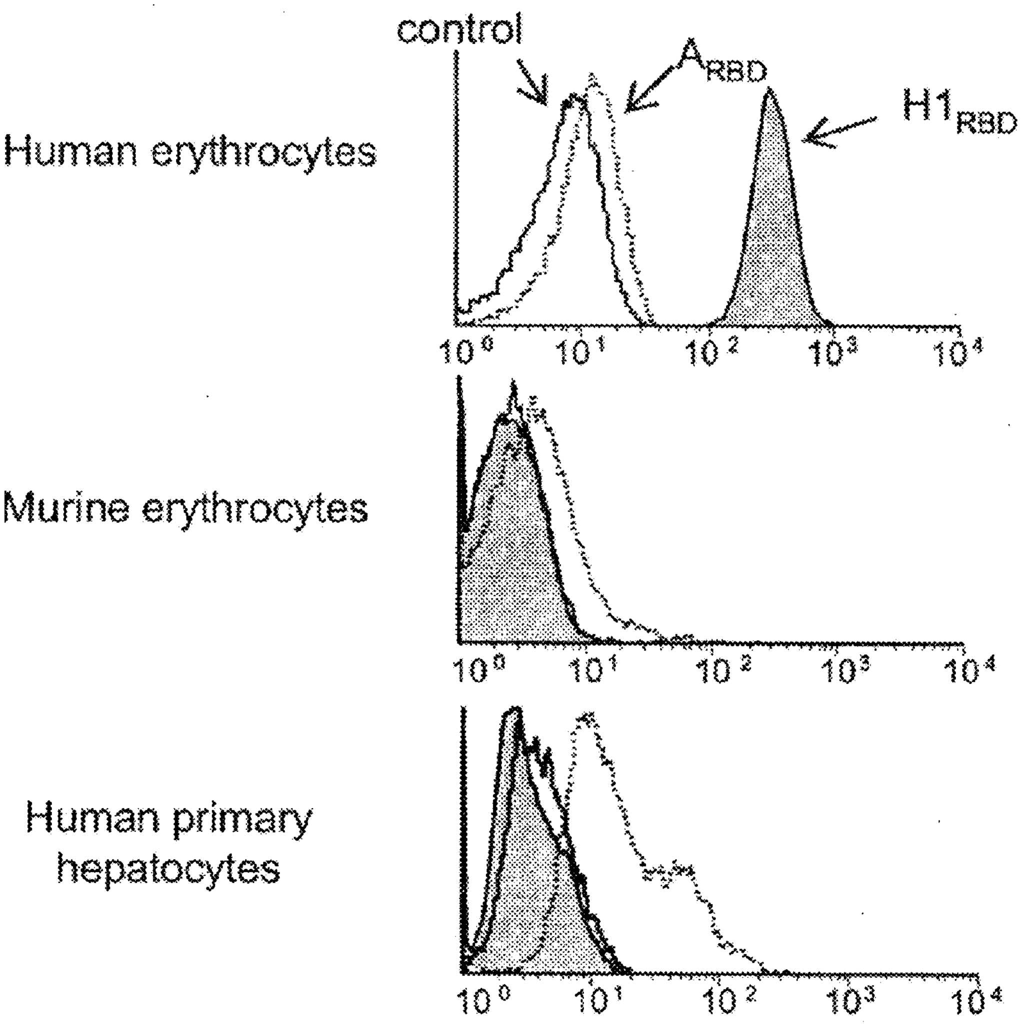
Figure 2:
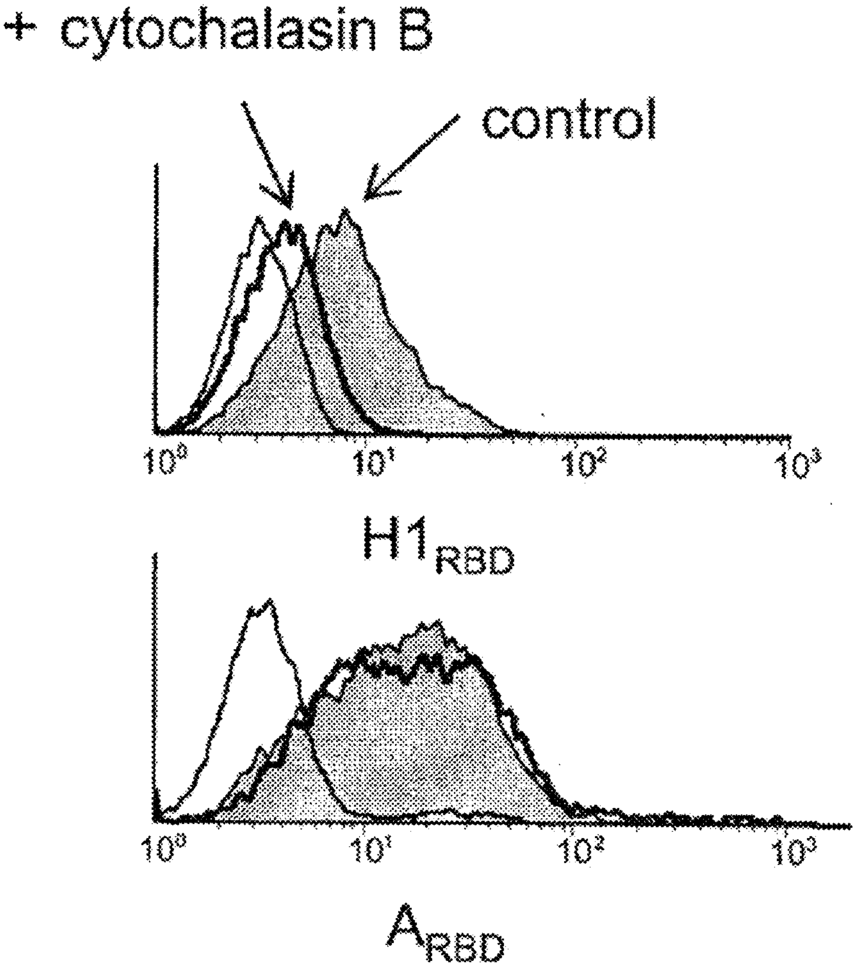

A simple model whereby the HTLV envelope inhibits glucose consumption via direct binding to a glucose transporter can explain the metabolic effects described above. Upon evaluation of the different glucose transporter candidates, GLUT-1 appears to be the only one encompassing all the known properties of the HTLV receptor. Indeed, GLUT-1 expression is increased upon glucose deprivation and is transports glucose in all vertebrate cells [Mueckler, 1985], while fructose is transported by GLUT-5. Furthermore, GLUT-1 is not expressed on resting primary T cells and its expression is induced upon T cell activation [Rathmell, 2000; Chakrabarti, 1994] with kinetics that are strikingly similar to what we have reported for the HTLV receptor [Manel, 2003]. Since human but not murine erythrocytes have been described to be the cells exhibiting the highest concentration of GLUT-1 [Mueckler, 1994], we evaluated HTLV receptor availability on freshly isolated red blood cells. Binding of $H1_{RBD}$ on human erythrocytes was strikingly efficient, reaching levels higher than those observed on any other tested cell type, whereas $A_{RBD}$ binding to erythrocytes was minimal (FIG. 2*a*). On murine erythrocytes however, no significant $H1_{RBD}$ binding could be detected, despite a similar $A_{RBD}$ binding on murine and human erythrocytes. Furthermore, primary human hepatocytes do not express GLUT-1. Accordingly, we were unable to detect $H1_{RBD}$ binding to human primary hepatocytes, while $A_{RBD}$ binding could be readily detected.

Figure 4:
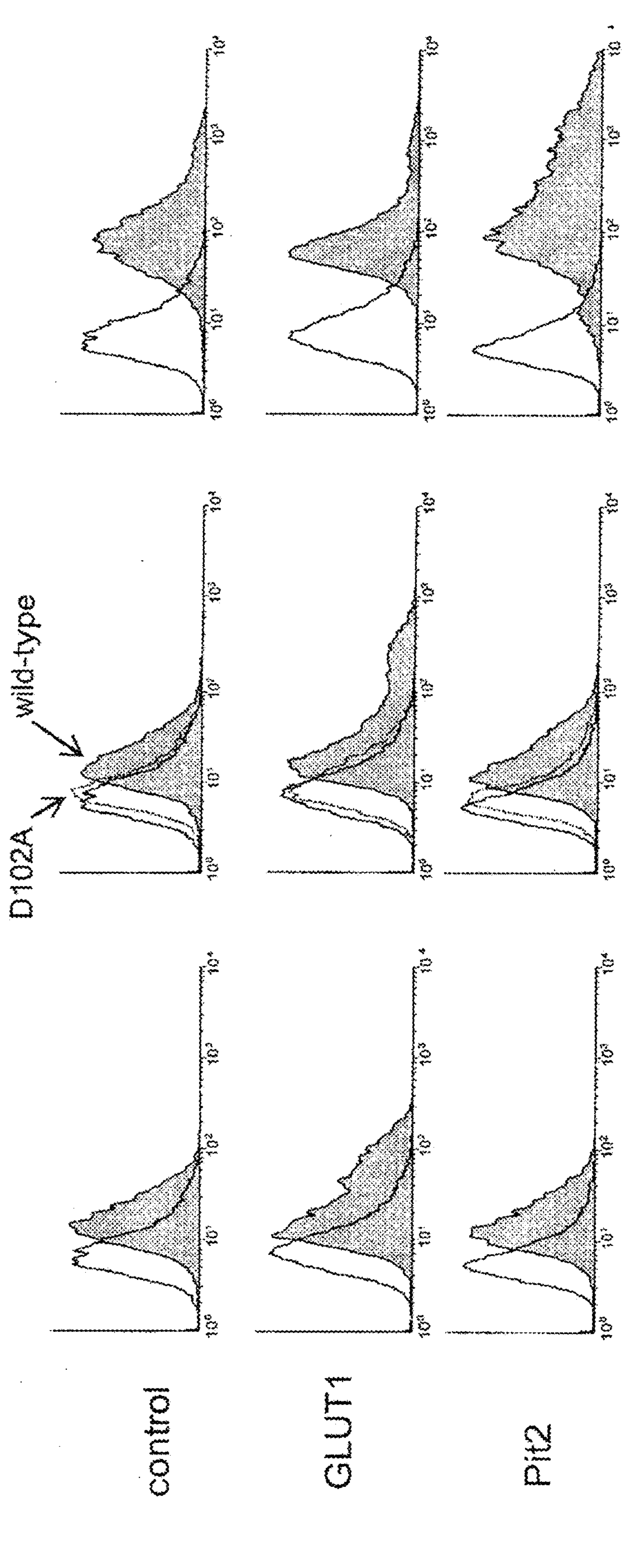
FIGS. 4*a*-4*c* GLUT-1 is a receptor for HTLV envelopes.
Figure 4:
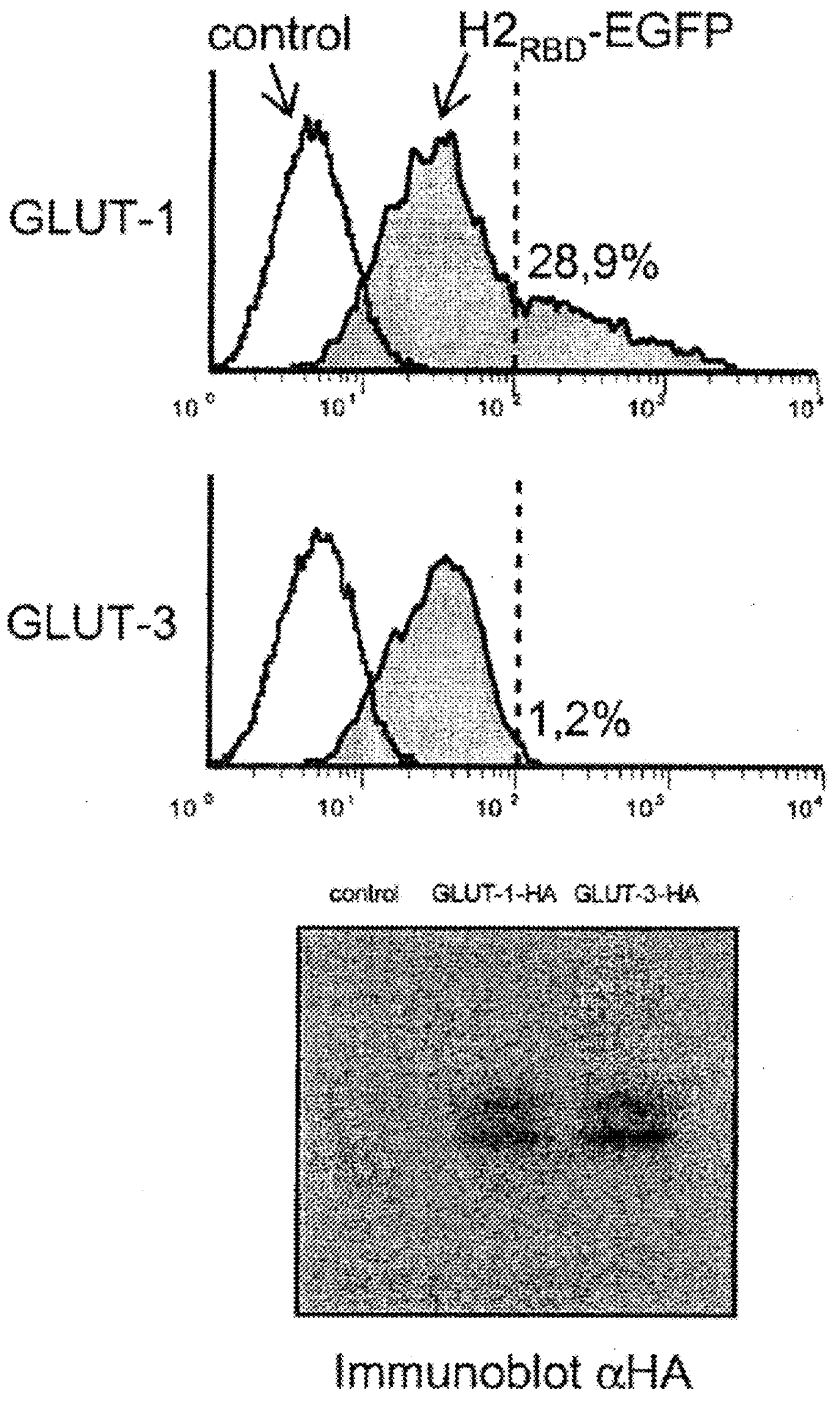
Figure 4:
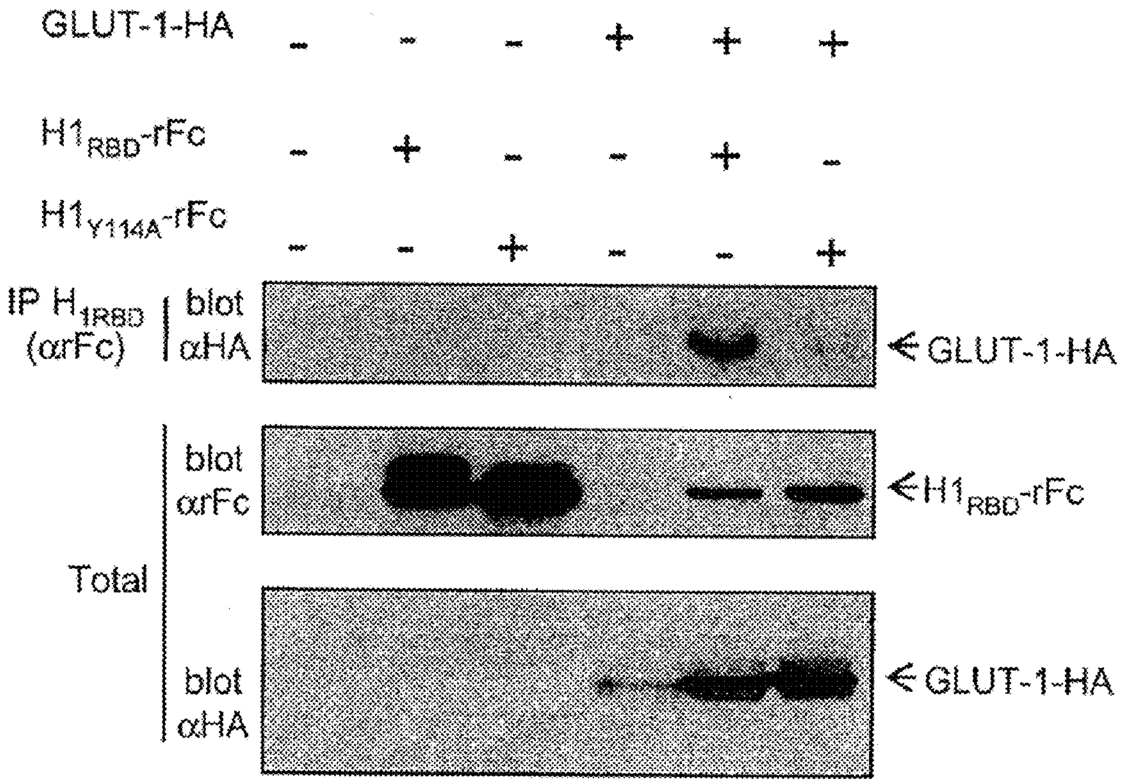

In order to directly test the ability of HTLV envelopes to bind GLUT-1, we derived a tagged GLUT-1 expression vector and overexpressed this protein in HeLa cells. Both $H1_{RBD}$ and $H2_{RBD}$ binding was dramatically increased upon GLUT-1 overexpression (FIG. 4*a*). This interaction was specific as the HTLV-2 binding-defective mutant, D102A, as well as its HTLV-1 counterpart, D106A, did not bind GLUT-1 (FIG. 4*a*). Furthermore, $H1_{RBD}$ and $H2_{RBD}$ binding remained at background levels upon overexpression of the amphotropic MLV envelope receptor, the inorganic phosphate transporter PiT2 [Miller, 1994]. Conversely, binding of $A_{RBD}$ was not increased after GLUT-1 overexpression but as expected, this interaction was increased upon transfection of PiT2 (FIG. 4*b*). GLUT-3 is the closest isoform to GLUT-1, and transports glucose with kinetics similar to that of GLUT-1. Thus, we derived a tagged GLUT-3 expression vector. Albeit similar overexpression levels of GLUT-1 and GLUT-3 in 293T cells, GLUT-3 did not induce any increase in $H1_{RBD}$ binding (FIG. 4*b*), suggesting that increase $H1_{RBD}$ binding in cells overexpressing GLUT-1 is not an indirect consequence of increased glucose uptake. To determine if GLUT-1 transfected cells were directly responsible for the observed increased in $H1_{RBD}$ binding, we derived fluorescent tagged GLUT-1 and GLUT-3 to uniquevocally identity GLUT-overexpressing cells in the course of our FACS analysis. In this context, only cells overexpressing GLUT-1-DsRed2 displayed a significant increase in $H1_{RBD}$ binding, while overexpressing GLUT-3-DsRed2 had no effect on $H1_{RBD}$ binding. Consequently, we tested if HTLV glycoproteins directly interact with GLUT-1 proteins. To this end, we evaluated the ability of $H1_{RBD}$ to immunoprecipitate GLUT-1. As shown on FIG. 4*c*, GLUT-1 could be readily detected upon immunoprecipitation with anti-rabbit-Fc-beads when it was co-expressed with $H1_{RBD}$, but could not be detected when expressed alone or with the $H1_{RBD}$ Y114A mutant. Moreover, a GFP-tagged HTLV-2 RBD colocalized with GLUT-1 but not with PiT2 as assessed by fluorescence microscopy. Therefore, the GLUT-1 glucose transporter is an essential component of the HTLV envelope receptor.

Figure 5:
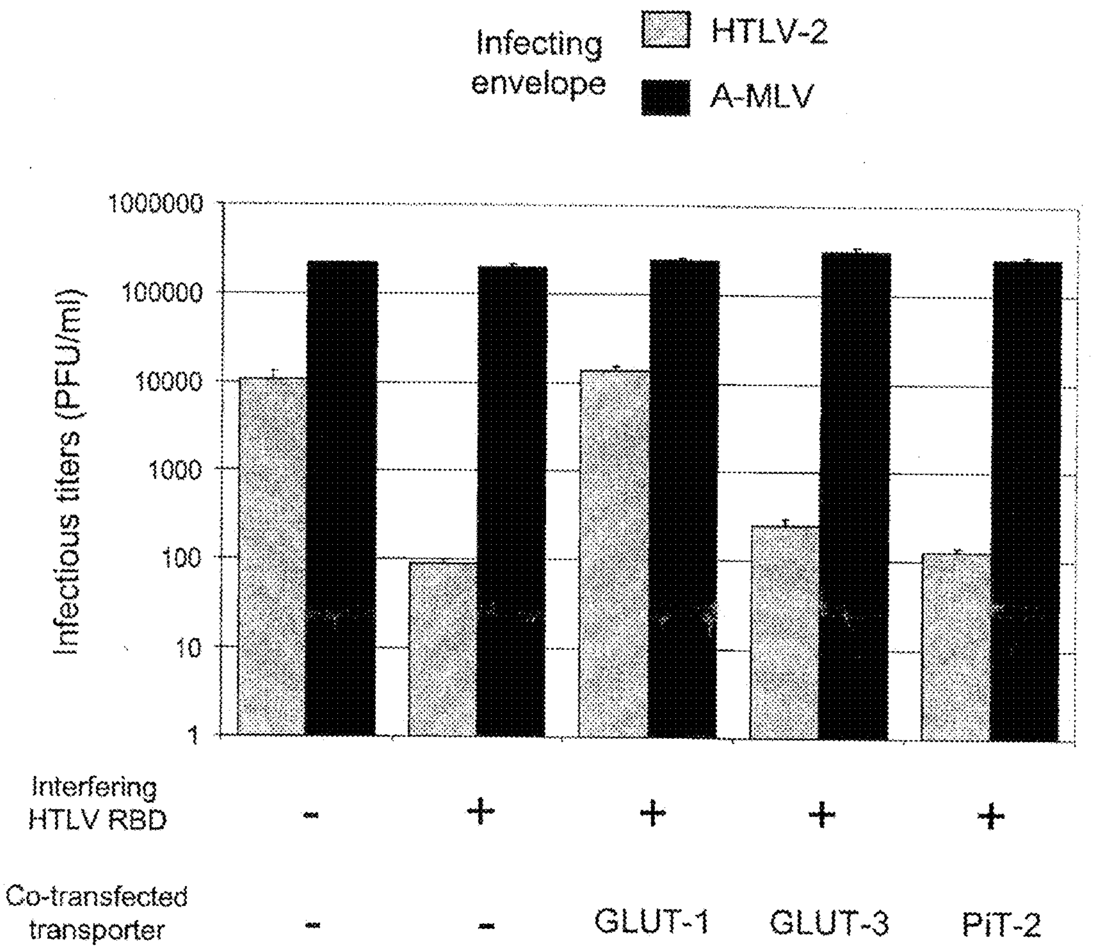
FIG. 5 GLUT-1 is an entry receptor for HTLV. Infections titer of MLV particles pseudotypes with HTLV-2 or A-MLV envelopes on 293T cells following transfection of an irrelevant or interfering $H2_{RBD}$ expression vectors alone or in addition to GLUT-1, GLUT-3 or Pit2 expression vectors.
Figure 6:
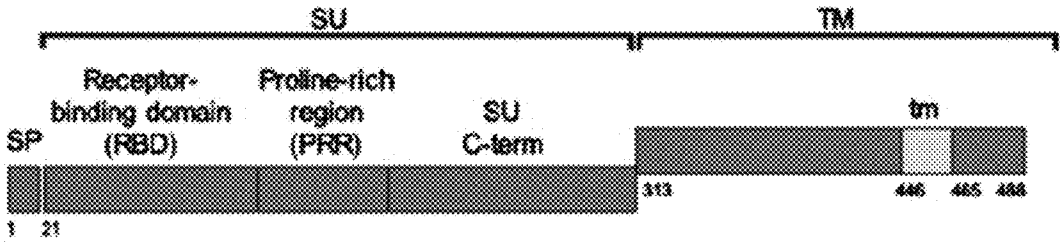
FIG. 6 represents a schematic diagram of the HTLV-1 envelope glycoprotein (Env). Mature Env is constituted of two subunits formed after cleavage of the amino terminal signal peptide (SP) and cleavage of the Env polyprotein precursor into the extracellular SU and the membrane-anchored TM. SU comprises three distinct subdomains: an amino terminal receptor-binding domain (RBD), a central proline-rich region (PRR) and a carboxy terminal domain (C-term).

Interaction of GLUT-1 with its ligand cytochalasin B inhibits glucose transport [Kasahara, 1977]. Since we showed that binding of HTLV envelopes to GLUT-1 inhibits glucose consumption and uptake, we tested whether cytochalasin B would abrogate HTLV RBD binding. Indeed, cytochalasin B treatment of Jurkat T cells dramatically inhibited binding of $H1_{RBD}$, whereas binding of $A_{RBD}$ was not affected (FIG. 5). Thus, GLUT-1 directed glucose transport as well as binding of HTLV envelopes to GLUT-1 are similarly inhibited by the cytochalasin B ligand. Altogether, these data demonstrate that GLUT-1 is a receptor for HTLV envelopes.

Viral receptor permits entry and thus infection. No cellular system currently exists that lacks GLUT-1 expression. Thus, we developed a system in which HTLV infection is specifically inhibited at the level of envelope-receptor interaction. In this system, over-expression of HTLV-2 RBD interferes with infecting incoming HTLV particles and specifically decreases HTLV titers by at least 2 logs, while no effect is detected on control A-MLV titers. To determine if GLUT-1 is an entry receptor for HTLV, we overexpressed GLUT-1, GLUT-3 or Pit2 in addition to the interfering $H2_{RBD}$. While Pit2 and GLUT-3 had no effect on HTLV titers, GLUT-1 completely alleviated the interference to infection induced by $H2_{RBD}$ (FIG. 5). Interestingly, both GLUT-1 and GLUT-3, but not Pit2, alleviated the alteration of glucose metabolism induced by the HTLV RBD. Thus, GLUT-1 is an entry receptor for HTLV.

Discussion

Here we show that HTLV-1 and -2 envelopes interact with GLUT-1 through their receptor binding domains. This interaction strongly inhibits glucose consumption and glucose uptake, leading to decreased lactate production and a block in extracellular milieu acidification. Mutations that specifically altered receptor binding of both HTLV-1 and 2 envelopes released the block in glucose consumption, indicative of a direct correlation between receptor binding determinants in the HTLV envelopes and glucose transport. Glucose starvation was rapidly followed by increased binding of HTLV envelopes, highlighting a nutrient-sensing negative feedback loop between glucose availability and cell surface HTLV receptor expression. Further evidence converged to identify GLUT-1 as the receptor, including increased binding of HTLV RBD upon overexpression of GLUT-1 but not GLUT-3, immunoprecipitation of GLUT-1 by $H1_{RBD}$ but not the receptor-binding mutant $H1_{RBD}$ Y114A, uppermost binding of HTLV RBD on human erythrocytes, where GLUT-1 is the major glucose transporter isoform, and no binding of HTLV RBD on human primary hepatocytes and murine erythrocytes, where GLUT-1 is minimally expressed. Finally, GLUT-1 could specifically alleviate interference to infection induced by HTLV RBD. GLUT-1 fits all other known properties of the HTLV receptor. Indeed, as previously demonstrated for the HTLV receptor [Manel, 2003], GLUT-1, but not the GLUT 2-4 isoforms, is not expressed on resting T lymphocytes [Chakrabarti, 1994; Korgun, 2002] and is induced upon immunological [Frauwirth, 2002; Yu, 2003] or pharmacological [Chakrabarti, 1994] activation. Moreover, GLUT-1 orthologues are highly conserved among vertebrates, but are highly divergent between vertebrates and insects [Escher, 1999].

GLUT-1 is thus a new member of the multimembrane spanning metabolite transporters that serve as receptors for retroviral envelopes. Interestingly, until now, all envelopes that recognize these receptors have been encoded by retroviruses that have a so-called simple genetic organization, such as MLV, feline leukemia viruses, porcine endogenous retrovirus and the gibbon ape leukemia virus [Overbaugh, 2001], whereas HTLV belongs to the so-called complex retroviruses which code for several additional regulatory proteins. However, we have shown that in contrast to the wide phylogenetic divergence of their genomic RNA, the envelopes of HTLV and MLV share a similar modular organization with some highly conserved amino acid motifs in their respective receptor binding domains [Kim, 2000].

Cell-to-cell contact appears to be required for HTLV transmission, and the cytoskeleton appears to play a major role in this process [Igakura, 2003]. Indeed, we observed that the HTLV receptor, despite pancellular expression, is specifically concentrated to mobile membrane regions and cell-to-cell contact areas. It should therefore be expected that the HTLV envelope receptor is associated to the cytoskeleton Importantly, a cytoplasmic-binding partner of GLUT-1, GLUT1CBP, which encodes a PDZ domain, has been reported to link GLUT-1 to the cytoskeleton [Bunn, 1999]. It will therefore be interesting to evaluate the respective roles of the HTLV envelope, its cytoskeleton-associated cellular partners, such as GLUT-1, GLUT1CBP and their immediate interacting cell components.

Because expression of the HTLV receptor is induced upon glucose starvation, transmission of HTLV may be more efficient in cells that are locally starved for glucose, such as lymphocytes in lymph nodes [Yu, 2003]. Furthermore, the ability of circulating erythrocytes to dock HTLV, as shown here, might provide a means to distribute HTLV to such tissues.

The identification of GLUT-1 as a receptor for HTLV envelopes provides additional clues as to the ubiquitous in vitro expression of the receptor on cell lines and the paradoxical restriction of HTLV tropism to T lymphocytes in vivo. Rapid and dramatic metabolic alterations associated with the blockade of glucose consumption are likely to take place upon expression of the HTLV envelope in vivo, early after infection. Therefore, we propose that in vivo, HTLV infection initially spreads with a large tropism, however early after infection the vast majority of cells that are highly dependent on GLUT-1 activity are rapidly eliminated. In contrast, resting T lymphocytes that have an extremely low metabolic rate and as such are much less dependent on glucose uptake, can tolerate this effect and are therefore maintained in vivo. Furthermore, local imbalances in the access to glucose following HTLV infection may lead to specific physiological alterations [Akaoka, 2001]. In this regard, it will be of interest to study the potential relationship between HTLV-associated neuropathologies and the specific dependence of neurons on GLUT-1 mediated glucose consumption [Siegel, 1998].

Materials and Methods

Cell culture. 293T human embryonic kidney and HeLa cervical carcinoma cells were grown in Dulbecco's modified Eagle medium (DMEM) with high glucose (4.5 g/l) and Jurkat T-cells were grown in RPMI supplemented with 10% fetal bovine serum (FBS) at 37° C. in a 5% CO2-95% air atmosphere. For glucose starvation experiments, cells were grown in either glucose-free DMEM (Life Technologies) or glucose-free RPMI—(Dutscher) with 10% dialyzed FBS (Life Technologies) and glucose (1 g/l) was supplemented when indicated.

Expression vectors. Full length envelope expression vectors for HTLV-1 (pCEL/2[Denesvre, 1995]) and Friend ecotropic MLV (pCEL/F [Denesvre, 1995]), have been previously described. For the HTLV-2 envelope, a fragment from pHTE2 [Rosenberg, 1998] encompassing the tax, rex and env genes and the 3' LTR was inserted in the pCSI [Battini, 1999] vector (pCSIX.H2). Full length envelope expression vectors for amphotropic MLV (pCSI.A), or devoid of its R peptide (pCSI.AΔR), and $H_{183}$FEnv that contains the N-terminal 183 amino acids of the HTLV-1 receptor-binding domain in the F-MLV envelope background, as well as truncated envelope expression vectors, derived from pCSI and encoding either of the first 215 residues of HTLV-1 SU ($H1_{RBD}$), the first 178 residues of HTLV2-SU ($H2_{RBD}$) or the first 397 residues of the amphotropic murine leukemia virus (MLV) SU (Amp), fused to a C-terminal rabbit IgG Fc tag (rFc) or to EGFP ($H2_{RBD}$-GFP). All point mutations introduced in HTLV-1 and -2 RBD constructs were generated using the quickchange site-directed mutagenesis method and mutations were verified by sequencing. Human Glut-1 and Glut-3 cDNA were amplified by PCR from the pLib HeLa cDNA library (Clontech), and inserted into pCHIX, a modified version of the pCSI vector that contains a cassette comprising a factor Xa cleavage site, two copies of the hemagglutinin (HA) tag, and a histidine tag. The resulting construct (pCHIX.hGLUT1) encodes a GLUT-1 protein with a HA-His tag at the C-terminal end. GLUT-1 and GLUT-3 were also inserted in a modified pCSI vector containing a DsRed2 C-terminal tag. Similarly, human CD147 was amplified from 293T total RNA by RT-PCR and inserted into the pCHIX backbone in frame with the HA-His tag (pCHIX.hCD147).

Envelope expression and metabolic measurements. 293T cells were transfected with the various envelope expression vectors using a modified version of the calcium phosphate method. After an overnight transfection, cells were washed in phosphate-buffered saline (PBS) and fresh medium was added. Media were harvested at the indicated time points, filtered through a 0.45-μm pore-size filter, and lactate and glucose were measured with enzymatic diagnostic kits (Sigma). Values were normalized to cellular protein content using the Bradford assay (Sigma) after solubilization of cells in lysis buffer (50 mM Tris-HCl pH 8.0, 150 mM NaCl, 0.1% sodium dodecyl sulfate, 1.0% Nonidet P-40, 0.5% deoxycholate) and clarification by centrifugation.

Assay of hexose uptake. 2-deoxy-D[1-$^3$H]glucose, D[U-$^{14}$C]fructose and 3-O-[$^{14}$C]methyl-D-glucose were obtained from Amersham. Hexose uptake assay were adapted from Harrison et al. 1991). After transfection, approximately 250,000 were seeded/well in 24-well plates. The next day, cells were washed two times in PBS, incubated in serum-free DMEM, washed one time in serum-free glucose-free DMEM, and incubated for 20' in 500 μl serum-free glucose-free DMEM modulo inhibitors (20 μM cytochalasin B, 300 μM phloretin; SIGMA). Uptake was initiated by adding labeled hexoses to a final concentration of 0.1 mM (2 μCi/ml for 2-2-deoxy-D[1-$^3$H]glucose and 0.2 μCi/ml for D[U-$^{14}$C] fructose and 3-O-[$^{14}$C]methyl-D-glucose) and cells were incubated for 5' additional minutes. Cells were then resuspended in 500 μl cold serum-free glucose-free DMEM, wash one time in serum-free glucose-free DMEM, and solubilized in 400 μl of 0.1% SDS. 3 μl was used for Bradford normalization, while the rest was used for detection of either $^3$H or $^{14}$C by liquid scintillation in a Beckman counter.

Western blots. Culture media (10 μl) from 293T cells expressing wild type or mutant HTLV-1 RBDs, and/or GLUT-1 or GLUT-3 expression vector. were subjected to electrophoresis on SDS-15% acrylamide gels, transferred onto nitrocellulose (Protran; Schleicher & Schuell), blocked in PBS containing 5% powdered milk and 0.5% Tween 20, probed with either a 1:5000 dilution of horseradish peroxidase-conjugated anti-rabbit immunoglobulin or 1:2000 dilution of anti-HA 12CA5 (Roche) monoclonal antibody followed by a 1:5000 dilution of horseradish peroxidase-conjugated anti-mouse immunoglobulin, and visualized using an enhanced chemiluminescence kit (Amersham).

Binding assays. Binding assays were carried out as previously described [Manel, 2003]. Briefly, 5×10$^5$ cells (293T, HeLa, Jurkat or freshly isolated human erythrocytes) were incubated with 500 μl of $H1_{RBD}$, $H2_{RBD}$ or $A_{RBD}$ supernatants for 30 min at 37° C., washed with PBA (1% BSA, 0.1% sodium azide in PBS), and incubated with a sheep anti-rabbit IgG antibody conjugated to fluorescein isothiocyanate (Sigma). When indicated, cytochalasin B (20 μM; Sigma) was added to cells for 1 hour prior to binding analyses. Binding was analyzed on a FACSCalibur (Becton Dickinson) and data analysis was performed using CellQuest (Becton Dickinson) and WinMDI (Scripps) softwares.

Infections. 293T cells were transfected in 6-wells plate, and one day after transfection, medium was replaced by high glucose DMEM supplemented with fructose (5 g/l) and non-essential amino acids. The next day, infection was initiated by adding supernatants containing MLV particles pseudotyped with either HTLV-2 or A-MLV envelopes. The following day, fresh medium was added, and 24 hours later cells were fixed and stained for alkaline phosphatase activity and dark focus of infection were counted. Viral particles were obtained by transfecting 293T cells with pLAPSN, pGagPol and either pCSIX.H2 or pCSI.A, and harvesting the 0.45 μm-filtered supernatants 24 hours later.

The invention claimed is:

1. An isolated fusion polypeptide, wherein said fusion polypeptide consist of a soluble receptor binding domain (RBD) ligand derived from the soluble part of the glycoprotein of the human T-cell leukemia virus (HTLV-2) binding to the Glucose Transporter 1 (GLUT1), consisting of the amino acid sequence selected from the group consisting of SEQ ID NO: 4, SEQ ID NO: 5, SEQ ID NO: 7, SEQ ID NO: 43, and fragments of SEQ ID NO: 4 or SEQ ID NO: 43, wherein said fragments of SEQ ID NO: 43 are polypeptides delimited in their N-terminal extremity by the amino acid located in position 1 to 90 and in their C-terminal extremity by the amino acid located in position 135 to 245 of SEQ ID NO: 43; and wherein said fragments of SEQ ID NO: 4 consist of amino acids 19 to 224 of SEQ ID NO: 4, or 20 to 224 of SEQ ID NO: 4, or 21 to 224 of SEQ ID NO: 4, or 19 to 178 of SEQ ID NO: 4, or 20to 178 of SEQ ID NO: 4, or 21 to 178 of SEQ ID NO: 4, and wherein said isolated polypeptide is chemically modified to add a fluorochrome or a fluorescent compound.

2. The isolated polypeptide according to claim 1, wherein said polypeptide binds to the Glucose Transporter 1 (GLUT1) comprising the amino acid sequence SEQ ID NO: 2 or to a fragment of GLUT1 having an amino acid sequence selected from the group consisting of SEQ ID NO: 35 to SEQ ID NO: 42.

3. The isolated polypeptide according to claim 1, wherein the fluorochrome or fluorescent compound is selected from the group consisting of Cyanine dye, Alexa dye and Quantum dye.

4. A method for diagnosing a GLUT1 related disease comprising:
collecting a biological sample from a subject,
determining the level of GLUT1 expression at a cell surface using the isolated polypeptide of claim 1, and
comparing said level to a reference value for GLUT1 expression at the cell surface in a biological sample from a healthy individual, wherein an elevated level or decreased level of GLUT1 expression in the sample from the subject indicates a GLUT1 related disease.

5. The method according to claim 4, wherein said GLUT1 related disease is GLUT1 deficiency syndrome.

6. The method according to claim 4, wherein said GLUT1 related disease is a cancer disease.

7. An isolated fusion polypeptide, wherein said fusion polypeptide consists of:
a soluble receptor binding domain (RBD) ligand derived from the soluble part of the glycoprotein of the human T-cell leukemia virus (HTLV-2) binding to the Glucose Transporter 1 (GLUT1), consisting of the amino acid sequence selected from the group consisting of SEQ ID NO: 4, SEQ ID NO: 5, SEQ ID NO: 7, SEQ ID NO: 43, and fragments of SEQ ID NO: 4 or SEQ ID NO: 43,
wherein said fragments of SEQ ID NO: 43 are polypeptides delimited in their N-terminal extremity by the amino acid located in position 1 to 90 and in their C-terminal extremity by the amino acid located in position 135 to 245 of SEQ ID NO: 43, and
wherein said fragments of SEQ ID NO: 4 consist of amino acids 19 to 224 of SEQ ID NO: 4, or 20 to 224 of SEQ ID NO: 4, or 21 to 224 of SEQ ID NO: 4, or 19 to 178 of SEQ ID NO: 4, or 20 to 178 of SEQ ID NO: 4, or 21 to 178 of SEQ ID NO: 4; and
a Tag, an antibody constant fragment, or a fluorescent protein.

8. The isolated fusion polypeptide according to claim 7, wherein the tag is selected from the group consisting of hemaglutinin tag, poly arginine tag, poly histidine tag, myc tag, strep tag, S-tag, HAT tag, 3 times flag tag, calmodulin-binding peptide tag, SBP tag, chitin binding domain tag, GST tag, maltose-binding protein tag, fluorescent protein tag, T7 tag, V5tag and Xpress tag.

9. The isolated fusion polypeptide according to claim 7, wherein the antibody constant fragment is selected from the group consisting of Fc fragment from rabbit and Fc fragment from mouse.

10. The isolated fusion polypeptide according to claim 7, wherein the fluorescent protein is GFP.

11. The isolated fusion polypeptide according to claim 7, wherein said polypeptide binds to the Glucose Transporter 1 (GLUT1) comprising the amino acid sequence SEQ ID NO: 2, or to a fragment of GLUT1 having an amino acid sequence selected from the group consisting of SEQ ID NO: 35 to SEQ ID NO: 42.

12. A kit of parts comprising at least one isolated fusion polypeptide, wherein said fusion polypeptide is the fusion polypeptide of claim 7.

13. A method for diagnosing a GLUT1 related disease comprising:
collecting a biological sample from a subject,
determining the level of GLUT1 expression at a cell surface using the isolated polypeptide of claim 7, and
comparing said level to a reference value for GLUT1 expression at the cell surface in a biological sample from a healthy individual, wherein an elevated level or decreased level of GLUT1 expression in the sample from the subject indicates a GLUT1related disease.

14. The method according to claim 13, wherein said GLUT1 related disease is GLUT1 deficiency syndrome.

15. The method according to claim 13, wherein said GLUT1 related disease is a cancer disease.

16. A composition comprising at least one isolated fusion polypeptide, wherein said fusion polypeptide consists of:
a soluble receptor binding domain (RBD) ligand derived from the soluble part of the glycoprotein of the human T-cell leukemia virus (HTLV-2) binding to the Glucose Transporter 1 (GLUT1), consisting of the amino acid sequence selected from the group consisting of SEQ ID NO: 4, SEQ ID NO: 5, SEQ ID NO: 7, SEQ ID NO: 43, and fragments of SEQ ID NO: 4 or SEQ ID NO: 43,
wherein said fragments of SEQ ID NO: 43 are polypeptides delimited in their N-terminal extremity by the amino acid located in position 1 to 90 and in their C-terminal extremity by the amino acid located in position 135 to 245 of SEQ ID NO: 43; and
wherein said fragments of SEQ ID NO: 4 consist of amino acids 19 to 224 of SEQ ID NO: 4, or 20 to 224 of SEQ ID NO: 4, or 21 to 224 of SEQ ID NO: 4, or 19 to 178 of SEQ ID NO: 4, or 20 to 178 of SEQ ID NO: 4, or 21 to 178 of SEQ ID NO: 4; and
a Tag, an antibody constant fragment, or a fluorescent protein.

17. The composition according to claim 16, being a pharmaceutical composition and further comprising a pharmaceutically acceptable excipient.

* * * * *

SEQUENCE LISTING

```
<160> NUMBER OF SEQ ID NOS: 55

<210> SEQ ID NO 1
<211> LENGTH: 3687
<212> TYPE: DNA
<213> ORGANISM: Homo sapiens
<220> FEATURE:
<221> NAME/KEY: source
<222> LOCATION: 1..3687
<223> OTHER INFORMATION: /mol_type="unassigned DNA"
      /note="Nucleic acid sequence of GLUT1"
      /organism="Homo sapiens"

<400> SEQUENCE: 1

tccaccattt tgctagagaa ggccgcggag gctcagagag gtgcgcacac ttgccctgag      60

tcacacagcg aatgccctcc gcggtcccaa cgcagagaga acgagccgat cggcagcctg     120

agcgaggcag tggttagggg gggccccggc cccggccact cccctcaccc cctccccgca     180

gagcgccgcc caggacaggc tgggccccag gccccgcccc gaggtcctgc ccacacaccc     240

ctgacacacc ggcgtcgcca gccaatggcc ggggtcctat aaacgctacg gtccgcgcgc     300

tctctggcaa gaggcaagag gtagcaacag cgagcgtgcc ggtcgctagt cgcgggtccc     360

cgagtgagca cgccagggag caggagacca aacgacgggg gtcggagtca gagtcgcagt     420

gggagtcccc ggaccggagc acgagcctga gcgggagagc gccgctcgca cgcccgtcgc     480

caccegcgta cccggcgcag ccagagccac cagcgcagcg ctgccatgga gcccagcagc     540
```

-continued

```
aagaagctga cgggtcgcct catgctggcc gtgggaggag cagtgcttgg ctccctgcag    600
tttggctaca acactggagt catcaatgcc ccccagaagg tgatcgagga gttctacaac    660
cagacatggg tccaccgcta tggggagagc atcctgccca ccacgctcac cacgctctgg    720
tccctctcag tggccatctt ttctgttggg ggcatgattg gctccttctc tgtgggcctt    780
ttcgttaacc gctttggccg gcggaattca atgctgatga tgaacctgct ggccttcgtg    840
tccgccgtgc tcatgggctt ctcgaaactg ggcaagtcct ttgagatgct gatcctgggc    900
cgcttcatca tcggtgtgta ctgcggcctg accacaggct tcgtgcccat gtatgtgggt    960
gaagtgtcac ccacagccct tcgtggggcc ctgggcaccc tgcaccagct gggcatcgtc   1020
gtcggcatcc tcatcgccca ggtgttcggc ctggactcca tcatgggcaa caaggacctg   1080
tggcccctgc tgctgagcat catcttcatc ccggccctgc tgcagtgcat cgtgctgccc   1140
ttctgccccg agagtccccg cttcctgctc atcaaccgca acgaggagaa ccgggccaag   1200
agtgtgctaa agaagctgcg cgggacagct gacgtgaccc atgacctgca ggagatgaag   1260
gaagagagtc ggcagatgat gcgggagaag aaggtcacca tcctggagct gttccgctcc   1320
cccgcctacc gccagcccat cctcatcgct gtggtgctgc agctgtccca gcagctgtct   1380
ggcatcaacg ctgtcttcta ttactccacg agcatcttcg agaaggcggg ggtgcagcag   1440
cctgtgtatg ccaccattgg ctccggtatc gtcaacacgg ccttcactgt cgtgtcgctg   1500
tttgtggtgg agcgagcagg ccggcggacc ctgcacctca taggcctcgc tggcatggcg   1560
ggttgtgcca tactcatgac catcgcgcta gcactgctgg agcagctacc ctggatgtcc   1620
tatctgagca tcgtggccat ctttggcttt gtggccttct ttgaagtggg tcctggcccc   1680
atcccatggt tcatcgtggc tgaactcttc agccagggtc cacgtccagc tgccattgcc   1740
gttgcaggct tctccaactg gacctcaaat ttcattgtgg gcatgtgctt ccagtatgtg   1800
gagcaactgt gtggtcccta cgtcttcatc atcttcactg tgctcctggt tctgttcttc   1860
atcttcacct acttcaaagt tcctgagact aaaggccgga ccttcgatga gatcgcttcc   1920
ggcttccggc aggggggagc cagccaaagt gacaagacac ccgaggagct gttccatccc   1980
ctgggggctg attcccaagt gtgagtcgcc ccagatcacc agcccggcct gctcccagca   2040
gccctaagga tctctcagga gcacaggcag ctggatgaga cttccaaacc tgacagatgt   2100
cagccgagcc gggcctgggg ctcctttctc cagccagcaa tgatgtccag aagaatattc   2160
aggacttaac ggctccagga ttttaacaaa agcaagactg ttgctcaaat ctattcagac   2220
aagcaacagg ttttataatt tttttattac tgattttgtt atttttatat cagcctgagt   2280
ctcctgtgcc cacatcccag gcttcaccct gaatggttcc atgcctgagg gtggagacta   2340
agccctgtcg agacacttgc cttcttcacc cagctaatct gtagggctgg acctatgtcc   2400
taaggacaca ctaatcgaac tatgaactac aaagcttcta tcccaggagg tggctatggc   2460
cacccgttct gctggcctgg atctccccac tctaggggtc aggctccatt aggatttgcc   2520
ccttcccatc tcttcctacc caaccactca aattaatctt tctttacctg agaccagttg   2580
ggagcactgg agtgcaggga ggagagggga agggccagtc tgggctgccg ggttctagtc   2640
tcctttgcac tgagggccac actattacca tgagaagagg gcctgtggga gcctgcaaac   2700
tcactgctca agaagacatg gagactcctg ccctgttgtg tatagatgca agatatttat   2760
atatattttt ggttgtcaat attaaataca gacactaagt tatagtatat ctggacaagc   2820
caacttgtaa atacaccacc tcactcctgt tacttaccta aacagatata aatggctggt   2880
```

-continued

```
ttttagaaac atggttttga aatgcttgtg gattgagggt aggaggtttg gatgggagtg   2940

agacagaagt aagtggggtt gcaaccactg caacggctta gacttcgact caggatccag   3000

tcccttacac gtacctctca tcagtgtcct cttgctcaaa aatctgtttg atccctgtta   3060

cccagagaat atatacattc tttatcttga cattcaaggc atttctatca catatttgat   3120

agttggtgtt caaaaaaaca ctagttttgt gccagccgtg atgctcaggc ttgaaatgca   3180

ttattttgaa tgtgaagtaa atactgtacc tttattggac aggctcaaag aggttatgtg   3240

cctgaagtcg cacagtgaat aagctaaaac acctgctttt aacaatggta ccatacaacc   3300

actactccat taactccacc cacctcctgc acccctcccc acacacacaa aatgaaccac   3360

gttctttgta tgggcccaat gagctgtcaa gctgccctgt gttcatttca tttggaattg   3420

ccccctctgg ttcctctgta tactactgct tcatctctaa agacagctca tcctcctcct   3480

tcacccctga atttccagag cacttcatct gctccttcat cacaagtcca gttttctgcc   3540

actagtctga atttcatgag aagatgccga tttggttcct gtgggtcctc agcactattc   3600

agtacagtgc ttgatgcaca gcaggcactc agaaaatact ggaggaaata aaacaccaaa   3660

gatatttgtc aaaaaaaaaa aaaaaaa                                       3687
```

<210> SEQ ID NO 2
<211> LENGTH: 492
<212> TYPE: PRT
<213> ORGANISM: Homo sapiens
<220> FEATURE:
<223> OTHER INFORMATION: GLUT1 amino acid

<400> SEQUENCE: 2

```
Met Glu Pro Ser Ser Lys Lys Leu Thr Gly Arg Leu Met Leu Ala Val
1               5                   10                  15

Gly Gly Ala Val Leu Gly Ser Leu Gln Phe Gly Tyr Asn Thr Gly Val
            20                  25                  30

Ile Asn Ala Pro Gln Lys Val Ile Glu Glu Phe Tyr Asn Gln Thr Trp
        35                  40                  45

Val His Arg Tyr Gly Glu Ser Ile Leu Pro Thr Thr Leu Thr Thr Leu
    50                  55                  60

Trp Ser Leu Ser Val Ala Ile Phe Ser Val Gly Gly Met Ile Gly Ser
65                  70                  75                  80

Phe Ser Val Gly Leu Phe Val Asn Arg Phe Gly Arg Arg Asn Ser Met
                85                  90                  95

Leu Met Met Asn Leu Leu Ala Phe Val Ser Ala Val Leu Met Gly Phe
            100                 105                 110

Ser Lys Leu Gly Lys Ser Phe Glu Met Leu Ile Leu Gly Arg Phe Ile
        115                 120                 125

Ile Gly Val Tyr Cys Gly Leu Thr Thr Gly Phe Val Pro Met Tyr Val
    130                 135                 140

Gly Glu Val Ser Pro Thr Ala Leu Arg Gly Ala Leu Gly Thr Leu His
145                 150                 155                 160

Gln Leu Gly Ile Val Val Gly Ile Leu Ile Ala Gln Val Phe Gly Leu
                165                 170                 175

Asp Ser Ile Met Gly Asn Lys Asp Leu Trp Pro Leu Leu Leu Ser Ile
            180                 185                 190

Ile Phe Ile Pro Ala Leu Leu Gln Cys Ile Val Leu Pro Phe Cys Pro
        195                 200                 205

Glu Ser Pro Arg Phe Leu Leu Ile Asn Arg Asn Glu Glu Asn Arg Ala
    210                 215                 220
```

-continued

```
Lys Ser Val Leu Lys Lys Leu Arg Gly Thr Ala Asp Val Thr His Asp
225                 230                 235                 240

Leu Gln Glu Met Lys Glu Glu Ser Arg Gln Met Met Arg Glu Lys Lys
                245                 250                 255

Val Thr Ile Leu Glu Leu Phe Arg Ser Pro Ala Tyr Arg Gln Pro Ile
            260                 265                 270

Leu Ile Ala Val Val Leu Gln Leu Ser Gln Gln Leu Ser Gly Ile Asn
        275                 280                 285

Ala Val Phe Tyr Tyr Ser Thr Ser Ile Phe Glu Lys Ala Gly Val Gln
    290                 295                 300

Gln Pro Val Tyr Ala Thr Ile Gly Ser Gly Ile Val Asn Thr Ala Phe
305                 310                 315                 320

Thr Val Val Ser Leu Phe Val Val Glu Arg Ala Gly Arg Arg Thr Leu
                325                 330                 335

His Leu Ile Gly Leu Ala Gly Met Ala Gly Cys Ala Ile Leu Met Thr
            340                 345                 350

Ile Ala Leu Ala Leu Leu Glu Gln Leu Pro Trp Met Ser Tyr Leu Ser
        355                 360                 365

Ile Val Ala Ile Phe Gly Phe Val Ala Phe Phe Glu Val Gly Pro Gly
    370                 375                 380

Pro Ile Pro Trp Phe Ile Val Ala Glu Leu Phe Ser Gln Gly Pro Arg
385                 390                 395                 400

Pro Ala Ala Ile Ala Val Ala Gly Phe Ser Asn Trp Thr Ser Asn Phe
                405                 410                 415

Ile Val Gly Met Cys Phe Gln Tyr Val Glu Gln Leu Cys Gly Pro Tyr
            420                 425                 430

Val Phe Ile Ile Phe Thr Val Leu Leu Val Leu Phe Phe Ile Phe Thr
        435                 440                 445

Tyr Phe Lys Val Pro Glu Thr Lys Gly Arg Thr Phe Asp Glu Ile Ala
    450                 455                 460

Ser Gly Phe Arg Gln Gly Gly Ala Ser Gln Ser Asp Lys Thr Pro Glu
465                 470                 475                 480

Glu Leu Phe His Pro Leu Gly Ala Asp Ser Gln Val
                485                 490


<210> SEQ ID NO 3
<211> LENGTH: 534
<212> TYPE: DNA
<213> ORGANISM: Artificial Sequence
<220> FEATURE:
<221> NAME/KEY: source
<222> LOCATION: 1..534
<223> OTHER INFORMATION: /mol_type="unassigned DNA"
      /note="HTLV2.RBD"
      /organism="Artificial sequence"

<400> SEQUENCE: 3

atgggtaatg ttttcttcct acttttattc agtctcacac attttccact agcccagcag     60

agccgatgca cactcacagt tggtatctcc tcctaccact ccagcccctg tagcccaacc    120

caacccgtct gcacgtggaa cctcgacctt aattccctaa caacggacca acgactacac    180

ccccccctgcc ctaacctaat tacttactct ggcttccata agacttattc cttatactta    240

ttcccacatt ggataaaaaa gccaaacaga cagggcctag ggtactactc gccttcctac    300

aatgaccctt gctcgctaca atgcccctac ttgggctgcc aatcatggac atgcccatac    360

acgggccccg tctccagtcc atcctggaag tttcattcag atgtaaattt cacccaggaa    420
```

```
gtcagccaag tgtcccttcg actacacttc tctaagtgcg gctcctccat gaccctccta    480

gtagatgccc ctggatatga tcctttatgg ttcatcacct cagaacccac tcag          534


<210> SEQ ID NO 4
<211> LENGTH: 224
<212> TYPE: PRT
<213> ORGANISM: Artificial Sequence
<220> FEATURE:
<223> OTHER INFORMATION: HTLV-2.RBD

<400> SEQUENCE: 4

Met Gly Asn Val Phe Phe Leu Leu Leu Phe Ser Leu Thr His Phe Pro
1               5                   10                  15

Leu Ala Gln Gln Ser Arg Cys Thr Leu Thr Val Gly Ile Ser Ser Tyr
            20                  25                  30

His Ser Ser Pro Cys Ser Pro Thr Gln Pro Val Cys Thr Trp Asn Leu
        35                  40                  45

Asp Leu Asn Ser Leu Thr Thr Asp Gln Arg Leu His Pro Pro Cys Pro
    50                  55                  60

Asn Leu Ile Thr Tyr Ser Gly Phe His Lys Thr Tyr Ser Leu Tyr Leu
65                  70                  75                  80

Phe Pro His Trp Ile Lys Lys Pro Asn Arg Gln Gly Leu Gly Tyr Tyr
                85                  90                  95

Ser Pro Ser Tyr Asn Asp Pro Cys Ser Leu Gln Cys Pro Tyr Leu Gly
            100                 105                 110

Cys Gln Ser Trp Thr Cys Pro Tyr Thr Gly Pro Val Ser Ser Pro Ser
        115                 120                 125

Trp Lys Phe His Ser Asp Val Asn Phe Thr Gln Glu Val Ser Gln Val
    130                 135                 140

Ser Leu Arg Leu His Phe Ser Lys Cys Gly Ser Ser Met Thr Leu Leu
145                 150                 155                 160

Val Asp Ala Pro Gly Tyr Asp Pro Leu Trp Phe Ile Thr Ser Glu Pro
                165                 170                 175

Thr Gln Pro Pro Pro Thr Ser Pro Pro Leu Val His Asp Ser Asp Leu
            180                 185                 190

Glu His Val Leu Thr Pro Ser Thr Ser Trp Thr Thr Lys Ile Leu Lys
        195                 200                 205

Phe Ile Gln Leu Thr Leu Gln Ser Thr Asn Tyr Ser Cys Met Val Cys
    210                 215                 220


<210> SEQ ID NO 5
<211> LENGTH: 178
<212> TYPE: PRT
<213> ORGANISM: Artificial Sequence
<220> FEATURE:
<223> OTHER INFORMATION: HTLV2.RBD

<400> SEQUENCE: 5

Met Gly Asn Val Phe Phe Leu Leu Leu Phe Ser Leu Thr His Phe Pro
1               5                   10                  15

Leu Ala Gln Gln Ser Arg Cys Thr Leu Thr Val Gly Ile Ser Ser Tyr
            20                  25                  30

His Ser Ser Pro Cys Ser Pro Thr Gln Pro Val Cys Thr Trp Asn Leu
        35                  40                  45

Asp Leu Asn Ser Leu Thr Thr Asp Gln Arg Leu His Pro Pro Cys Pro
    50                  55                  60
```

-continued

```
Asn Leu Ile Thr Tyr Ser Gly Phe His Lys Thr Tyr Ser Leu Tyr Leu
65                  70                  75                  80

Phe Pro His Trp Ile Lys Lys Pro Asn Arg Gln Gly Leu Gly Tyr Tyr
                85                  90                  95

Ser Pro Ser Tyr Asn Asp Pro Cys Ser Leu Gln Cys Pro Tyr Leu Gly
            100                 105                 110

Cys Gln Ser Trp Thr Cys Pro Tyr Thr Gly Pro Val Ser Ser Pro Ser
        115                 120                 125

Trp Lys Phe His Ser Asp Val Asn Phe Thr Gln Glu Val Ser Gln Val
    130                 135                 140

Ser Leu Arg Leu His Phe Ser Lys Cys Gly Ser Ser Met Thr Leu Leu
145                 150                 155                 160

Val Asp Ala Pro Gly Tyr Asp Pro Leu Trp Phe Ile Thr Ser Glu Pro
                165                 170                 175

Thr Gln


<210> SEQ ID NO 6
<211> LENGTH: 153
<212> TYPE: DNA
<213> ORGANISM: Artificial Sequence
<220> FEATURE:
<221> NAME/KEY: source
<222> LOCATION: 1..153
<223> OTHER INFORMATION: /mol_type="unassigned DNA"
      /note="HTLV2.RBD"
      /organism="Artificial Sequence"

<400> SEQUENCE: 6

ataagaaagc caaacagaca gggcctaggg tactactcgc cttcctacaa tgacccttgc     60

tcgctacaat gcccctactt gggctcccaa tcatggacat gcccatacac ggccccccgtc    120

tccactccat cctggaattt tcattcagat gta                                  153


<210> SEQ ID NO 7
<211> LENGTH: 51
<212> TYPE: PRT
<213> ORGANISM: Artificial Sequence
<220> FEATURE:
<223> OTHER INFORMATION: HTLV2.RBD

<400> SEQUENCE: 7

Ile Arg Lys Pro Asn Arg Gln Gly Leu Gly Tyr Tyr Ser Pro Ser Tyr
1               5                   10                  15

Asn Asp Pro Cys Ser Leu Gln Cys Pro Tyr Leu Gly Ser Gln Ser Trp
            20                  25                  30

Thr Cys Pro Tyr Thr Ala Pro Val Ser Thr Pro Ser Trp Asn Phe His
        35                  40                  45

Ser Asp Val
    50


<210> SEQ ID NO 8
<211> LENGTH: 924
<212> TYPE: DNA
<213> ORGANISM: Artificial Sequence
<220> FEATURE:
<221> NAME/KEY: source
<222> LOCATION: 1..924
<223> OTHER INFORMATION: /mol_type="unassigned DNA"
      /note="HTLV1.RBD"
      /organism="Artificial Sequence"

<400> SEQUENCE: 8
```

-continued

```
atgggtaagt ttctcgccac tttgatttta ttcttccagt tctgccccct catcctcggt     60

gattacagcc ccagctgctg tactctcaca attggagtct cctcatacca ctctaaaccc    120

tgcaatcctg cccagccagt ttgttcgtgg accctcgacc tgctggccct ttcagcggat    180

caggccctac agcccccctg ccctaatcta gtaagttact ccagctacca tgccacctat    240

tccctatatc tattccctca ttggattaaa aagccaaacc gaaatggcgg aggctattat    300

tcagcctctt attcagaccc ttgttcctta aagtgcccat acctggggtg ccaatcatgg    360

acctgcccct atacaggagc cgtctccagc ccctactgga agtttcagca agatgtcaat    420

tttactcaag aagtttcacg cctcaatatt aatctccatt tttcaaaatg cggttttccc    480

ttctcccttc tagtcgacgc tccaggatat gaccccatct ggttccttaa taccgaaccc    540

agccaactgc ctcccaccgc ccctcctcta ctcccccact ctaacctaga ccacatcctc    600

gagccctcta taccatggaa atcaaaactc ctgacccttg tccagttaac cctacaaagc    660

actaattata cttgcattgt ctgtatcgat cgtgccagcc tatccacttg gcacgtccta    720

tactctccca acgtctctgt tccatcctct tcttctaccc ccctccttta cccatcgtta    780

gcgcttccag ccccccacct gacgttacca tttaactgga cccactgctt tgacccccag    840

attcaagcta tagtctcctc cccctgtcat aactccctca tcctgccccc cttttccttg    900

tcacctgttc ccaccctagg atcc                                            924
```

<210> SEQ ID NO 9
<211> LENGTH: 308
<212> TYPE: PRT
<213> ORGANISM: Artificial Sequence
<220> FEATURE:
<223> OTHER INFORMATION: HTLV1.RBD

<400> SEQUENCE: 9

```
Met Gly Lys Phe Leu Ala Thr Leu Ile Leu Phe Phe Gln Phe Cys Pro
1               5                   10                  15

Leu Ile Leu Gly Asp Tyr Ser Pro Ser Cys Cys Thr Leu Thr Ile Gly
            20                  25                  30

Val Ser Ser Tyr His Ser Lys Pro Cys Asn Pro Ala Gln Pro Val Cys
        35                  40                  45

Ser Trp Thr Leu Asp Leu Leu Ala Leu Ser Ala Asp Gln Ala Leu Gln
    50                  55                  60

Pro Pro Cys Pro Asn Leu Val Ser Tyr Ser Ser Tyr His Ala Thr Tyr
65                  70                  75                  80

Ser Leu Tyr Leu Phe Pro His Trp Ile Lys Lys Pro Asn Arg Asn Gly
                85                  90                  95

Gly Gly Tyr Tyr Ser Ala Ser Tyr Ser Asp Pro Cys Ser Leu Lys Cys
            100                 105                 110

Pro Tyr Leu Gly Cys Gln Ser Trp Thr Cys Pro Tyr Thr Gly Ala Val
        115                 120                 125

Ser Ser Pro Tyr Trp Lys Phe Gln Gln Asp Val Asn Phe Thr Gln Glu
    130                 135                 140

Val Ser Arg Leu Asn Ile Asn Leu His Phe Ser Lys Cys Gly Phe Pro
145                 150                 155                 160

Phe Ser Leu Leu Val Asp Ala Pro Gly Tyr Asp Pro Ile Trp Phe Leu
                165                 170                 175

Asn Thr Glu Pro Ser Gln Leu Pro Pro Thr Ala Pro Pro Leu Leu Pro
            180                 185                 190

His Ser Asn Leu Asp His Ile Leu Glu Pro Ser Ile Pro Trp Lys Ser
```

```
        195                 200                 205

Lys Leu Leu Thr Leu Val Gln Leu Thr Leu Gln Ser Thr Asn Tyr Thr
    210                 215                 220

Cys Ile Val Cys Ile Asp Arg Ala Ser Leu Ser Thr Trp His Val Leu
225                 230                 235                 240

Tyr Ser Pro Asn Val Ser Val Pro Ser Ser Ser Ser Thr Pro Leu Leu
                245                 250                 255

Tyr Pro Ser Leu Ala Leu Pro Ala Pro His Leu Thr Leu Pro Phe Asn
            260                 265                 270

Trp Thr His Cys Phe Asp Pro Gln Ile Gln Ala Ile Val Ser Ser Pro
        275                 280                 285

Cys His Asn Ser Leu Ile Leu Pro Pro Phe Ser Leu Ser Pro Val Pro
    290                 295                 300

Thr Leu Gly Ser
305


<210> SEQ ID NO 10
<211> LENGTH: 228
<212> TYPE: PRT
<213> ORGANISM: Artificial Sequence
<220> FEATURE:
<223> OTHER INFORMATION: HTLV1.RBD

<400> SEQUENCE: 10

Met Gly Lys Phe Leu Ala Thr Leu Ile Leu Phe Phe Gln Phe Cys Pro
1               5                   10                  15

Leu Ile Phe Gly Asp Tyr Ser Pro Ser Cys Cys Thr Leu Thr Ile Gly
            20                  25                  30

Val Ser Ser Tyr His Ser Lys Pro Cys Asn Pro Ala Gln Pro Val Cys
        35                  40                  45

Ser Trp Thr Leu Asp Leu Leu Ala Leu Ser Ala Asp Gln Ala Leu Gln
    50                  55                  60

Pro Pro Cys Pro Asn Leu Val Ser Tyr Ser Ser Tyr His Ala Thr Tyr
65                  70                  75                  80

Ser Leu Tyr Leu Phe Pro His Trp Thr Lys Lys Pro Asn Arg Asn Gly
                85                  90                  95

Gly Gly Tyr Tyr Ser Ala Ser Tyr Ser Asp Pro Cys Ser Leu Lys Cys
            100                 105                 110

Pro Tyr Leu Gly Cys Gln Ser Trp Thr Cys Pro Tyr Thr Gly Ala Val
        115                 120                 125

Ser Ser Pro Tyr Trp Lys Phe Gln His Asp Val Asn Phe Thr Gln Glu
    130                 135                 140

Val Ser Arg Leu Asn Ile Asn Leu His Phe Ser Lys Cys Gly Phe Pro
145                 150                 155                 160

Phe Ser Leu Leu Val Asp Ala Pro Gly Tyr Asp Pro Ile Trp Phe Leu
                165                 170                 175

Asn Thr Glu Pro Ser Gln Leu Pro Pro Thr Ala Pro Pro Leu Leu Pro
            180                 185                 190

His Ser Asn Leu Asp His Ile Leu Glu Pro Ser Ile Pro Trp Lys Ser
        195                 200                 205

Lys Leu Leu Thr Leu Val Gln Leu Thr Leu Gln Ser Thr Asn Tyr Thr
    210                 215                 220

Cys Ile Val Cys
225
```

-continued

<210> SEQ ID NO 11
<211> LENGTH: 182
<212> TYPE: PRT
<213> ORGANISM: Artificial Sequence
<220> FEATURE:
<223> OTHER INFORMATION: HTLV1.RBD

<400> SEQUENCE: 11

```
Met Gly Lys Phe Leu Ala Thr Leu Ile Leu Phe Phe Gln Phe Cys Pro
1               5                   10                  15

Leu Ile Phe Gly Asp Tyr Ser Pro Ser Cys Cys Thr Leu Thr Ile Gly
            20                  25                  30

Val Ser Ser Tyr His Ser Lys Pro Cys Asn Pro Ala Gln Pro Val Cys
        35                  40                  45

Ser Trp Thr Leu Asp Leu Leu Ala Leu Ser Ala Asp Gln Ala Leu Gln
    50                  55                  60

Pro Pro Cys Pro Asn Leu Val Ser Tyr Ser Ser Tyr His Ala Thr Tyr
65                  70                  75                  80

Ser Leu Tyr Leu Phe Pro His Trp Thr Lys Lys Pro Asn Arg Asn Gly
                85                  90                  95

Gly Gly Tyr Tyr Ser Ala Ser Tyr Ser Asp Pro Cys Ser Leu Lys Cys
            100                 105                 110

Pro Tyr Leu Gly Cys Gln Ser Trp Thr Cys Pro Tyr Thr Gly Ala Val
        115                 120                 125

Ser Ser Pro Tyr Trp Lys Phe Gln His Asp Val Asn Phe Thr Gln Glu
    130                 135                 140

Val Ser Arg Leu Asn Ile Asn Leu His Phe Ser Lys Cys Gly Phe Pro
145                 150                 155                 160

Phe Ser Leu Leu Val Asp Ala Pro Gly Tyr Asp Pro Ile Trp Phe Leu
                165                 170                 175

Asn Thr Glu Pro Ser Gln
            180
```

<210> SEQ ID NO 12
<211> LENGTH: 153
<212> TYPE: DNA
<213> ORGANISM: Artificial Sequence
<220> FEATURE:
<221> NAME/KEY: source
<222> LOCATION: 1..153
<223> OTHER INFORMATION: /mol_type="unassigned DNA"
/note="HTLV1.RBD"
/organism="Artificial Sequence"

<400> SEQUENCE: 12

```
attaaaaagc caaacccaaa tggcggaggc tattatttag cctcttattc agacccttgt      60

tccttaaaat gcccatacct ggggtgccaa tcatggacct gcccctatac aggagccgtc     120

tccagcccct actggaagtt tcagcaagat gtc                                  153
```

<210> SEQ ID NO 13
<211> LENGTH: 51
<212> TYPE: PRT
<213> ORGANISM: Artificial Sequence
<220> FEATURE:
<223> OTHER INFORMATION: HTLV1.RBD

<400> SEQUENCE: 13

```
Ile Lys Lys Pro Asn Pro Asn Gly Gly Gly Tyr Tyr Leu Ala Ser Tyr
1               5                   10                  15

Ser Asp Pro Cys Ser Leu Lys Cys Pro Tyr Leu Gly Cys Gln Ser Trp
```

```
            20                  25                  30

Thr Cys Pro Tyr Thr Gly Ala Val Ser Ser Pro Tyr Trp Lys Phe Gln
        35                  40                  45

Gln Asp Val
    50


<210> SEQ ID NO 14
<211> LENGTH: 153
<212> TYPE: DNA
<213> ORGANISM: Artificial Sequence
<220> FEATURE:
<221> NAME/KEY: source
<222> LOCATION: 1..153
<223> OTHER INFORMATION: /mol_type="unassigned DNA"
      /note="HTLV1.RBD"
      /organism="Artificial Sequence"

<400> SEQUENCE: 14

gttaaaaagc caaaccgaaa tggcggaggc tattatttag cctcttattc agacccttgt     60

tccttaaaat gcccatacct ggggtgccaa tcatggacct gcccctatac aggagccgtc    120

tccagcccct actggaagtt tcagcaagat gtc                                 153


<210> SEQ ID NO 15
<211> LENGTH: 51
<212> TYPE: PRT
<213> ORGANISM: Artificial Sequence
<220> FEATURE:
<223> OTHER INFORMATION: HTLV1.RBD

<400> SEQUENCE: 15

Val Lys Lys Pro Asn Arg Asn Gly Gly Gly Tyr Tyr Leu Ala Ser Tyr
1               5                   10                  15

Ser Asp Pro Cys Ser Leu Lys Cys Pro Tyr Leu Gly Cys Gln Ser Trp
            20                  25                  30

Thr Cys Pro Tyr Thr Gly Ala Val Ser Ser Pro Tyr Trp Lys Phe Gln
        35                  40                  45

Gln Asp Val
    50


<210> SEQ ID NO 16
<211> LENGTH: 153
<212> TYPE: DNA
<213> ORGANISM: Artificial Sequence
<220> FEATURE:
<221> NAME/KEY: source
<222> LOCATION: 1..153
<223> OTHER INFORMATION: /mol_type="unassigned DNA"
      /note="HTLV1.RBD"
      /organism="Artificial Sequence"

<400> SEQUENCE: 16

attaaaaagc caaaccgaaa tggcggaggc tattatttag cctcttattc agacccttgt     60

tccttaaaat gcccatacct ggggtgccaa tcatggacct gcccctatac aggagccgtc    120

tccagcccct actggaagtt tcaacaagat gtc                                 153


<210> SEQ ID NO 17
<211> LENGTH: 51
<212> TYPE: PRT
<213> ORGANISM: Artificial Sequence
<220> FEATURE:
<223> OTHER INFORMATION: HTLV1.RBD

<400> SEQUENCE: 17
```

```
Ile Lys Lys Pro Asn Arg Asn Gly Gly Gly Tyr Tyr Leu Ala Ser Tyr
1               5                   10                  15

Ser Asp Pro Cys Ser Leu Lys Cys Pro Tyr Leu Gly Cys Gln Ser Trp
            20                  25                  30

Thr Cys Pro Tyr Thr Gly Ala Val Ser Ser Pro Tyr Trp Lys Phe Gln
        35                  40                  45

Gln Asp Val
    50


<210> SEQ ID NO 18
<211> LENGTH: 153
<212> TYPE: DNA
<213> ORGANISM: Artificial Sequence
<220> FEATURE:
<221> NAME/KEY: source
<222> LOCATION: 1..153
<223> OTHER INFORMATION: /mol_type="unassigned DNA"
      /note="HTLV1.RBD"
      /organism="Artificial Sequence"

<400> SEQUENCE: 18

attaaaaagc caaaccgaaa tggcggaggc tattatttag cctcttattc agacccttgt     60

tccttaaaat gcccatacct ggggtgccaa tcatggacct gcccctatac aggacccgtc    120

tccagcccct actggaagtt tcagcaagat gtc                                 153


<210> SEQ ID NO 19
<211> LENGTH: 51
<212> TYPE: PRT
<213> ORGANISM: Artificial Sequence
<220> FEATURE:
<223> OTHER INFORMATION: HTLV1.RBD

<400> SEQUENCE: 19

Ile Lys Lys Pro Asn Arg Asn Gly Gly Gly Tyr Tyr Leu Ala Ser Tyr
1               5                   10                  15

Ser Asp Pro Cys Ser Leu Lys Cys Pro Tyr Leu Gly Cys Gln Ser Trp
            20                  25                  30

Thr Cys Pro Tyr Thr Gly Pro Val Ser Ser Pro Tyr Trp Lys Phe Gln
        35                  40                  45

Gln Asp Val
    50


<210> SEQ ID NO 20
<211> LENGTH: 171
<212> TYPE: DNA
<213> ORGANISM: Artificial Sequence
<220> FEATURE:
<221> NAME/KEY: source
<222> LOCATION: 1..171
<223> OTHER INFORMATION: /mol_type="unassigned DNA"
      /note="HTLV1.RBD"
      /organism="Artificial Sequence"

<400> SEQUENCE: 20

attaaaaagc caaaccgaaa tggcggaggc tatcattcag cctcttattc agacccttgt     60

tccttaaagt gcccatacct ggggtgccaa tcatggacct gcccctatgc aggagccgtc    120

tccagcccct actggaagtt tcagcaagat gtcaatttta cccaggaagt a             171


<210> SEQ ID NO 21
<211> LENGTH: 57
<212> TYPE: PRT
```

```
<213> ORGANISM: Artificial Sequence
<220> FEATURE:
<223> OTHER INFORMATION: HTLV1.RBD

<400> SEQUENCE: 21

Ile Lys Lys Pro Asn Arg Asn Gly Gly Gly Tyr His Ser Ala Ser Tyr
1               5                   10                  15

Ser Asp Pro Cys Ser Leu Lys Cys Pro Tyr Leu Gly Cys Gln Ser Trp
            20                  25                  30

Thr Cys Pro Tyr Ala Gly Ala Val Ser Ser Pro Tyr Trp Lys Phe Gln
        35                  40                  45

Gln Asp Val Asn Phe Thr Gln Glu Val
    50                  55


<210> SEQ ID NO 22
<211> LENGTH: 224
<212> TYPE: PRT
<213> ORGANISM: Artificial Sequence
<220> FEATURE:
<223> OTHER INFORMATION: HTLV4.RBD

<400> SEQUENCE: 22

Met Gly Asn Val Leu Phe Leu Thr Leu Leu Ala Thr Leu Gly Ile Pro
1               5                   10                  15

Val Leu Gln Ala Ser Arg Cys Thr Ile Thr Val Gly Ile Ser Ser Tyr
            20                  25                  30

His Ser Ser Pro Cys Ser Pro Ala Gln Pro Leu Cys Thr Trp Ala Leu
        35                  40                  45

Asp Leu Val Ser Ile Thr Lys Asp Gln Leu Leu Tyr Pro Pro Cys Gln
    50                  55                  60

Asn Leu Ile Thr Tyr Ser Asn Tyr His Lys Thr Tyr Ser Leu Tyr Leu
65                  70                  75                  80

Phe Pro His Trp Val Gln Lys Pro Leu Arg Arg Gly Leu Gly Tyr Tyr
                85                  90                  95

Ser Ala Ser Tyr Ser Asp Pro Cys Ser Leu Gln Cys Pro Tyr Leu Gly
            100                 105                 110

Ser Gln Ser Trp Thr Cys Pro Tyr Thr Gly Pro Val Ser Ser Pro Thr
        115                 120                 125

Trp Arg Phe Ser Thr Asp Val Asn Phe Thr Gln Glu Val Ser Arg Val
    130                 135                 140

Ser Leu Lys Leu His Phe Ser Lys Cys Gly Ser Ser Leu Thr Leu Leu
145                 150                 155                 160

Ile Asp Ala Pro Gly Tyr Asp Pro Leu Trp Tyr Leu Thr Ser Glu Pro
                165                 170                 175

Thr Gln Glu Pro Pro Thr Pro Pro Pro Leu Val Ser Asp Ser Asp Leu
            180                 185                 190

Glu His Val Leu Thr Pro Ser Ala Ser Trp Ala Ser Lys Met Leu Thr
        195                 200                 205

Leu Ile His Leu Thr Leu Gln Ser Thr Asn Tyr Ser Cys Met Val Cys
    210                 215                 220


<210> SEQ ID NO 23
<211> LENGTH: 178
<212> TYPE: PRT
<213> ORGANISM: Artificial Sequence
<220> FEATURE:
<223> OTHER INFORMATION: HTLV4.RBD

<400> SEQUENCE: 23
```

```
Met Gly Asn Val Leu Phe Leu Thr Leu Leu Ala Thr Leu Gly Ile Pro
1               5                   10                  15

Val Leu Gln Ala Ser Arg Cys Thr Ile Thr Val Gly Ile Ser Ser Tyr
            20                  25                  30

His Ser Ser Pro Cys Ser Pro Ala Gln Pro Leu Cys Thr Trp Ala Leu
        35                  40                  45

Asp Leu Val Ser Ile Thr Lys Asp Gln Leu Leu Tyr Pro Pro Cys Gln
    50                  55                  60

Asn Leu Ile Thr Tyr Ser Asn Tyr His Lys Thr Tyr Ser Leu Tyr Leu
65                  70                  75                  80

Phe Pro His Trp Val Gln Lys Pro Leu Arg Arg Gly Leu Gly Tyr Tyr
                85                  90                  95

Ser Ala Ser Tyr Ser Asp Pro Cys Ser Leu Gln Cys Pro Tyr Leu Gly
            100                 105                 110

Ser Gln Ser Trp Thr Cys Pro Tyr Thr Gly Pro Val Ser Ser Pro Thr
        115                 120                 125

Trp Arg Phe Ser Thr Asp Val Asn Phe Thr Gln Glu Val Ser Arg Val
    130                 135                 140

Ser Leu Lys Leu His Phe Ser Lys Cys Gly Ser Ser Leu Thr Leu Leu
145                 150                 155                 160

Ile Asp Ala Pro Gly Tyr Asp Pro Leu Trp Tyr Leu Thr Ser Glu Pro
                165                 170                 175

Thr Gln


<210> SEQ ID NO 24
<211> LENGTH: 1467
<212> TYPE: DNA
<213> ORGANISM: Artificial Sequence
<220> FEATURE:
<221> NAME/KEY: source
<222> LOCATION: 1..1467
<223> OTHER INFORMATION: /mol_type="unassigned DNA"
      /note="STLV1.RBD"
      /organism="Artificial Sequence"

<400> SEQUENCE: 24

atgggtaagt ttctcgccac tttgatttta ttcttccagt tctgcccct cattctcggt      60

gattacagcc ccagctgctg tactctcaca attggagtct cctcatacct ctctaaaccc    120

tgcaatcctg cccagccagt ttgttcatgg accctcgacc tactggccct ttcagcagac    180

caagccctac agcccccctg ccctaatcta gtaagttact ccagctacca tgccacctat    240

tccctatatc tattccctca ttggattaaa aagccaaacc gaaatggcgg aggctattat    300

tcggcctctt attcagaccc atgttcttta aagtgcccat acttagggtg ccaatcatgg    360

acctgcccct atacaggagt cgtctccagc ccctattgga aatttcagca agatgtcaat    420

tttactcaag aagtttcaca cctcaatatt aatctccatt tctcaaaatg cggttttccc    480

ttctcccttc taatcgacgc tccaggatat gaccccatct ggttccttaa taccgaaccc    540

agccaactgc ctcccaccgc ccctcctcta ctcccccact ctaacctgga ccacatcctc    600

gagccctcta taccatggaa atcaaaactt ctgactcttg tccagctaac cctacaaagc    660

actaattaca cttgcatcgt ctgtatagac cgtgccagcc tctctacttg gcatgtcctg    720

tactctccca acgtctctgt tccgtcctct tcttctaccc ccctccttta cccgtcgtta    780

gcgcttccag ctccccacct gacgctacca tttaactgga cccactgctt tgacccccag    840

attcaagcta tagtctcctc cccctgtcat aactccctca tcctgccccc cttttccttg    900
```

```
tcacctgttc ccaccctagg atcccgctcc cgccgagcgg taccggtggc ggtctggctt    960

gtctccgccc tggccatggg agccggaatt gctggcggga ttaccggctc catgtccctc   1020

gcctcaggaa agagcctcct acatgaggtg gacaaagata tttcccaatt aactcaagca   1080

atagtcaaaa accacaaaaa tctactcaaa attgcacagt atgctgccca gaacaggcga   1140

ggccttgatc tcctgttctg ggagcaagga ggattatgca aagcattaca agaacagtgc   1200

tgttttctaa atattaccaa ttcccatgtc tcaatactac aagaaagacc ccccttgag    1260

aatcgagtcc tcactggctg gggccttaac tgggaccttg gcctctcaca gtgggctcga   1320

gaggccttac aaactgggat cacccttgtt gcactactcc ttctcgttat ccttgcagga   1380

ccatgcatcc tccgtcagct gcgacacctc ccctcgcgcg tcagataccc ccattattct   1440

cttataaacc ctgagtcatc cctgtaa                                       1467


<210> SEQ ID NO 25
<211> LENGTH: 488
<212> TYPE: PRT
<213> ORGANISM: Artificial Sequence
<220> FEATURE:
<223> OTHER INFORMATION: STLV1.RBD

<400> SEQUENCE: 25

Met Gly Lys Phe Leu Ala Thr Leu Ile Leu Phe Phe Gln Phe Cys Pro
1               5                   10                  15

Leu Ile Leu Gly Asp Tyr Ser Pro Ser Cys Cys Thr Leu Thr Ile Gly
            20                  25                  30

Val Ser Ser Tyr Leu Ser Lys Pro Cys Asn Pro Ala Gln Pro Val Cys
        35                  40                  45

Ser Trp Thr Leu Asp Leu Leu Ala Leu Ser Ala Asp Gln Ala Leu Gln
    50                  55                  60

Pro Pro Cys Pro Asn Leu Val Ser Tyr Ser Ser Tyr His Ala Thr Tyr
65                  70                  75                  80

Ser Leu Tyr Leu Phe Pro His Trp Ile Lys Lys Pro Asn Arg Asn Gly
                85                  90                  95

Gly Gly Tyr Tyr Ser Ala Ser Tyr Ser Asp Pro Cys Ser Leu Lys Cys
            100                 105                 110

Pro Tyr Leu Gly Cys Gln Ser Trp Thr Cys Pro Tyr Thr Gly Val Val
        115                 120                 125

Ser Ser Pro Tyr Trp Lys Phe Gln Gln Asp Val Asn Phe Thr Gln Glu
    130                 135                 140

Val Ser His Leu Asn Ile Asn Leu His Phe Ser Lys Cys Gly Phe Pro
145                 150                 155                 160

Phe Ser Leu Leu Ile Asp Ala Pro Gly Tyr Asp Pro Ile Trp Phe Leu
                165                 170                 175

Asn Thr Glu Pro Ser Gln Leu Pro Pro Thr Ala Pro Pro Leu Leu Pro
            180                 185                 190

His Ser Asn Leu Asp His Ile Leu Glu Pro Ser Ile Pro Trp Lys Ser
        195                 200                 205

Lys Leu Leu Thr Leu Val Gln Leu Thr Leu Gln Ser Thr Asn Tyr Thr
    210                 215                 220

Cys Ile Val Cys Ile Asp Arg Ala Ser Leu Ser Thr Trp His Val Leu
225                 230                 235                 240

Tyr Ser Pro Asn Val Ser Val Pro Ser Ser Ser Ser Thr Pro Leu Leu
                245                 250                 255
```

-continued

```
Tyr Pro Ser Leu Ala Leu Pro Ala Pro His Leu Thr Leu Pro Phe Asn
            260                 265                 270

Trp Thr His Cys Phe Asp Pro Gln Ile Gln Ala Ile Val Ser Ser Pro
        275                 280                 285

Cys His Asn Ser Leu Ile Leu Pro Pro Phe Ser Leu Ser Pro Val Pro
    290                 295                 300

Thr Leu Gly Ser Arg Ser Arg Arg Ala Val Pro Val Ala Val Trp Leu
305                 310                 315                 320

Val Ser Ala Leu Ala Met Gly Ala Gly Ile Ala Gly Gly Ile Thr Gly
                325                 330                 335

Ser Met Ser Leu Ala Ser Gly Lys Ser Leu Leu His Glu Val Asp Lys
            340                 345                 350

Asp Ile Ser Gln Leu Thr Gln Ala Ile Val Lys Asn His Lys Asn Leu
        355                 360                 365

Leu Lys Ile Ala Gln Tyr Ala Ala Gln Asn Arg Arg Gly Leu Asp Leu
    370                 375                 380

Leu Phe Trp Glu Gln Gly Gly Leu Cys Lys Ala Leu Gln Glu Gln Cys
385                 390                 395                 400

Cys Phe Leu Asn Ile Thr Asn Ser His Val Ser Ile Leu Gln Glu Arg
                405                 410                 415

Pro Pro Leu Glu Asn Arg Val Leu Thr Gly Trp Gly Leu Asn Trp Asp
            420                 425                 430

Leu Gly Leu Ser Gln Trp Ala Arg Glu Ala Leu Gln Thr Gly Ile Thr
        435                 440                 445

Leu Val Ala Leu Leu Leu Leu Val Ile Leu Ala Gly Pro Cys Ile Leu
    450                 455                 460

Arg Gln Leu Arg His Leu Pro Ser Arg Val Arg Tyr Pro His Tyr Ser
465                 470                 475                 480

Leu Ile Asn Pro Glu Ser Ser Leu
                485
```

<210> SEQ ID NO 26
<211> LENGTH: 1461
<212> TYPE: DNA
<213> ORGANISM: Artificial Sequence
<220> FEATURE:
<221> NAME/KEY: source
<222> LOCATION: 1..1461
<223> OTHER INFORMATION: /mol_type="unassigned DNA"
/note="STLV2.RBD"
/organism="Artificial Sequence"

<400> SEQUENCE: 26

```
atgggtaaga taattgcttt ccttttattc catcttacat gtatcacaat cactaaacag     60

agccggtgca cgcttacggt aggtgtctcc tcgtatcact ctagtccctg cagtcttgcc    120

caacctatct gcacctggga tctcgacctt cattccttaa ctacagacca acgtctgtac    180

cctccatgcc ccaatctagt ttcttactct aacttccaca agtcctactc cttatatttg    240

ttcccgcact gggtaaaaaa gccaaataga caaggcctgg gatactattc tgcatcctac    300

agcgacccct gctcgctcca gtgcccttat ttaggaagcc agtcttggac atgcccttac    360

accggcccca tctccagccc gtcttggagg ttccaccgag atgttaactt cacccaagag    420

gtcaaccatg taaccctccg gctacacttc tcccgatgtg gctcttctat gaccctcctc    480

atagacgccc caggctacga ccccctgtgg ttcatctctt cggaacccac tcagcccccc    540

cccacttccc caccattagt ccgcgactct gaccttgaac atatcttaac cccctcctcc    600
```

```
tcctgggcta ctaggatgct aaccctcatc caactaactc tacaaagtac caattattct    660

tgcatggttt gtatagacag aaccagcttg tcgtcctggc acgtactcta taccccctaat    720

atctctgcct cacctggggg cgactccttg cctatacttt atccctcctt ggccctaccg    780

gccccccaac cccagccgtt ttcctggtct cactgttacc agccccacct acaggcagta    840

actacagcca attgcaacaa ttccattgtc ctgcccccat tctctctcac cccggtgcct    900

tcccctggga caagaagccg ccgggctatt ccagtggctg tatggctcgt ctcagcccta    960

gcggccggga ctggtattgc agggggaata accggatccc tgtccctagc atcaagccgc   1020

agcctgcttt ttgaagttga caaagatatt tcccacctca cacaagccat cgttaaaaac   1080

catcaaaaca tcctccgcgt agcacaatat gcagcccaaa atagaagagg actagacctc   1140

ctgttttggg aacaaggagg cctctgcaaa gccatacaag agcaatgttg cttccttaac   1200

atcagcaaca cccatgtgtc cgtccttcag gagcgccccc ccctggaaaa gagagtcatc   1260

acaggatggg gtctcaactg ggacctaggg ctatcccaat gggcacggga agcactccaa   1320

actggtataa ccatcctagc cttgctcctc cttgtcatac tgttcggtcc ttgtatcctt   1380

cgccaactcc aatcacttcc ccaccggcta cagaacaggc acaaccaata ctctcttatt   1440

aaccaggaaa ccacactata a                                             1461
```

<210> SEQ ID NO 27
<211> LENGTH: 486
<212> TYPE: PRT
<213> ORGANISM: Artificial Sequence
<220> FEATURE:
<223> OTHER INFORMATION: STV2.RBD

<400> SEQUENCE: 27

```
Met Gly Lys Ile Ile Ala Phe Leu Leu Phe His Leu Thr Cys Ile Thr
1               5                   10                  15

Ile Thr Lys Gln Ser Arg Cys Thr Leu Thr Val Gly Val Ser Ser Tyr
            20                  25                  30

His Ser Ser Pro Cys Ser Leu Ala Gln Pro Ile Cys Thr Trp Asp Leu
        35                  40                  45

Asp Leu His Ser Leu Thr Thr Asp Gln Arg Leu Tyr Pro Pro Cys Pro
    50                  55                  60

Asn Leu Val Ser Tyr Ser Asn Phe His Lys Ser Tyr Ser Leu Tyr Leu
65                  70                  75                  80

Phe Pro His Trp Val Lys Lys Pro Asn Arg Gln Gly Leu Gly Tyr Tyr
                85                  90                  95

Ser Ala Ser Tyr Ser Asp Pro Cys Ser Leu Gln Cys Pro Tyr Leu Gly
            100                 105                 110

Ser Gln Ser Trp Thr Cys Pro Tyr Thr Gly Pro Ile Ser Ser Pro Ser
        115                 120                 125

Trp Arg Phe His Arg Asp Val Asn Phe Thr Gln Glu Val Asn His Val
    130                 135                 140

Thr Leu Arg Leu His Phe Ser Arg Cys Gly Ser Ser Met Thr Leu Leu
145                 150                 155                 160

Ile Asp Ala Pro Gly Tyr Asp Pro Leu Trp Phe Ile Ser Ser Glu Pro
                165                 170                 175

Thr Gln Pro Pro Pro Thr Ser Pro Pro Leu Val Arg Asp Ser Asp Leu
            180                 185                 190

Glu His Ile Leu Thr Pro Ser Ser Ser Trp Ala Thr Arg Met Leu Thr
        195                 200                 205
```

-continued

```
Leu Ile Gln Leu Thr Leu Gln Ser Thr Asn Tyr Ser Cys Met Val Cys
    210                 215                 220

Ile Asp Arg Thr Ser Leu Ser Ser Trp His Val Leu Tyr Thr Pro Asn
225                 230                 235                 240

Ile Ser Ala Ser Pro Gly Gly Asp Ser Leu Pro Ile Leu Tyr Pro Ser
                245                 250                 255

Leu Ala Leu Pro Ala Pro Gln Pro Gln Pro Phe Ser Trp Ser His Cys
            260                 265                 270

Tyr Gln Pro His Leu Gln Ala Val Thr Thr Ala Asn Cys Asn Asn Ser
        275                 280                 285

Ile Val Leu Pro Pro Phe Ser Leu Thr Pro Val Pro Ser Pro Gly Thr
    290                 295                 300

Arg Ser Arg Arg Ala Ile Pro Val Ala Val Trp Leu Val Ser Ala Leu
305                 310                 315                 320

Ala Ala Gly Thr Gly Ile Ala Gly Gly Ile Thr Gly Ser Leu Ser Leu
                325                 330                 335

Ala Ser Ser Arg Ser Leu Leu Phe Glu Val Asp Lys Asp Ile Ser His
            340                 345                 350

Leu Thr Gln Ala Ile Val Lys Asn His Gln Asn Ile Leu Arg Val Ala
        355                 360                 365

Gln Tyr Ala Ala Gln Asn Arg Arg Gly Leu Asp Leu Leu Phe Trp Glu
    370                 375                 380

Gln Gly Gly Leu Cys Lys Ala Ile Gln Glu Gln Cys Cys Phe Leu Asn
385                 390                 395                 400

Ile Ser Asn Thr His Val Ser Val Leu Gln Glu Arg Pro Pro Leu Glu
                405                 410                 415

Lys Arg Val Ile Thr Gly Trp Gly Leu Asn Trp Asp Leu Gly Leu Ser
            420                 425                 430

Gln Trp Ala Arg Glu Ala Leu Gln Thr Gly Ile Thr Ile Leu Ala Leu
        435                 440                 445

Leu Leu Leu Val Ile Leu Phe Gly Pro Cys Ile Leu Arg Gln Leu Gln
    450                 455                 460

Ser Leu Pro His Arg Leu Gln Asn Arg His Asn Gln Tyr Ser Leu Ile
465                 470                 475                 480

Asn Gln Glu Thr Thr Leu
                485
```

<210> SEQ ID NO 28
<211> LENGTH: 930
<212> TYPE: DNA
<213> ORGANISM: Artificial Sequence
<220> FEATURE:
<221> NAME/KEY: source
<222> LOCATION: 1..930
<223> OTHER INFORMATION: /mol_type="unassigned DNA"
/note="STLV3.RBD"
/organism="Artificial Sequence"

<400> SEQUENCE: 28

```
atgggtaagt ttggccttta ttgtcttgtt cacctttaca tacttctccc tgcctcctct     60

ggcaatccca gtcggtgcac cctgttcata ggggcctctt cctaccactc cagcccttgc    120

gggtccagcc tcccacggtg tacctggaat cttgacctat tctccctcac gaaagatcaa    180

agcctaagcc ccccatgtcc agacttaatt acttactcac aataccacaa gccctactcc    240

ctgtatgtat tccctcattg gataactaaa cctaaccgcc ggggcttagg ttactattcc    300

gcttcctact cagacccctg tgccatacag tgcccttacc tgggatgcca gtcgtggaca    360
```

-continued

```
tgcccctata cgggcccggt gtccagtccg cattggagat acacctatga tcttaacttt    420

acccaggagg tatcatccgt ctccttacac ttgcatttct ccaaatgcgg atcctcgttc    480

tcctttctac tagacgcacc aggatatgac ccagtgtggt tcctctcctc ccaggccaca    540

caggctccac ccacacctgc ccctctcata cgggactcag atctccagta cattctagaa    600

ccgcccattc cgtggagctc taagattctt aaccttatcc tcctcaccct aaaaagcact    660

aactattctt gcatggtctg tgttgaccgc tccagcctat cctcatggca tgtcctgtat    720

ggacccactc aagtccccag tccacccgac ccccaagccc ggtctatcct gcgacctgcc    780

ttagctattc ccgccagtaa tatcaccccc ccgtttcctt ggacccattg ctatcgccct    840

cctccgcaag ccatctcctc ggagaattgt aacaactctg tagtgctgcc cccttttct    900

ctgtctccaa ttcctaacgt ctccagaccc                                       930
```

<210> SEQ ID NO 29
<211> LENGTH: 310
<212> TYPE: PRT
<213> ORGANISM: Artificial Sequence
<220> FEATURE:
<223> OTHER INFORMATION: STLV3.RBD

<400> SEQUENCE: 29

```
Met Gly Lys Phe Gly Leu Tyr Cys Leu Val His Leu Tyr Ile Leu Leu
1               5                   10                  15

Pro Ala Ser Ser Gly Asn Pro Ser Arg Cys Thr Leu Phe Ile Gly Ala
            20                  25                  30

Ser Ser Tyr His Ser Ser Pro Cys Gly Ser Ser Leu Pro Arg Cys Thr
        35                  40                  45

Trp Asn Leu Asp Leu Phe Ser Leu Thr Lys Asp Gln Ser Leu Ser Pro
    50                  55                  60

Pro Cys Pro Asp Leu Ile Thr Tyr Ser Gln Tyr His Lys Pro Tyr Ser
65                  70                  75                  80

Leu Tyr Val Phe Pro His Trp Ile Thr Lys Pro Asn Arg Arg Gly Leu
                85                  90                  95

Gly Tyr Tyr Ser Ala Ser Tyr Ser Asp Pro Cys Ala Ile Gln Cys Pro
            100                 105                 110

Tyr Leu Gly Cys Gln Ser Trp Thr Cys Pro Tyr Thr Gly Pro Val Ser
        115                 120                 125

Ser Pro His Trp Arg Tyr Thr Tyr Asp Leu Asn Phe Thr Gln Glu Val
    130                 135                 140

Ser Ser Val Ser Leu His Leu His Phe Ser Lys Cys Gly Ser Ser Phe
145                 150                 155                 160

Ser Phe Leu Leu Asp Ala Pro Gly Tyr Asp Pro Val Trp Phe Leu Ser
                165                 170                 175

Ser Gln Ala Thr Gln Ala Pro Pro Thr Pro Ala Pro Leu Ile Arg Asp
            180                 185                 190

Ser Asp Leu Gln Tyr Ile Leu Glu Pro Pro Ile Pro Trp Ser Ser Lys
        195                 200                 205

Ile Leu Asn Leu Ile Leu Leu Thr Leu Lys Ser Thr Asn Tyr Ser Cys
    210                 215                 220

Met Val Cys Val Asp Arg Ser Ser Leu Ser Ser Trp His Val Leu Tyr
225                 230                 235                 240

Gly Pro Thr Gln Val Pro Ser Pro Pro Asp Pro Gln Ala Arg Ser Ile
                245                 250                 255
```

```
Leu Arg Pro Ala Leu Ala Ile Pro Ala Ser Asn Ile Thr Pro Pro Phe
            260                 265                 270

Pro Trp Thr His Cys Tyr Arg Pro Pro Pro Gln Ala Ile Ser Ser Glu
        275                 280                 285

Asn Cys Asn Asn Ser Val Val Leu Pro Pro Phe Ser Leu Ser Pro Ile
    290                 295                 300

Pro Asn Val Ser Arg Pro
305                 310


<210> SEQ ID NO 30
<211> LENGTH: 228
<212> TYPE: PRT
<213> ORGANISM: Artificial Sequence
<220> FEATURE:
<223> OTHER INFORMATION: Rabbit Fc fragment

<400> SEQUENCE: 30

Ala Pro Ser Thr Cys Ser Lys Pro Thr Cys Pro Pro Pro Glu Leu Leu
1               5                   10                  15

Gly Gly Pro Ser Val Phe Ile Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Asp Asp Pro Glu Val Gln Phe Thr Trp Tyr Ile Asn Asn Glu Gln
    50                  55                  60

Val Arg Thr Ala Arg Pro Pro Leu Arg Glu Gln Gln Phe Asp Cys Thr
65                  70                  75                  80

Ile Arg Val Val Ser Thr Leu Pro Ile Ala His Gln Asp Trp Leu Arg
                85                  90                  95

Gly Lys Glu Phe Lys Cys Lys Val His Asn Lys Ala Leu Pro Ala Pro
            100                 105                 110

Ile Glu Lys Thr Ile Ser Lys Ala Arg Gly Gln Pro Leu Glu Pro Lys
        115                 120                 125

Val Tyr Thr Met Gly Pro Pro Arg Glu Glu Leu Ser Ser Arg Ser Val
    130                 135                 140

Ser Leu Thr Cys Met Ile Asn Gly Phe Tyr Pro Ser Asp Ile Ser Val
145                 150                 155                 160

Glu Trp Glu Lys Asn Gly Lys Ala Glu Asp Asn Tyr Lys Thr Thr Pro
                165                 170                 175

Ala Val Leu Asp Ser Asp Gly Ser Tyr Phe Leu Tyr Ser Lys Leu Ser
            180                 185                 190

Val Pro Thr Ser Glu Trp Gln Arg Gly Asp Val Phe Thr Cys Ser Val
        195                 200                 205

Met His Glu Ala Leu His Asn His Tyr Thr Gln Lys Ser Ile Ser Arg
    210                 215                 220

Ser Pro Gly Lys
225


<210> SEQ ID NO 31
<211> LENGTH: 687
<212> TYPE: DNA
<213> ORGANISM: Artificial Sequence
<220> FEATURE:
<221> NAME/KEY: source
<222> LOCATION: 1..687
<223> OTHER INFORMATION: /mol_type="unassigned DNA"
      /note="Rabbit Fc fragment"
      /organism="Artificial Sequence"
```

-continued

<400> SEQUENCE: 31

```
gcaccctcga catgcagcaa gcccacgtgc ccaccccctg aactcctggg gggaccgtct     60

gtcttcatct tcccccaaa acccaaggac accctcatga tctcacgcac ccccgaggtc    120

acatgcgtgg tggtggacgt gagccaggat gaccccgagg tgcagttcac atggtacata    180

aacaacgagc aggtgcgcac cgcccggccg ccgctacggg agcagcagtt caacagcacg    240

atccgcgtgg tcagcaccct ccccatcacg caccaggact ggctgagggg caaggagttc    300

aagtgcaaag tccacaacaa ggcactcccg gcccccatcg agaaaaccat ctccaaagcc    360

agagggcagc ccctggagcc gaaggtctac accatgggcc ctccccggga ggagctgagc    420

agcaggtcgg tcagcctgac ctgcatgatc aacggcttct acccttccga catctcggtg    480

gagtgggaga agaacgggaa ggcagaggac aactacaaga ccacgccggc cgtgctggac    540

agcgacggct cctacttcct ctacaacaag ctctcagtgc ccacgagtga gtggcagcgg    600

ggcgacgtct tcacctgctc cgtgatgcac gaggccttgc acaaccacta cacgcagaag    660

tccatctccc gctctccggg taaatga                                        687
```

<210> SEQ ID NO 32
<211> LENGTH: 229
<212> TYPE: PRT
<213> ORGANISM: Artificial Sequence
<220> FEATURE:
<223> OTHER INFORMATION: Mouse Fc fragment

<400> SEQUENCE: 32

```
Val Asp Val Pro Arg Asp Cys Gly Cys Lys Pro Cys Ile Cys Thr Val
1               5                   10                  15

Pro Glu Val Ser Ser Val Phe Ile Phe Pro Pro Lys Pro Lys Asp Val
            20                  25                  30

Leu Thr Ile Thr Leu Thr Pro Lys Val Thr Cys Val Val Val Asp Ile
        35                  40                  45

Ser Lys Asp Asp Pro Glu Val Gln Phe Ser Trp Phe Val Asp Asp Val
    50                  55                  60

Glu Val His Thr Ala Gln Thr Gln Pro Arg Glu Glu Gln Phe Asn Ser
65                  70                  75                  80

Thr Phe Arg Ser Val Ser Glu Leu Pro Ile Met His Gln Asp Trp Leu
                85                  90                  95

Asn Gly Lys Glu Phe Lys Cys Arg Val Asn Ser Ala Ala Phe Pro Ala
            100                 105                 110

Pro Ile Glu Lys Thr Ile Ser Lys Thr Lys Gly Arg Pro Lys Ala Pro
        115                 120                 125

Gln Val Tyr Thr Ile Pro Pro Pro Lys Glu Gln Met Ala Lys Asp Lys
    130                 135                 140

Val Ser Leu Thr Cys Met Ile Thr Asp Phe Phe Pro Glu Asp Ile Thr
145                 150                 155                 160

Val Glu Trp Gln Trp Asn Gly Gln Pro Ala Glu Asn Tyr Lys Asn Thr
                165                 170                 175

Gln Pro Ile Met Asp Thr Asp Gly Ser Tyr Phe Val Tyr Ser Lys Leu
            180                 185                 190

Asn Val Gln Lys Ser Asn Trp Glu Ala Gly Asn Thr Phe Thr Cys Ser
        195                 200                 205

Val Leu His Glu Gly Leu His Asn His His Thr Glu Lys Ser Leu Ser
    210                 215                 220

His Ser Pro Gly Lys
```

-continued

225

<210> SEQ ID NO 33
<211> LENGTH: 690
<212> TYPE: DNA
<213> ORGANISM: Artificial Sequence
<220> FEATURE:
<221> NAME/KEY: source
<222> LOCATION: 1..690
<223> OTHER INFORMATION: /mol_type="unassigned DNA"
/note="Mouse Fc fragment"
/organism="Artificial Sequence"

<400> SEQUENCE: 33
gtcgacgtgc ccagggattg tggttgtaag ccttgcatat gtacagtccc agaagtatca 60
tctgtcttca tcttcccccc aaagcccaag gatgtgctca ccattactct gactcctaag 120
gtcacgtgtg ttgtggtaga catcagcaag gatgatcccg aggtccagtt cagctggttt 180
gtagatgatg tggaggtgca cacagctcag acgcaacccc gggaggagca gttcaacagc 240
actttccgct cagtcagtga acttcccatc atgcaccagg actggctcaa tggcaaggag 300
ttcaaatgca gggtcaacag tgcagctttc cctgccccca tcgagaaaac catctccaaa 360
accaaaggca gaccgaaggc tccacaggtg tacaccattc cacctcccaa ggagcagatg 420
gccaaggata aagtcagtct gacctgcatg ataacagact tcttccctga agacattact 480
gtggagtggc agtggaatgg gcagccagcg gagaactaca agaacactca gcccatcatg 540
gacacagatg gctcttactt cgtctacagc aagctcaatg tgcagaagag caactgggag 600
gcaggaaata ctttcacctg ctctgtgtta catgagggcc tgcacaacca ccatactgag 660
aagagcctct cccactctcc tggtaaatga 690

<210> SEQ ID NO 34
<211> LENGTH: 1230
<212> TYPE: DNA
<213> ORGANISM: Artificial Sequence
<220> FEATURE:
<221> NAME/KEY: source
<222> LOCATION: 1..1230
<223> OTHER INFORMATION: /mol_type="unassigned DNA"
/note="HTLV2.RBD fused to a mouse Fc fragment"
/organism="Artificial Sequence"

<400> SEQUENCE: 34
atgggtaatg ttttcttcct acttttattc agtctcacac attttccact agcccagcag 60
agccgatgca cactcacagt tggtatctcc tcctaccact ccagcccctg tagcccaacc 120
caacccgtct gcacgtggaa cctcgacctt aattccctaa caacggacca acgactacac 180 ccccccctgcc ctaacctaat tacttactct ggcttccata agacttattc cttatactta 240
ttcccacatt ggataaaaaa gccaaacaga cagggcctag ggtactactc gccttcctac 300
aatgaccctt gctcgctaca atgcccctac ttgggctgcc aatcatggac atgcccatac 360
acgggccccg tctccagtcc atcctggaag tttcattcag atgtaaattt cacccaggaa 420
gtcagccaag tgtcccttcg actacacttc tctaagtgcg gctcctccat gaccctccta 480
gtagatgccc ctggatatga tcctttatgg ttcatcacct cagaacccac tcagggatcc 540
gtcgacgtgc ccagggattg tggttgtaag ccttgcatat gtacagtccc agaagtatca 600
tctgtcttca tcttcccccc aaagcccaag gatgtgctca ccattactct gactcctaag 660
gtcacgtgtg ttgtggtaga catcagcaag gatgatcccg aggtccagtt cagctggttt 720
gtagatgatg tggaggtgca cacagctcag acgcaacccc gggaggagca gttcaacagc 780

```
actttccgct cagtcagtga acttcccatc atgcaccagg actggctcaa tggcaaggag    840

ttcaaatgca gggtcaacag tgcagctttc cctgccccca tcgagaaaac catctccaaa    900

accaaaggca gaccgaaggc tccacaggtg tacaccattc cacctcccaa ggagcagatg    960

gccaaggata aagtcagtct gacctgcatg ataacagact tcttccctga agacattact   1020

gtggagtggc agtggaatgg gcagccagcg gagaactaca agaacactca gcccatcatg   1080

gacacagatg gctcttactt cgtctacagc aagctcaatg tgcagaagag caactgggag   1140

gcaggaaata ctttcacctg ctctgtgtta catgagggcc tgcacaacca ccatactgag   1200

aagagcctct cccactctcc tggtaaatga                                    1230
```

```
<210> SEQ ID NO 35
<211> LENGTH: 11
<212> TYPE: PRT
<213> ORGANISM: Artificial Sequence
<220> FEATURE:
<223> OTHER INFORMATION: GLUT1 fragment

<400> SEQUENCE: 35

Asn Ala Pro Gln Lys Val Ile Glu Glu Phe Tyr
1               5                   10


<210> SEQ ID NO 36
<211> LENGTH: 22
<212> TYPE: PRT
<213> ORGANISM: Artificial Sequence
<220> FEATURE:
<223> OTHER INFORMATION: GLUT1 fragment

<400> SEQUENCE: 36

Asn Gln Thr Trp Val His Arg Tyr Gly Glu Ser Ile Leu Pro Thr Thr
1               5                   10                  15

Leu Thr Thr Leu Trp Ser
            20


<210> SEQ ID NO 37
<211> LENGTH: 10
<212> TYPE: PRT
<213> ORGANISM: Artificial Sequence
<220> FEATURE:
<223> OTHER INFORMATION: GLUT1 fragment

<400> SEQUENCE: 37

Lys Ser Phe Glu Met Leu Ile Leu Gly Arg
1               5                   10


<210> SEQ ID NO 38
<211> LENGTH: 9
<212> TYPE: PRT
<213> ORGANISM: Artificial Sequence
<220> FEATURE:
<223> OTHER INFORMATION: GLUT1 fragment

<400> SEQUENCE: 38

Asp Ser Ile Met Gly Asn Lys Asp Leu
1               5


<210> SEQ ID NO 39
<211> LENGTH: 14
<212> TYPE: PRT
<213> ORGANISM: Artificial Sequence
<220> FEATURE:
<223> OTHER INFORMATION: GLUT1 fragment
```

<400> SEQUENCE: 39

Tyr Ser Thr Ser Ile Phe Glu Lys Ala Gly Val Gln Gln Pro
1 5 10

<210> SEQ ID NO 40
<211> LENGTH: 10
<212> TYPE: PRT
<213> ORGANISM: Artificial Sequence
<220> FEATURE:
<223> OTHER INFORMATION: GLUT1 fragment

<400> SEQUENCE: 40

Glu Gln Leu Pro Trp Met Ser Tyr Leu Ser
1 5 10

<210> SEQ ID NO 41
<211> LENGTH: 7
<212> TYPE: PRT
<213> ORGANISM: Artificial Sequence
<220> FEATURE:
<223> OTHER INFORMATION: GLUT1 fragment

<400> SEQUENCE: 41

Gln Tyr Val Glu Gln Leu Cys
1 5

<210> SEQ ID NO 42
<211> LENGTH: 13
<212> TYPE: PRT
<213> ORGANISM: Artificial Sequence
<220> FEATURE:
<223> OTHER INFORMATION: GLUT1 fragment

<400> SEQUENCE: 42

Ile Val Gly Met Cys Phe Gln Tyr Val Glu Gln Leu Cys
1 5 10

<210> SEQ ID NO 43
<211> LENGTH: 304
<212> TYPE: PRT
<213> ORGANISM: Artificial Sequence
<220> FEATURE:
<223> OTHER INFORMATION: HTLV2.RBD

<400> SEQUENCE: 43

Met Gly Asn Val Phe Phe Leu Leu Leu Phe Ser Leu Thr His Phe Pro
1 5 10 15

Pro Val Gln Gln Ser Arg Cys Thr Leu Thr Val Gly Ile Ser Ser Tyr
20 25 30

His Ser Ser Pro Cys Ser Pro Thr Gln Pro Val Cys Thr Trp Asn Leu
35 40 45

Asp Leu Asn Ser Leu Thr Thr Asp Gln Arg Leu His Pro Pro Cys Pro
50 55 60

Asn Leu Ile Thr Tyr Ser Gly Phe His Lys Thr Tyr Ser Leu Tyr Leu
65 70 75 80

Phe Pro His Trp Ile Lys Lys Pro Asn Arg Gln Gly Leu Gly Tyr Tyr
85 90 95

Ser Pro Ser Tyr Asn Asp Pro Cys Ser Leu Gln Cys Pro Tyr Leu Gly
100 105 110

Cys Gln Ser Trp Thr Cys Pro Tyr Thr Gly Pro Val Ser Ser Pro Ser
115 120 125

```
Trp Lys Phe His Ser Asp Val Asn Phe Thr Gln Glu Val Ser Gln Val
    130                 135                 140

Ser Leu Arg Leu His Phe Ser Lys Cys Gly Ser Ser Met Thr Leu Leu
145                 150                 155                 160

Val Asp Ala Pro Gly Tyr Asp Pro Leu Trp Phe Ile Thr Ser Glu Pro
                165                 170                 175

Thr Gln Pro Pro Pro Thr Pro Pro Pro Leu Val His Asp Ser Asp Leu
            180                 185                 190

Glu His Val Leu Thr Pro Ser Thr Ser Trp Thr Thr Lys Met Leu Lys
        195                 200                 205

Phe Ile Gln Leu Thr Leu Gln Ser Thr Asn Tyr Ser Cys Met Val Cys
    210                 215                 220

Val Asp Arg Ser Ser Leu Ser Ser Trp His Val Leu Tyr Thr Pro Asn
225                 230                 235                 240

Ile Ser Ile Pro Gln Gln Thr Ser Ser Arg Thr Ile Leu Phe Pro Ser
                245                 250                 255

Leu Ala Leu Pro Ala Pro Pro Phe Gln Pro Phe Pro Trp Thr His Cys
            260                 265                 270

Tyr Gln Pro Arg Leu Gln Ala Ile Thr Thr Asp Asp Cys Asn Asn Ser
        275                 280                 285

Ile Ile Leu Pro Pro Phe Ser Leu Ala Pro Val Pro Pro Pro Ala Thr
    290                 295                 300
```

<210> SEQ ID NO 44
<211> LENGTH: 20
<212> TYPE: PRT
<213> ORGANISM: Artificial Sequence
<220> FEATURE:
<223> OTHER INFORMATION: human IL-2 peptide signal

<400> SEQUENCE: 44

```
Met Tyr Arg Met Gln Leu Leu Ser Cys Ile Ala Leu Ser Leu Ala Leu
1               5                   10                  15

Val Thr Asn Ser
            20
```

<210> SEQ ID NO 45
<211> LENGTH: 18
<212> TYPE: PRT
<213> ORGANISM: Artificial Sequence
<220> FEATURE:
<223> OTHER INFORMATION: human albumine peptide signal

<400> SEQUENCE: 45

```
Met Lys Trp Val Thr Phe Ile Ser Leu Leu Phe Leu Phe Ser Ser Ala
1               5                   10                  15

Tyr Ser
```

<210> SEQ ID NO 46
<211> LENGTH: 18
<212> TYPE: PRT
<213> ORGANISM: Artificial Sequence
<220> FEATURE:
<223> OTHER INFORMATION: human chymotryosinogen peptide signal

<400> SEQUENCE: 46

```
Met Ala Phe Leu Trp Leu Leu Ser Cys Trp Ala Leu Leu Gly Thr Thr
1               5                   10                  15

Phe Gly
```

<210> SEQ ID NO 47
<211> LENGTH: 15
<212> TYPE: PRT
<213> ORGANISM: Artificial Sequence
<220> FEATURE:
<223> OTHER INFORMATION: human trypsinogen-2 peptide signal

<400> SEQUENCE: 47

Met Asn Leu Leu Leu Ile Leu Thr Phe Val Ala Ala Ala Val Ala
1 5 10 15

<210> SEQ ID NO 48
<211> LENGTH: 17
<212> TYPE: PRT
<213> ORGANISM: Artificial Sequence
<220> FEATURE:
<223> OTHER INFORMATION: gaussia luciferase peptide signal

<400> SEQUENCE: 48

Met Gly Val Lys Val Leu Phe Ala Leu Ile Cys Ile Ala Val Ala Glu
1 5 10 15

Ala

<210> SEQ ID NO 49
<211> LENGTH: 21
<212> TYPE: PRT
<213> ORGANISM: Artificial Sequence
<220> FEATURE:
<223> OTHER INFORMATION: Mouse IgM peptide signal

<400> SEQUENCE: 49

Met Lys Phe Ser Trp Val Met Phe Phe Leu Met Ala Val Val Thr Gly
1 5 10 15

Val Asn Ser Glu Phe
20

<210> SEQ ID NO 50
<211> LENGTH: 2208
<212> TYPE: DNA
<213> ORGANISM: Artificial Sequence
<220> FEATURE:
<221> NAME/KEY: source
<222> LOCATION: 1..2208
<223> OTHER INFORMATION: /mol_type="unassigned DNA"
/note="Nucleic acid HTLV4"
/organism="Artificial Sequence"

<400> SEQUENCE: 50
atgggatgtc ttgggaatca gctgcttatc gccatcttgc ttttaagtgt ctatgggatc 60
tattgtactc aatatgtcac agtcttttat ggtgtaccag cttggaggaa tgcgacaatt 120
cccctcttct gtgcaaccaa gaatagggat acttggggaa caactcagtg cctaccagat 180
aatggtgatt attcagaatt ggcccttaat gttacagaaa gctttgatgc ttgggagaat 240
acagtcacag aacaggcaat agaggacgta tggcaactct ttgagacctc aataaagcct 300
tgtgtaaaat tatccccatt atgcattact atgagatgca ataaaagtga gacagataga 360
tggggattga caaaatcatc aacaacaata acaacagcag caccaacatc agcaccagta 420
tcagaaaaaa tagacatggt caatgagact agttcttgta tagctcagaa taattgcaca 480
ggcttggaac aagagcaaat gataagctgt aaattcacca tgacagggtt aaaaagagac 540
aagacaaagg agtacaatga aacttggtac tctacagatt tggtttgtga acaagggaat 600
agcactgata atgaaagcag atgctacata aatcactgta acacttctgt tatccaagag 660

```
tcttgtgaca aacattattg ggatactatt agatttaggt attgtgcacc tccaggttat    720
gctttgctta gatgtaatga cacaaattat tcaggcttta tgcctaaatg ttctaaggtg    780
gtggtctctt catgcacaag gatgatggag acacagactt ctacttggtt tggctttaat    840
ggaactagag cagaaaatag aacttatatt tactggcatg gtagggataa taggactata    900
attagtttaa ataagtatta taatctaaca atgaaatgta gaagaccagg aaataagaca    960
gttttaccag tcaccattat gtctggattg gttttccact cacaaccaat caatgatagg   1020
ccaaagcagg catggtgttg gtttggagga aaatggaagg atgcaataaa agaggtgaaa   1080
cagaccattg tcaaacatcc caggtatact ggaactaaca atactgataa aatcaattta   1140
acggctcctg gaggaggaga tccagaagtt accttcatgt ggacaaattg cagaggagag   1200
ttcctctact gtaaaatgaa ttggtttcta aattgggtag aggataggga tgtaactacc   1260
cagaggccaa aggaacggca tagaaggaat tacgtgccgt gtcatattag acaagtaatc   1320
aacacttggc ataaagtagg caaaaatgtt tatttgcctc caagagaggg agacctcacg   1380
tgtaactcca cagtgaccag tctcatagca aacatagatt ggactgatgg aaaccaaact   1440
aatatcacca tgagtgcaga ggtggcagaa ctgtatcgat tggagttggg agattataaa   1500
ttagtagaga tcactccgat cggcttggcc cccacagatg tgaagaggta cactactggt   1560
ggcacctcaa gaaataaaag aggggtcttt gtgctagggt tcttgggttt tctcgcaacg   1620
gcaggttctg caatgggcgc ggcgtcgttg acgctgaccg ctcagtcccg gactttattg   1680
gctgggatag tgcagcaaca gcaacagctg ttggacgtgg tcaagagaca acaagaattg   1740
ttgcgactga ccgtctgggg aacaaagaac ctccagacta gggtcactgc catcgagaag   1800
tacttaaagg accaggcgca gctgaatact tggggatgtg cgtttagaca agtctgccac   1860
actactgtac catggccaaa tgcaagtcta acaccagact ggaacaatga tacttggcaa   1920
gagtgggagc gaaaggttga cttcttggag gaaaatataa cagccctcct agaagaggca   1980
caaattcaac aagagaagaa catgtatgaa ttacaaaagt taaatagctg ggatgtgttt   2040
ggcaattggt ttgaccttgc ttcttggata aagtatatac aatatggaat ttatgtagtt   2100
gtaggagtaa tactgttaag aatagtgatc tatatagtac aaatgctagc taagttaagg   2160
caggggtata ggccagtgtt ctcttcccca ccctcttatt tccagtag                2208
```

<210> SEQ ID NO 51
<211> LENGTH: 735
<212> TYPE: PRT
<213> ORGANISM: Artificial Sequence
<220> FEATURE:
<223> OTHER INFORMATION: Amino acid HTLV4

<400> SEQUENCE: 51

```
Met Gly Cys Leu Gly Asn Gln Leu Leu Ile Ala Ile Leu Leu Leu Ser
1               5                   10                  15

Val Tyr Gly Ile Tyr Cys Thr Gln Tyr Val Thr Val Phe Tyr Gly Val
            20                  25                  30

Pro Ala Trp Arg Asn Ala Thr Ile Pro Leu Phe Cys Ala Thr Lys Asn
        35                  40                  45

Arg Asp Thr Trp Gly Thr Thr Gln Cys Leu Pro Asp Asn Gly Asp Tyr
    50                  55                  60

Ser Glu Leu Ala Leu Asn Val Thr Glu Ser Phe Asp Ala Trp Glu Asn
65                  70                  75                  80

Thr Val Thr Glu Gln Ala Ile Glu Asp Val Trp Gln Leu Phe Glu Thr
```

-continued

```
                85                  90                  95

Ser Ile Lys Pro Cys Val Lys Leu Ser Pro Leu Cys Ile Thr Met Arg
            100                 105                 110

Cys Asn Lys Ser Glu Thr Asp Arg Trp Gly Leu Thr Lys Ser Ser Thr
        115                 120                 125

Thr Ile Thr Thr Ala Ala Pro Thr Ser Ala Pro Val Ser Glu Lys Ile
    130                 135                 140

Asp Met Val Asn Glu Thr Ser Ser Cys Ile Ala Gln Asn Asn Cys Thr
145                 150                 155                 160

Gly Leu Glu Gln Glu Gln Met Ile Ser Cys Lys Phe Thr Met Thr Gly
                165                 170                 175

Leu Lys Arg Asp Lys Thr Lys Glu Tyr Asn Glu Thr Trp Tyr Ser Thr
            180                 185                 190

Asp Leu Val Cys Glu Gln Gly Asn Ser Thr Asp Asn Glu Ser Arg Cys
        195                 200                 205

Tyr Ile Asn His Cys Asn Thr Ser Val Ile Gln Glu Ser Cys Asp Lys
    210                 215                 220

His Tyr Trp Asp Thr Ile Arg Phe Arg Tyr Cys Ala Pro Pro Gly Tyr
225                 230                 235                 240

Ala Leu Leu Arg Cys Asn Asp Thr Asn Tyr Ser Gly Phe Met Pro Lys
                245                 250                 255

Cys Ser Lys Val Val Val Ser Ser Cys Thr Arg Met Met Glu Thr Gln
            260                 265                 270

Thr Ser Thr Trp Phe Gly Phe Asn Gly Thr Arg Ala Glu Asn Arg Thr
        275                 280                 285

Tyr Ile Tyr Trp His Gly Arg Asp Asn Arg Thr Ile Ile Ser Leu Asn
    290                 295                 300

Lys Tyr Tyr Asn Leu Thr Met Lys Cys Arg Arg Pro Gly Asn Lys Thr
305                 310                 315                 320

Val Leu Pro Val Thr Ile Met Ser Gly Leu Val Phe His Ser Gln Pro
                325                 330                 335

Ile Asn Asp Arg Pro Lys Gln Ala Trp Cys Trp Phe Gly Gly Lys Trp
            340                 345                 350

Lys Asp Ala Ile Lys Glu Val Lys Gln Thr Ile Val Lys His Pro Arg
        355                 360                 365

Tyr Thr Gly Thr Asn Asn Thr Asp Lys Ile Asn Leu Thr Ala Pro Gly
    370                 375                 380

Gly Gly Asp Pro Glu Val Thr Phe Met Trp Thr Asn Cys Arg Gly Glu
385                 390                 395                 400

Phe Leu Tyr Cys Lys Met Asn Trp Phe Leu Asn Trp Val Glu Asp Arg
                405                 410                 415

Asp Val Thr Thr Gln Arg Pro Lys Glu Arg His Arg Arg Asn Tyr Val
            420                 425                 430

Pro Cys His Ile Arg Gln Val Ile Asn Thr Trp His Lys Val Gly Lys
        435                 440                 445

Asn Val Tyr Leu Pro Pro Arg Glu Gly Asp Leu Thr Cys Asn Ser Thr
    450                 455                 460

Val Thr Ser Leu Ile Ala Asn Ile Asp Trp Thr Asp Gly Asn Gln Thr
465                 470                 475                 480

Asn Ile Thr Met Ser Ala Glu Val Ala Glu Leu Tyr Arg Leu Glu Leu
                485                 490                 495

Gly Asp Tyr Lys Leu Val Glu Ile Thr Pro Ile Gly Leu Ala Pro Thr
            500                 505                 510
```

```
Asp Val Lys Arg Tyr Thr Thr Gly Gly Thr Ser Arg Asn Lys Arg Gly
        515                 520                 525

Val Phe Val Leu Gly Phe Leu Gly Phe Leu Ala Thr Ala Gly Ser Ala
    530                 535                 540

Met Gly Ala Ala Ser Leu Thr Leu Thr Ala Gln Ser Arg Thr Leu Leu
545                 550                 555                 560

Ala Gly Ile Val Gln Gln Gln Gln Gln Leu Leu Asp Val Val Lys Arg
                565                 570                 575

Gln Gln Glu Leu Leu Arg Leu Thr Val Trp Gly Thr Lys Asn Leu Gln
            580                 585                 590

Thr Arg Val Thr Ala Ile Glu Lys Tyr Leu Lys Asp Gln Ala Gln Leu
        595                 600                 605

Asn Thr Trp Gly Cys Ala Phe Arg Gln Val Cys His Thr Thr Val Pro
    610                 615                 620

Trp Pro Asn Ala Ser Leu Thr Pro Asp Trp Asn Asn Asp Thr Trp Gln
625                 630                 635                 640

Glu Trp Glu Arg Lys Val Asp Phe Leu Glu Glu Asn Ile Thr Ala Leu
                645                 650                 655

Leu Glu Glu Ala Gln Ile Gln Gln Glu Lys Asn Met Tyr Glu Leu Gln
            660                 665                 670

Lys Leu Asn Ser Trp Asp Val Phe Gly Asn Trp Phe Asp Leu Ala Ser
        675                 680                 685

Trp Ile Lys Tyr Ile Gln Tyr Gly Ile Tyr Val Val Val Gly Val Ile
    690                 695                 700

Leu Leu Arg Ile Val Ile Tyr Ile Val Gln Met Leu Ala Lys Leu Arg
705                 710                 715                 720

Gln Gly Tyr Arg Pro Val Phe Ser Ser Pro Pro Ser Tyr Phe Gln
                725                 730                 735
```

<210> SEQ ID NO 52
<211> LENGTH: 1485
<212> TYPE: DNA
<213> ORGANISM: Artificial Sequence
<220> FEATURE:
<221> NAME/KEY: source
<222> LOCATION: 1..1485
<223> OTHER INFORMATION: /mol_type="unassigned DNA"
/note="Nucleic acid HTLV3"
/organism="Artificial Sequence"

<400> SEQUENCE: 52

```
atgggtaagt ccggtcttta tttcagtctc atttgttttt acacactctt cccttcctct     60

tttggcaatc ccagccgatg caccctgttc ataggagctt cctcctacca ctctgacccc    120

tgtgggtcca accacccacg atgtacctgg agacttgacc tcttttccct cacaaaggat    180

caaagcctaa gccccccatg tccaggctta gttacttact cacagtacca taaaccctac    240

tccctatatg tatttcctca ttggatagcc aaacctgacc gtcgaggcct aggttactat    300

tctgcttcct actcggaccc ctgcgctata caatgccctt acctaggatg ccagtcatgg    360

acgtgcccct atacaggtcc ggtgtccaac ccacattgga aatacacctc tgatcttaac    420

ttcacccaag aagtatcatc catttcccta cacttgcact tttccaaatg tgggtcctca    480

ttctcctttc tattagatgc gccaggatat gacccagtgt ggctcctctc atcccaggcc    540

acccaaattc cacccacgcc cgcccctctc atacaggact cagatctcca acatatcctg    600

gaaccttcta tcccatggag ttctaaaatc cttaacctta tcctccttgc tttaaagagc    660
```

-continued actaattatt cttgcatggt ctgtgtcgat cgctccagcc tctcttcatg gcatgttctg 720
tacgacccac tcaaagcccc cagttcaccc gacccccaag cccagtctat cctacggccc 780
tccttagcca ttcccgccag taacatcacc cctccgtttc cttggaccca ctgctatcgc 840
cctcctctac aggccatctc ctcagaaaac tgcaataact ctgtaatact gccccccttc 900
tccctgtccc caattcctga tgtctctaga ccccggaagc gccgagcagt ccccatcgct 960
atatggctgg tatccgccct agcggccggc acgggtatag caggcggagt taccggctcc 1020
ctgtccctgg cgtccagcaa gagtctgttg cgcgaggttg accaggacat agatcaccta 1080
acccgggcaa ttgtaaagaa ccatgacaac atccttcggg ttgctcagta cgcagcccaa 1140
aatcgccgcg gcctagacct gctttttttgg gagcagggag gtctttgtaa ggccatccag 1200
gagcaatgtt gtttccttaa tatcagcaac acccatgtgt cagtccttca ggaaagacct 1260
cctctagaaa aaagggtaat taccggctgg gggctcaatt gggaccttgg gctctcccaa 1320
tgggcccgag aggccctcca gacaggtata acactcttgg ccctctttct cctcctcatt 1380
gtcgtagggc cctgtgtcat acgtcagctg cagaccctcc cctcccgcct gcagcaccgc 1440
agccaaccct actcccttct caattatgaa accaacttat aataa 1485

<210> SEQ ID NO 53
<211> LENGTH: 493
<212> TYPE: PRT
<213> ORGANISM: Artificial Sequence
<220> FEATURE:
<223> OTHER INFORMATION: Amino acid HTLV3

<400> SEQUENCE: 53

Met Gly Lys Ser Gly Leu Tyr Phe Ser Leu Ile Cys Phe Tyr Thr Leu
1 5 10 15

Phe Pro Ser Ser Phe Gly Asn Pro Ser Arg Cys Thr Leu Phe Ile Gly
20 25 30

Ala Ser Ser Tyr His Ser Asp Pro Cys Gly Ser Asn His Pro Arg Cys
35 40 45

Thr Trp Arg Leu Asp Leu Phe Ser Leu Thr Lys Asp Gln Ser Leu Ser
50 55 60

Pro Pro Cys Pro Gly Leu Val Thr Tyr Ser Gln Tyr His Lys Pro Tyr
65 70 75 80

Ser Leu Tyr Val Phe Pro His Trp Ile Ala Lys Pro Asp Arg Arg Gly
85 90 95

Leu Gly Tyr Tyr Ser Ala Ser Tyr Ser Asp Pro Cys Ala Ile Gln Cys
100 105 110

Pro Tyr Leu Gly Cys Gln Ser Trp Thr Cys Pro Tyr Thr Gly Pro Val
115 120 125

Ser Asn Pro His Trp Lys Tyr Thr Ser Asp Leu Asn Phe Thr Gln Glu
130 135 140

Val Ser Ser Ile Ser Leu His Leu His Phe Ser Lys Cys Gly Ser Ser
145 150 155 160

Phe Ser Phe Leu Leu Asp Ala Pro Gly Tyr Asp Pro Val Trp Leu Leu
165 170 175

Ser Ser Gln Ala Thr Gln Ile Pro Pro Thr Pro Ala Pro Leu Ile Gln
180 185 190

Asp Ser Asp Leu Gln His Ile Leu Glu Pro Ser Ile Pro Trp Ser Ser
195 200 205

Lys Ile Leu Asn Leu Ile Leu Leu Ala Leu Lys Ser Thr Asn Tyr Ser
210 215 220

```
Cys Met Val Cys Val Asp Arg Ser Ser Leu Ser Ser Trp His Val Leu
225                 230                 235                 240

Tyr Asp Pro Leu Lys Ala Pro Ser Ser Pro Asp Pro Gln Ala Gln Ser
                245                 250                 255

Ile Leu Arg Pro Ser Leu Ala Ile Pro Ala Ser Asn Ile Thr Pro Pro
            260                 265                 270

Phe Pro Trp Thr His Cys Tyr Arg Pro Pro Leu Gln Ala Ile Ser Ser
        275                 280                 285

Glu Asn Cys Asn Asn Ser Val Ile Leu Pro Pro Phe Ser Leu Ser Pro
    290                 295                 300

Ile Pro Asp Val Ser Arg Pro Arg Lys Arg Arg Ala Val Pro Ile Ala
305                 310                 315                 320

Ile Trp Leu Val Ser Ala Leu Ala Ala Gly Thr Gly Ile Ala Gly Gly
                325                 330                 335

Val Thr Gly Ser Leu Ser Leu Ala Ser Ser Lys Ser Leu Leu Arg Glu
            340                 345                 350

Val Asp Gln Asp Ile Asp His Leu Thr Arg Ala Ile Val Lys Asn His
        355                 360                 365

Asp Asn Ile Leu Arg Val Ala Gln Tyr Ala Ala Gln Asn Arg Arg Gly
    370                 375                 380

Leu Asp Leu Leu Phe Trp Glu Gln Gly Gly Leu Cys Lys Ala Ile Gln
385                 390                 395                 400

Glu Gln Cys Cys Phe Leu Asn Ile Ser Asn Thr His Val Ser Val Leu
                405                 410                 415

Gln Glu Arg Pro Pro Leu Glu Lys Arg Val Ile Thr Gly Trp Gly Leu
            420                 425                 430

Asn Trp Asp Leu Gly Leu Ser Gln Trp Ala Arg Glu Ala Leu Gln Thr
        435                 440                 445

Gly Ile Thr Leu Leu Ala Leu Phe Leu Leu Leu Ile Val Val Gly Pro
    450                 455                 460

Cys Val Ile Arg Gln Leu Gln Thr Leu Pro Ser Arg Leu Gln His Arg
465                 470                 475                 480

Ser Gln Pro Tyr Ser Leu Leu Asn Tyr Glu Thr Asn Leu
                485                 490


<210> SEQ ID NO 54
<211> LENGTH: 1476
<212> TYPE: DNA
<213> ORGANISM: Artificial Sequence
<220> FEATURE:
<221> NAME/KEY: source
<222> LOCATION: 1..1476
<223> OTHER INFORMATION: /mol_type="unassigned DNA"
      /note="Nucleic acid STLV3"
      /organism="Artificial Sequence"

<400> SEQUENCE: 54

atgggtaagt ccggctttta tttctgtttt atttacactc tcttccctgc ctcctttggc     60

aaccccagtc gatgcaccct gttcataggg gcctcttcct accactccga cccttgtggg    120

tccaatcacc cacaatgtac ctggaggctc gacctattct ccctcacaag ggatcaaagc    180

ctgagccccc catgtccaga cttagtcact tactcacagt atcataaacc ctactccctg    240

tatgtatttc cccattggat ggccaaacct aaccgtcaag gcctaggcta ctattctgct    300

tcctactcag acccttgtgc tatacagtgc ccttacctag gatgccagtc atggacctgt    360

ccctacacag gcccggtgtc cagcccgcat tggaaatact cctccgatct taattttacc    420
```

-continued

```
caagaggtat catctatctc cctacactta catttttcca aatgcgggtc ttcattctct    480

tttctactag atgcaccggg gtacgaccct gtgtggttcc tctcctccca ggccacacag    540

gttccaccca cgcccgcccc tctcatacag gactctaatc tccaacatat cctggaaccc    600

tccgtcccgt ggagctccaa aatcctcaat ctcatcctcc tcaccttaaa aagcactaac    660

tattcttgta tggtctgtgt cgaccgctcc agcctatctt cgtggcatgt tctatatgac    720

ccactcaaag cccccggtcc acccgacccc caagcccagt ctatcttgcg accctcctta    780

gccattcccg ccagtaatat cacccctccg tttccctgga cccattgcta tcgccctctt    840

ctacaggcca tctcctcaga acactgcaac aactccgtag tgctgccccc cttttccctg    900

tccccacttc ctaacgcctt cagaccccga aagcgccggg cagtccccat cgccatatgg    960

ctagtatccg cccttgcggc cggcaccggt atagctggtg gagttacagg ctccctgtct   1020

ctggcctccg gcaaaagcct gttacacgaa gtagaccaag acatagatca cctgacgcgg   1080

gcaattgtaa agaaccatga caatatcctt cgggtcgctc agtatgcagc ccaaaatcgt   1140

cgcggcctag atctgctttt ctgggaacaa ggaggccttt gtaaggccat ccaagagcaa   1200

tgttgtttcc tcaatatcag taacacccat gtgtccgtcc tccaggaaag accccccccta  1260

gaaaaaagag taatcacggg ctgggggctc aattgggacc tcgggctctc ccaatgggcc   1320

cgagaggccc ttcagacagg tataaccctc ttggccctct ttctcctcct tattgtggtc   1380

gggccctgcg tcatacgcca gctgcaggcc ctcccttccc gcctgcagcc tcgcagccag   1440

ccctactccc ttctaaatta tgaaaccaac ttataa                             1476
```

<210> SEQ ID NO 55
<211> LENGTH: 491
<212> TYPE: PRT
<213> ORGANISM: Artificial Sequence
<220> FEATURE:
<223> OTHER INFORMATION: Amino acid STLV3

<400> SEQUENCE: 55

```
Met Gly Lys Ser Gly Phe Tyr Phe Cys Phe Ile Tyr Thr Leu Phe Pro
1               5                   10                  15

Ala Ser Phe Gly Asn Pro Ser Arg Cys Thr Leu Phe Ile Gly Ala Ser
            20                  25                  30

Ser Tyr His Ser Asp Pro Cys Gly Ser Asn His Pro Gln Cys Thr Trp
        35                  40                  45

Arg Leu Asp Leu Phe Ser Leu Thr Arg Asp Gln Ser Leu Ser Pro Pro
    50                  55                  60

Cys Pro Asp Leu Val Thr Tyr Ser Gln Tyr His Lys Pro Tyr Ser Leu
65                  70                  75                  80

Tyr Val Phe Pro His Trp Met Ala Lys Pro Asn Arg Gln Gly Leu Gly
                85                  90                  95

Tyr Tyr Ser Ala Ser Tyr Ser Asp Pro Cys Ala Ile Gln Cys Pro Tyr
            100                 105                 110

Leu Gly Cys Gln Ser Trp Thr Cys Pro Tyr Thr Gly Pro Val Ser Ser
        115                 120                 125

Pro His Trp Lys Tyr Ser Ser Asp Leu Asn Phe Thr Gln Glu Val Ser
    130                 135                 140

Ser Ile Ser Leu His Leu His Phe Ser Lys Cys Gly Ser Ser Phe Ser
145                 150                 155                 160

Phe Leu Leu Asp Ala Pro Gly Tyr Asp Pro Val Trp Phe Leu Ser Ser
                165                 170                 175
```

-continued

```
Gln Ala Thr Gln Val Pro Pro Thr Pro Ala Pro Leu Ile Gln Asp Ser
            180                 185                 190

Asn Leu Gln His Ile Leu Glu Pro Ser Val Pro Trp Ser Ser Lys Ile
        195                 200                 205

Leu Asn Leu Ile Leu Leu Thr Leu Lys Ser Thr Asn Tyr Ser Cys Met
    210                 215                 220

Val Cys Val Asp Arg Ser Ser Leu Ser Ser Trp His Val Leu Tyr Asp
225                 230                 235                 240

Pro Leu Lys Ala Pro Gly Pro Pro Asp Pro Gln Ala Gln Ser Ile Leu
                245                 250                 255

Arg Pro Ser Leu Ala Ile Pro Ala Ser Asn Ile Thr Pro Pro Phe Pro
            260                 265                 270

Trp Thr His Cys Tyr Arg Pro Leu Leu Gln Ala Ile Ser Ser Glu His
        275                 280                 285

Cys Asn Asn Ser Val Val Leu Pro Pro Phe Ser Leu Ser Pro Leu Pro
    290                 295                 300

Asn Ala Phe Arg Pro Arg Lys Arg Arg Ala Val Pro Ile Ala Ile Trp
305                 310                 315                 320

Leu Val Ser Ala Leu Ala Ala Gly Thr Gly Ile Ala Gly Gly Val Thr
                325                 330                 335

Gly Ser Leu Ser Leu Ala Ser Gly Lys Ser Leu Leu His Glu Val Asp
            340                 345                 350

Gln Asp Ile Asp His Leu Thr Arg Ala Ile Val Lys Asn His Asp Asn
        355                 360                 365

Ile Leu Arg Val Ala Gln Tyr Ala Ala Gln Asn Arg Arg Gly Leu Asp
    370                 375                 380

Leu Leu Phe Trp Glu Gln Gly Gly Leu Cys Lys Ala Ile Gln Glu Gln
385                 390                 395                 400

Cys Cys Phe Leu Asn Ile Ser Asn Thr His Val Ser Val Leu Gln Glu
                405                 410                 415

Arg Pro Pro Leu Glu Lys Arg Val Ile Thr Gly Trp Gly Leu Asn Trp
            420                 425                 430

Asp Leu Gly Leu Ser Gln Trp Ala Arg Glu Ala Leu Gln Thr Gly Ile
        435                 440                 445

Thr Leu Leu Ala Leu Phe Leu Leu Leu Ile Val Val Gly Pro Cys Val
    450                 455                 460

Ile Arg Gln Leu Gln Ala Leu Pro Ser Arg Leu Gln Pro Arg Ser Gln
465                 470                 475                 480

Pro Tyr Ser Leu Leu Asn Tyr Glu Thr Asn Leu
                485                 490
```